US010557171B2

(12) United States Patent
Vaidya et al.

(10) Patent No.: US 10,557,171 B2
(45) Date of Patent: *Feb. 11, 2020

(54) METHODS FOR THE TREATMENT OF KIDNEY FIBROSIS

(71) Applicant: THE BRIGHAM AND WOMEN'S HOSPITAL, INC., Boston, MA (US)

(72) Inventors: Vishal S. Vaidya, Cambridge, MA (US); Florin Craciun, Wellesley, MA (US); Amrendra K. Ajay, Boston, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/140,914

(22) Filed: Sep. 25, 2018

(65) Prior Publication Data

US 2019/0010551 A1 Jan. 10, 2019

Related U.S. Application Data

(63) Continuation of application No. 15/124,450, filed as application No. PCT/US2015/019830 on Mar. 11, 2015, now Pat. No. 10,119,168.

(60) Provisional application No. 61/951,778, filed on Mar. 12, 2014.

(51) Int. Cl.
| | |
|---|---|
| *C12Q 1/6883* | (2018.01) |
| *A61K 31/519* | (2006.01) |
| *C12Q 1/68* | (2018.01) |
| *A61K 31/185* | (2006.01) |
| *A61K 31/593* | (2006.01) |

(52) U.S. Cl.
CPC .......... *C12Q 1/6883* (2013.01); *A61K 31/185* (2013.01); *A61K 31/519* (2013.01); *A61K 31/593* (2013.01); *C12Q 1/68* (2013.01); *C12Q 2600/106* (2013.01); *C12Q 2600/118* (2013.01); *C12Q 2600/158* (2013.01)

(58) Field of Classification Search
CPC .. A61K 31/519; A61K 31/185; A61K 31/593; C12Q 1/6883; C12Q 1/158; C12Q 1/106; C12Q 1/118
See application file for complete search history.

(56) References Cited

U.S. PATENT DOCUMENTS

| | | |
|---|---|---|
| 2010/0322926 A1 | 12/2010 | Saint-Mezard |
| 2013/0344196 A1 | 12/2013 | Al-Murrani et al. |

FOREIGN PATENT DOCUMENTS

| | | |
|---|---|---|
| WO | 2013/059879 A1 | 5/2013 |

OTHER PUBLICATIONS

Ju et al. (the American J. of pathology 174(6): 2003).*
Vlanna et al. (Review article J Bras Nefrol 2011 ;33(3):351-364.*
Melk et al. (Kidney International, Vo! 68 (2006), pp. 2667-2679).*
Kushnir et al. (J. biomolecular Techniques 20: 101-108 (2009).*
Human Fibrinogen ELISA Kit, AssayPro.com, Catalog No. ef2040 (Feb. 9, 2006), attached as pdf, available athttp://www.assaypro.com/datasheet!ef2040_1.pdf.
Ju et al., "Renal gene and protein expression signatures for prediction of kidney disease progression." The American Journal of Pathology 174(6):2073-2085 (2009).
Melk et al., "Transcriptional analysis of the molecular basis of human kidney aging using cDNA microarray profiling." Kidney International 68(6):2667-2679 (2005).
Schneider et al., "Cadherin-11 contributes to pulmonary fibrosis: potential role in TGF-β production and epithelial to mesenchymal transition", FASEB J. 26(2):503-512 (2012).
Vianna et al., "Inflammation in chronic kidney disease: the role of cytokines." Jornal Brasileiro de Nefrologia 33(3):351-364 (2011).

* cited by examiner

*Primary Examiner* — Shirley V Gembeh
(74) *Attorney, Agent, or Firm* — Nixon Peabody LLP; David S. Resnick; Nicole D. Kling

(57) ABSTRACT

The technology described herein is directed to the diagnosis, prognosis, and treatment of kidney fibrosis, e.g., chronic kidney disease.

18 Claims, 14 Drawing Sheets

Specification includes a Sequence Listing.

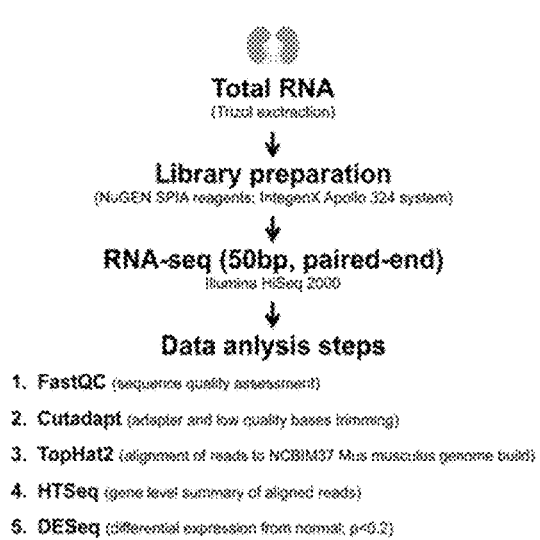
Fig. 1A
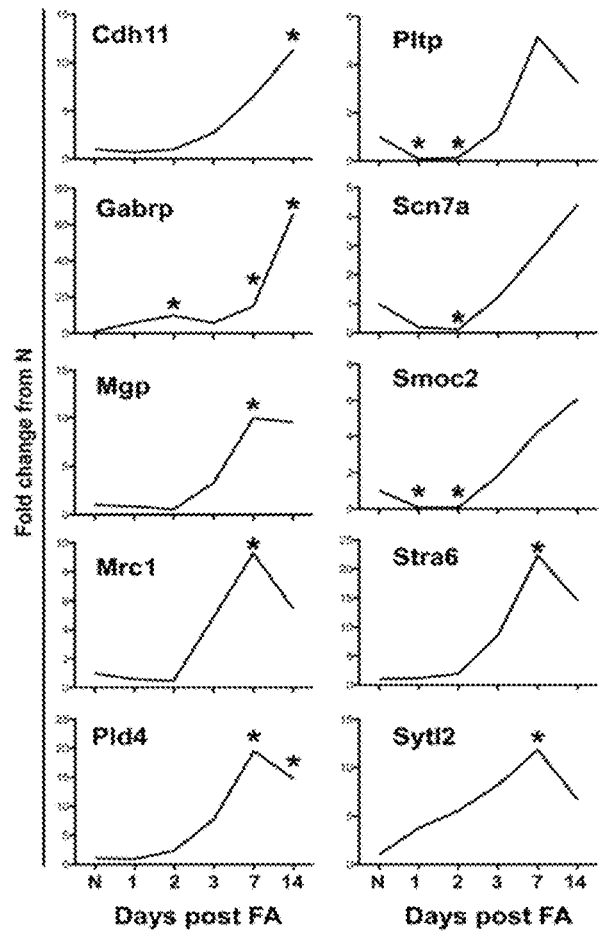
Fig. 1D
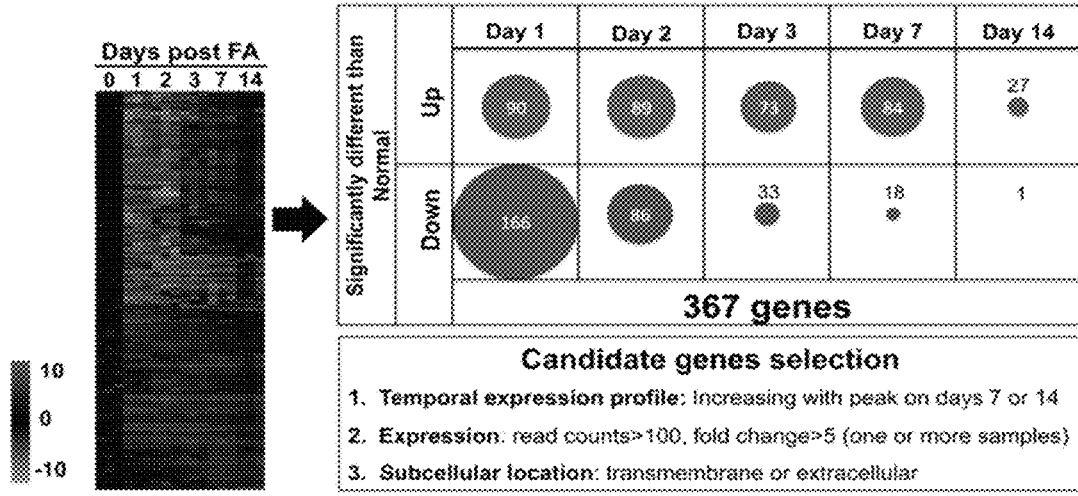
Fig. 1B
Fig. 1C

SEQUENCE LISTING

<160> NUMBER OF SEQ ID NOS: 93

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu His Ser Asp Ile Asp Ser Gly Asp Gly Asn Ile Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Leu Asp Val Asn Asp Asn Ala Pro Lys
1               5                   10

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgccaatctt cttttcgttc tt                                              22

<210> SEQ ID NO 4
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttgaaagg tccattgctg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtggaggtc agcagaagtg                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagtgctatc cgaactgggt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggcagactc acaggacacc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggactccat gctttcgtga                                              20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctcttaatt cagcatcact tgc                                          23

<210> SEQ ID NO 10
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 10
tgcattgccc agtaaggagt                                                   20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
attctgggtt gtggatggg                                                    19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caaggtcttg agccaggttg                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 tgagggcgt gtcactactt                                                    20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgagatcatc cacagaactg c                                                 21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaatgaaacg ctgcacaaca                                                   20

<210> SEQ ID NO 16
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 16
cagcatctgt cctgttgcc                                                    19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actgcgacat gaacaatgac a                                                 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actttcagca tttcctctgg g                                                 21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgccttcctt ctatcctgtc c                                                 21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggaccacaa agacagcagc                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgaaggaatg ccttgacctc                                                   20

<210> SEQ ID NO 22
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 22
acagctcttg tcttctggcg                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgactggaag agcggagagt                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttcgggctg atgtaccagt                                                   20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgtggaccc ctcctgatag t                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcccagtgat ttcagcaaag g                                                 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggaagtaaag ggggtagtgg g                                                 21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
aagcagaaga tgggcattgc                                              20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaatacggct acagcaacag g                                            21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtctgggat ggaaattgtg                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agggacaacc aaagtgacga                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggctgcttct gacacagaca                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagtcaccag atcgcagcag                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaacattcct ccgaagctca                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgaaaccat gaagagcctg                                                    20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aactgaaacg atatcaaagc cg                                                 22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aggaaaagct gccaacaaca                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcctgaggtc aaggaactgg                                                    20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggtgcagc ccaaggac                                                      18

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 40
ggatgctttc cacaaggaca                                                    20

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cggtcctgct caactccc                                                      18

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaagtccatg tccaggttgc                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agcccttgga agatgtggac                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aagccgcatt gaatctgaag                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccgtacaaga actgatgggc                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
```
ctttcagcat gacctctggg                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctccagaccc tgacctctca                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agcaggacaa gaccaaggct                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccagtatgtc ccagagccag                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgacttcccc ttagcagtgg                                               20

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aggctggtgt gatgggatt                                                19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggaacacctc gctctccag                                                19

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
attgccctca acgaccactt tg                                            22

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tctctcttcc tcttgtgctc ttgc                                          24

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu His Ser Asp Ile Asp Ser Gly Asp Gly Asn Ile Lys
1               5                   10

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Ile Phe Ser Leu Pro Pro Glu Ile Ile His Asn Pro Asn Phe Thr
1               5                   10                  15

Val Arg

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Leu Asp Val Asn Asp Asn Ala Pro Lys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Val Glu Ala Ala Asn Val His Ile Asp Pro Lys
1               5                   10

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Leu Ser Leu Pro Gly Phe Glu Asn Leu Thr Ala Gly Tyr Asn Lys
1               5                   10                  15

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Phe Leu His Glu Val Thr Val Gly Asn Arg
1               5                   10

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Val Asp Tyr Phe Thr Ile Gln Asn Pro Ser Asn Val Asp His Tyr
1               5                   10                  15

Ser Lys

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Phe Ser Asn Gly Thr Val Leu Tyr Ala Leu Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Ala Asn Thr Phe Ile Ser Pro Gln Gln Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Ala Met Val Tyr Gly Tyr Asn Ala Ala Tyr Asn Arg
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Lys Pro Val His Glu Leu Asn Arg
1               5

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Tyr Gly Thr Thr Asp Asn Leu Cys Ser Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Gly Ile Ala Gly Gly Leu Trp Asp Val Leu Lys
1               5                   10

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Asp Thr Leu Leu Gly Ile Lys
1               5

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 69

Ala Leu Gly Gly Asp Leu Ala Ser Ile Asn Asn Lys
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Phe Ile Val Pro Val Gly Asn His Ser Asn Ile Pro Phe Ser Arg
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Leu Gln Ala Leu Ser Asn Pro Ala Ala Asn Val Ser Val Asp Val
1               5                   10                  15

Lys

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ser Thr Asp Leu Gln Val Leu Ala Ala Arg
1               5                   10

<210> SEQ ID NO 73
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Gln Pro Phe His Gly Leu Phe Asp Gly Val Pro Thr Thr Ala Tyr
1               5                   10                  15

Phe Ser Ala Ser Pro Pro Ala Leu Cys Pro Gln Gly Arg
            20                  25

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Ser Asn Val Ser Cys Gln Ala Ser Val Ser Arg
1               5                   10
```

```
<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Gly His Phe Tyr Tyr Asn Ile Ser Glu Val Lys
1               5                   10

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Tyr Ser Asn His Ser Ala Leu Glu Ser Leu Ala Leu Ile Pro Leu
1               5                   10                  15

Gln Ala Pro Leu Lys
            20

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Val Glu Pro Gln Leu Gln Glu Glu Glu Arg
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Ser Pro Leu Asp Phe Ile Pro Thr Leu Gln Thr Ala Arg
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Gly Gly Ser Asn Ile Phe Ile Thr Val Lys
1               5                   10

<210> SEQ ID NO 80
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 80

Ala Tyr Phe Ser Asn Gly Trp Tyr Arg
1               5

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Pro Gln Glu Asn Glu Asn Glu Thr Leu His Asn Arg
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ser Glu Pro Asp Pro Ser His Thr Leu Glu Glu Arg
1               5                   10

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Ser Val Ser Ser Cys Asp Gln Glu His Gln Ser Ala Leu Glu Glu
1               5                   10                  15

Ala Lys

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Pro Thr Leu Trp Thr Glu Gln Val Lys
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Ile Ser Val Gln Glu Leu Met Gly Cys Leu Gly Val Ala Lys
```

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ala Ala Leu Asp Leu Ser Pro Leu His Arg
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Leu Gln Ser Ser Tyr Ser Glu Glu Tyr Leu Arg
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ala Thr Leu Asp Pro Gly Tyr Tyr Thr Tyr Arg
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

His Gly Phe Leu Ser Trp Ala Arg
1               5

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Asn Ile Gln Phe Ala Ile Glu Tyr Val Glu Ser Leu Lys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic

```
                          -continued peptide

<400> SEQUENCE: 91

Ile Val Ser Pro Gly Leu Thr Ile His Glu Arg
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Thr Asn Gln Phe Leu Gly Gly Leu Arg
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Val Pro Ala Phe Leu Gln Asp Glu Ser Asp Asp Arg
1               5                   10
```

METHODS FOR THE TREATMENT OF KIDNEY FIBROSIS

CROSS-REFERENCE TO RELATED APPLICATIONS

This application is a continuation under 35 U.S.C. § 120 of co-pending U.S. application Ser. No. 15/124,450 filed Sep. 8, 2016, which is a 35 U.S.C. § 371 National Phase Entry Application of International Application No. PCT/US2015/019830 filed Mar. 11, 2015, which designates the U.S. and claims benefit under 35 U.S.C. § 119(e) of U.S. Provisional Application No. 61/951,778 filed Mar. 12, 2014, the contents of which are incorporated herein by reference in their entireties.

SEQUENCE LISTING

The sequence listing of the present application has been submitted electronically via EFS-Web as an ASCII formatted sequence listing with a file name "043214-081041-PCT_SL", creation date of May 1, 2015 and a size of 22,680 bytes. The sequence listing submitted via EFS-Web is part of the specification and is herein incorporated by reference in its entirety.

TECHNICAL FIELD

The technology described herein relates to the diagnosis, prognosis, and treatment of chronic kidney disease and/or kidney fibrosis.

BACKGROUND

Chronic kidney disease (CKD) has reached global epidemic levels and more than 20 millions U.S. adults currently live with it, many of them not diagnosed. The current biomarkers for detecting and monitoring the progression of CKD, estimation of glomerular filtration rate (eGFR) and measurement of protein/albumin in the urine lack sensitivity and specificity and show alterations only when a significant amount of structural damage has already happened. Earlier and better biomarkers are needed to improve detection of CKD development but also the preservation of kidney function for a longer duration even while using the current limited treatment arsenal.

SUMMARY

As described herein, the inventors have discovered a panel of genes which are upregulated at very early stages of kidney fibrosis, e.g., chronic kidney disease (CKD). The increase expression is detectable in urine. Accordingly, described herein are methods of diagnosis and prognosing kidney fibrosis (e.g. CKD) by detecting expression of one or more of these biomarkers. Further provided herein are methods of treating kidney fibrosis (e.g., CKD) by modulating the expression of these genes.

In one aspect, described herein is a method of treating kidney fibrosis and/or chronic kidney disease, the method comprising; administering a therapeutically effective amount of a kidney fibrosis treatment to a subject determined have a level of expression of at least one gene selected from Table 5 that is increased relative to a reference level. In one aspect, described herein is a method of treatment for kidney fibrosis and/or chronic kidney disease comprising; measuring a level of expression of at least one gene selected from Table 5 in a test sample obtained from a subject; treating the subject with a kidney fibrosis treatment when the expression level is increased relative to a reference level. In some embodiments, the kidney fibrosis treatment is selected from the group consisting of: dialysis; transplant; low protein diet; an ACE inhibitor; an angiotensin II receptor blocker (ARB); lipid control (e.g., statins); D-vitamin supplementation; phosphate control; anemia control (e.g., erythroid stimulating agents); acidosis prevention (e.g., sodium bicarbonate); and uric acid control (e.g., allopurinol). In one aspect, described herein is an assay comprising: measuring the expression level of at least one gene selected from Table 5 in a test sample obtained from a subject; wherein an increase in the expression level of at least one gene selected from Table 5 relative to a reference level indicates the subject has a higher risk of having or developing kidney fibrosis and/or chronic kidney disease. In one aspect, described herein is a method of identifying a subject in need of treatment for kidney fibrosis and/or chronic kidney disease, the method comprising: measuring the level of expression of at least one gene selected from Table 5 in a test sample obtained from a subject; and identifying the subject as being in need of treatment for kidney fibrosis and/or chronic kidney disease when the expression level in the sample is increased relative to a reference level. In one aspect, described herein is a method of determining if a subject is at risk for kidney fibrosis and/or chronic kidney disease, the method comprising: providing a sample obtained from the subject; measuring the level of expression of at least one gene selected from Table 5 in a test sample obtained from a subject; comparing the expression level in the sample to a reference expression level; determining that the subject is at risk for kidney fibrosis and/or chronic kidney disease when the expression level in the sample is increased relative to a reference level; and determining that the subject is not at risk for kidney fibrosis and/or chronic kidney disease when the expression level in the sample is not increased relative to a reference level. In one aspect described herein is a method of determining the efficacy of a treatment for kidney fibrosis and/or chronic kidney disease, the method comprising: (a) measuring a level of expression of at least one gene selected from Table 5 in a test sample obtained from a subject before administration of the treatment; (b) measuring the level of expression of the at least one gene in a test sample obtained from a subject after administration of the treatment; and (c) determining that the treatment is efficacious when the expression level determined in step (b) is decreased relative to the expression level determined in step (a).

In some embodiments, the test sample is a urine sample. In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the at least one gene is selected from the group consisting of: Cdh11; Gabrp; Mgp; Pld4; Smoc2; Mrc1; Sytl2; Stra6; Scn7a; and Pltp. In some embodiments, the at least one gene is selected from the group consisting of: Cdh11; Mrc1; Pltp; Smoc2 and MGP. In some embodiments, the at least one gene is selected from the group consisting of: Cdh11; Mrc1; and Pltp. In some embodiments, the test sample is a urine sample and the at least one protein is selected from the group consisting of: Cdh11; Mrc1; Pltp; Smoc2 and MGP. In some embodiments, the test sample is a urine sample and the at least one gene is selected from the group consisting of: Cdh11; Mrc1; and Pltp. In some embodiments, the at least one gene is selected from the group consisting of: Cdh11 and Mrc1.

In some embodiments, the kidney fibrosis is chronic progressive fibrosis. In some embodiments, the expression level of the at least one gene selected from Table 5 is determined by measuring the level of a nucleic acid. In some embodiments, the expression level is measured by measuring the level of the gene's RNA transcript. In some embodiments, the level of the nucleic acid is measured using a method selected from the group consisting of: RT-PCR; quantitative RT-PCR; Northern blot; microarray based expression analysis; next-generation sequencing; and RNA in situ hybridization. In some embodiments, the expression level of the at least one gene selected from Table 5 is measured by measuring the level of the gene's polypeptide expression product. In some embodiments, the level of the polypeptide is measured using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the polypeptide level is measured using immunochemistry. In some embodiments, the measuring step comprises an ELISA assay; mass spectrometry based Multiple Reaction Monitoring (MRM) assay; or selected reaction monitoring (SRM) assay. In some embodiments, the method or assay can further comprise depleting the sample of abundant proteins prior to the measuring step. In some embodiments, the depletion step comprises affinity chromatography. In some embodiments, the antibody reagent is detectably labeled or generates a detectable signal.

In some embodiments, the expression level of the at least one gene selected from Table 5 is normalized relative to the expression level of one or more reference genes or reference proteins. In some embodiments, the reference level is the expression level of in a prior sample obtained from the subject. In some embodiments, the expression level of at least two genes selected from Table 5 are measured. In some embodiments, the expression level of at least three genes selected from Table 5 are measured. In some embodiments, the expression level of at least four genes selected from Table 5 are measured.

In some embodiments, the subject is a subject with a condition selected from the group consisting of: diabetes; hypertension; acute kidney injury; chronic kidney disease; an autoimmune disease (e.g. systemic lupus erythematosus); renal transplant rejection; renal or systemic infections (e.g. streptococcal infections, bacterial endocarditis, human immunodeficiency virus, hepatitis B, C); and inflammatory or infiltrative disease (e.g. membranoproliferative glomerulonephritis, IgA nephropathy); chemical toxicity poisoning (e.g. drugs, toxins, metals); mechanical damage affecting the kidneys; renal ischemia (e.g. microangiopathies, renal artery occlusion, renal atheroembolism, renal vein thrombosis); obstruction of the urinary tract (e.g. nephrolithiasis); primary genetic alterations (e.g. polycystic kidney disease); and idiopathic chronic kidney disease. In some embodiments, the method can further comprise the step of administering a treatment for kidney fibrosis.

In some embodiments, the treatment comprises administering an antagonist or agonist of at least one gene selected from Table 5. In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the at least one gene is selected from the group consisting of Cdh11; Gabrp; Mgp; Pld4; Smoc2; Mrc1; Sytl2; Stra6; Scn7a; and Pltp. In some embodiments, the at least one gene is selected from the group consisting of: Cdh11; Mrc1; Pltp; Smoc2 and MGP. In some embodiments, the at least one gene is selected from the group consisting of: Cdh11; Mrc1; and Pltp. In some embodiments, the at least one gene is selected from the group consisting of: Cdh11 and Mrc1.

In one aspect, described herein is a kit for performing the method/assay of any of the foregoing aspects.

In one aspect, described herein is a method of treating kidney fibrosis and/or chronic kidney disease, the method comprising administering an antagonist or agonist of at least one gene selected from Table 5. In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the at least one gene is selected from the group consisting of Cdh11; Gabrp; Mgp; Pld4; Smoc2; Mrc1; Sytl2; Stra6; Scn7a; and Pltp. In some embodiments, the at least one gene is selected from the group consisting of: Cdh11; Mrc1; Pltp; Smoc2 and MGP. In some embodiments, the at least one gene is selected from the group consisting of: Cdh11; Mrc1; and Pltp. In some embodiments, the at least one gene is selected from the group consisting of: Cdh11 and Mrc1. In some embodiments, the kidney fibrosis is chronic progressive fibrosis.

In one aspect, described herein is the use of an antagonist or agonist of at least one gene selected from Table 5, the use comprising administering the antagonist or agonist to a subject in need of treatment for kidney fibrosis and/or chronic kidney disease. In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the at least one gene is selected from the group consisting of Cdh11; Gabrp; Mgp; Pld4; Smoc2; Mrc1; Sytl2; Stra6; Scn7a; and Pltp. In some embodiments, the at least one gene is selected from the group consisting of: Cdh11; Mrc1; Pltp; Smoc2 and MGP. In some embodiments, the at least one gene is selected from the group consisting of: Cdh11; Mrc1; and Pltp. In some embodiments, the at least one gene is selected from the group consisting of: Cdh11 and Mrc1. In some embodiments, the kidney fibrosis is chronic progressive fibrosis. In some embodiments, the antagonist is selected from the group consisting of an inhibitory nucleic acid; an aptamer; an antibody reagent; an antibody; and a small molecule.

BRIEF DESCRIPTION OF THE DRAWINGS

FIGS. 1A-1D demonstrate the selection of 10 candidate genes as potential biomarkers for kidney fibrosis development. FIG. 1A depicts a schematic of the steps taken for the RNA-seq analysis from retrieval of kidney tissue to generation of lists of genes with expression significantly different from that in normal mice. FIG. 1B demonstrates that hierarchical clustering grouped the temporal profiles of gene expression variation. Data is shown as the average fold change from normal with 3 samples for each gene and each time-point (log 2 scale). Only the 367 genes that showed significant variation at the p<0.2 level at least for one time-point are shown. FIG. 1C depicts a breakdown of numbers of significantly up or down regulated genes at each time-point and selection criteria for kidney fibrosis biomarker candidate genes. FIG. 1D demonstrates that fold changes from normal for the 10 candidates selected for follow-up. Data is shown as the mean for the 3 samples included in RNA-seq at each time-point. * indicates time-points when p<0.2 for the fold change from normal.

FIG. 4A depicts quantitative RT-PCR based measurement of collagen 1a1 mRNA expression in kidneys from FA injected mice at the 2 doses indicated above. FIG. 4B depicts kidney mRNA expression for the 11 candidate genes in High dose vs. Low dose FA injected mice. For both (FIGS. 4A and 4B) qRT-PCR data was normalized to GAPDH and is represented as mean±SEM of the fold change from normal. n=6/group. * p<0.05 when compared to Low dose group for each gene. FIG. 4C depicts decreased kidney expression of collagen 1a1 by qRT-PCR and (FIG. 4D) the 11 candidate genes in enalapril treated mice compared to control. For FIGS. 4C and 4D, qRT-PCR data was normalized to GAPDH and is represented as mean±SEM of the fold change from normal. n=6/group. * p<0.05 when compared to Enalapril group for each gene.

FIGS. 5A-5B demonstrate that Collagen 1a1 (FIG. 5A) and 11 other candidate genes (FIG. 5B) mRNA expression in ANIT vs. control diet mice at the 4 week time-point. qRT-PCR data was normalized to GAPDH and is represented as mean±SEM of the fold change from control. n=5/group. * p<0.05 when compared to control group for each gene (control groups, all with a mean of 1, are not figured in FIG. 5B). # indicates that a fold change could not be calculated due to low expression in one or both groups. FIGS. 5C-5D demonstrate Collagen 1a1 (FIG. 5C) and 11 other candidate genes (FIG. 5D) mRNA expression in liver tissue from PSC patients compared to Normal. qRT-PCR data was normalized to GAPDH and is represented as mean±SEM of the fold change from Normal. n=6 for Normal and 15 for Fibrotic groups. * p<0.05 when compared to Normal group for each gene (Normal groups, all with a mean of 1, are not figured in FIG. 5D). # indicates that a fold change could not be calculated due to low expression in one or both groups.

FIG. 6A depicts a workflow describing sample processing and mass spectrometry analysis. FIG. 6B depicts SRM chromatogram of peptides LHSDIDS-GDGNIK (SEQ ID NO: 1) and VLDVNDNAPK (SEQ ID NO: 2) from Cdh11 detected in diseased urine sample. Transitions of the endogenous light (top) and spiked-in isotope labeled heavy peptide (bottom) elute at the same retention time and rank order. FIG. 6C depicts detection of Cdh11, Mrc1, and Pltp in patient samples with CKD (n=22) compared to healthy (n=24). Relative abundance in individual samples is based on the normalized area ratio of endogenous peptide to internal standard. * p<0.05 when compared to healthy.

FIG. 8A depicts plasma levels of BUN and SCr. n=7-10/group for the FA model, and 4-5/group for other models. Data is presented as mean±SEM. *p<0.05 when compared to N (or Sham for Unil-IRI model where samples were collected at 41 days). FIG. 8B depicts qRT-PCR determination of kidney expression levels of fibrosis (Col1a1 and Fn1) and acute injury (Kim-1) markers. For FA nephropathy model n=6/group; for Unil-IRI model n=4 for Sham groups and 5 for IRI groups; for all other models n=5/group. Data was normalized to GAPDH and is presented as mean±SEM of the fold change from normal (N) group in each model. For Unil-IRI N were the contralateral (CoK) kidneys from the sham-operated mice. *p<0.05 when compared to N.

DETAILED DESCRIPTION

Figure 2:
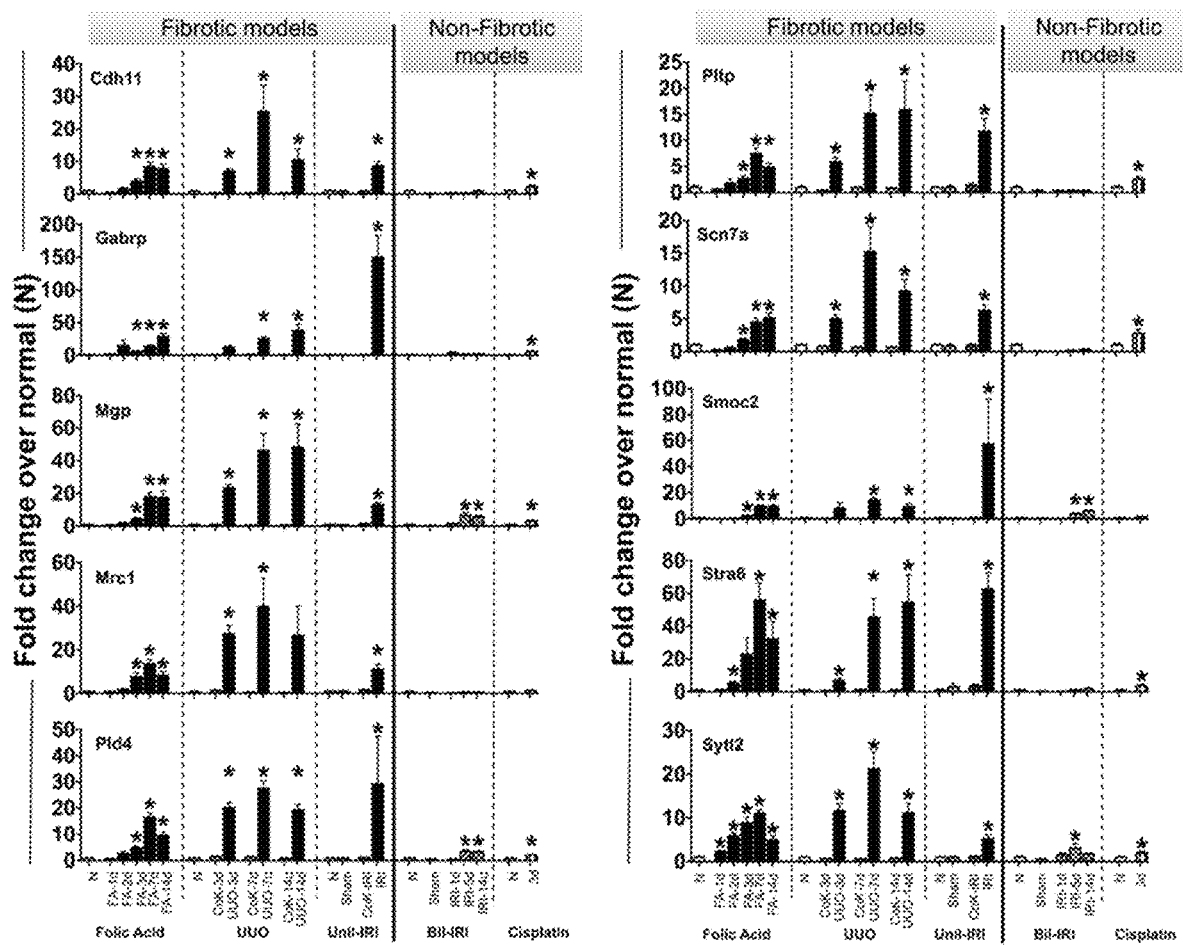
FIG. 2 demonstrates expression levels for the 10 candidate genes in mouse models of kidney fibrosis and acute kidney injury. The mRNA expression was assessed by qRT-PCR in the following mouse models: folic acid (FA) nephropathy model (n=6/group), unilateral ureteral obstruction (UUO, n=5/group), unilateral ischemia reperfusion injury (Uni-IRI, n=4 for sham groups and 5 for Uni-IRI groups, samples collected at 42 days post Uni-IRI) models, bilateral ischemia reperfusion injury (Bil-IRI) and cisplatin-induced acute kidney injury (n=5/group). Data was normalized to GAPDH and is presented as mean±SEM of the fold change from normal (N) group in each model. For Unil-IRI N were the contralateral (CoK) kidneys from the sham-operated mice. *p<0.05 when compared to N.

As described herein, the inventors have found that in subjects with kidney fibrosis, e.g., subjects with chronic kidney disease, a number of genes are upregulated. This upregulation can be detected in both the kidney tissue and in urine. Accordingly, provided herein are methods of diagnosing, prognosing, and treating kidney fibrosis and/or chronic kidney disease. As used herein, "kidney fibrosis" also called renal fibrosis, is the formation of excess fibrous connective tissue in kidney characterized by glomerulosclerosis and tubulointerstitial fibrosis. The pathogenesis of kidney fibrosis is a monotonous process that is characterized by an excessive accumulation and deposition of extracellular matrix (ECM) components (see e.g., Y. Liu, Kidney International 2006, 69, 213-217). Kidney fibrosis can be evaluated by methods including, but not limited to, histology, immunohistochemistry, Western blot, and real-time PCR for mRNA and protein expression of extracellular matrix including collagen I and alpha-smooth muscle actin, and activation of TGF beta/Smad signaling. Kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulonephritis, mesangiocapillary GN. Since kidney fibrosis is associated with loss of blood vessels, this results in secondary ischemia which can also result in glomerulare disease with loss of glomerular function. Regardless of the primary cause, insults to the kidneys may result in kidney fibrosis and the concomitant loss of kidney function. (Schena, F. and Gesualdo, L., *Pathogenic Mechanisms of Diabetic Nephropathy, J. Am. Soc. Nephrol.*, 16: S30-33 (2005); Whaley-Connell, A., and Sower, J R., *Chronic Kidney Disease and the Cardiometabolic Syndrome, J. Clin. Hypert.*, 8(8): 546-48 (2006)).

Kidney fibrosis has three stages which are inflammation reaction stage, formation of fibrosis stage and cicatricial stage respectively. Symptoms vary depending on the stage. There are no obvious symptoms in the inflammation reaction stage. In the formation stage, symptoms occur such as frequent night urine, high potassium, high blood pressure and itchy skin and so on. In the cicatricial stage, renal failure may occur.

In some embodiments, the subject treated, diagnosed, or prognosed in accordance with the various aspects described herein can be a subject having, diagnosed as having, or in need of treatment for a condition associated with kidney fibrosis. As used herein, the term "condition(s) associated with kidney fibrosis" refers to any condition having kidney fibrosis as a symptom or cause of the condition, or a condition that can be worsened by the development of kidney fibrosis, or a condition the progression of which is linked to the progression of kidney fibrosis. A condition associated with kidney fibrosis can therefore benefit therapeutically by inhibiting kidney fibrosis. Conditions associated with kidney fibrosis include, but are not limited to, diabetic nephropathy, chronic kidney disease, end-stage renal disease, systemic lupus erythematosis, vasculitis, IgA nephropathy, other autoimmune diseases, paraprotein diseases, diabetes. Since chronic kidney disease associated with kidney fibrosis is a very important risk factor for cardiovascular disease, it would be apparent to a skilled artisan that a therapeutic that prevented or reduced kidney fibrosis would have a beneficial effect on cardiac and vascular disease throughout the body. A condition associated with kidney fibrosis, including kidney fibrosis itself can be diagnosed by a blood test that measures the level of waste products such as creatinine and urea, a urine test that looks for abnormalities, a test that measures the level of expression of a gene described herein, an imaging test using ultrasound to assess kidney's structure and size, or a kidney biopsy.

In some embodiments, the kidney fibrosis can be chronic kidney fibrosis.

As used herein, "chronic kidney disease" or "CKD" refers to the progressive loss of kidney function over time. In some embodiments, CKD may include but is not limited to hyperphosphatemia (i.e., for example, >4.6 mg/dl) or low glomerular filtration rates (i.e., for example, <90 ml/minute per 1.73 m2 of body surface). However, many CKD patients may have normal serum phosphate levels in conjunction with a sustained reduction in glomerular filtration rate for 3 or more months, or a normal GFR in conjunction with sustained evidence of a structural abnormality of the kidney. In some embodiments, a subject with CKD can be a subject with either i) a sustained reduction in GFR <60 mi/min per 1.73 m2 of body surface for 3 or more months; or ii) a structural or functional abnormality of renal function for 3 or more months even in the absence of a reduced GFR. Structural or anatomical abnormalities of the kidney could be defined as but not limited to persistent microalbuminuria or proteinuria or hematuria or presence of renal cysts. Common symptoms of chronic kidney disease include tiredness, nausea, urine-like odor to the breath, bone pain, abnormally dark or light skin, itching, restless leg syndrome, blood in stools, bruising easily, pedal edema, and peripheral edema. Chronic kidney disease can be diagnosed through, e.g., medical history, a blood test that measures complete blood count, BUN level, or creatinine level, renal flow and scan, and renal ultrasound.

In one aspect, provided herein is a method of treating kidney fibrosis and/or chronic kidney disease, the method comprising; administering a therapeutically effective amount of a kidney fibrosis treatment to a subject determined have a level of expression of at least one gene selected from Table 4 that is increased relative to a reference level. In one aspect, provided herein is a method of treatment for kidney fibrosis and/or chronic kidney disease comprising; measuring a level of expression of at least one gene selected from Table 4 in a test sample obtained from a subject; treating the subject with a kidney fibrosis treatment when the expression level is increased relative to a reference level.

In certain embodiments, the assays and methods are directed to determination and/or measurement of the expression level of a gene product (e.g. protein and/or gene transcript such as mRNA) in a biological sample of a subject. Expression products can comprise expression products which have been subjected to post-translational modification and/or partial breakdown.

In certain embodiments the assays and methods are directed to determination of the expression level of a gene product of at least two genes in a biological sample of a subject, i.e. at least two genes, at least three genes, at least four genes, at least five genes, at least six genes, at least seven genes, at least eight genes, at least nine genes, at least 10 genes . . . at least 15 genes, . . . at least 25 genes, . . . at least 30 genes, or more genes, or any number of genes selected from Table 5 as described herein. In some embodiments, the at least one gene is selected from the genes listed in bold font in Table 5. In some embodiments, the expression level of at least two genes selected from Table 5 are measured. In some embodiments, the expression level of at least three genes selected from Table 5 are measured. In some embodiments, the expression level of at least four genes selected from Table 5 are measured. In some embodiments, the expression level of at least five genes selected from Table 5 are measured. In some embodiments, the expression level of at least six genes selected from Table 5 are measured. In some embodiments, the expression level of at least seven genes selected from Table 5 are measured.

The gene names listed in Table 5 are common names. NCBI Gene ID numbers are provided for each of the human genes listed in Table 5. Other genes, e.g. homologs may be obtained using the UCSC genome browser (available on the World Wide Web at http://genome.ucsc.edu) using the Gene Sorter function.

Table 5
Gene Symbol NCBI Gene ID
Adamts16 170690
Ccl2 6347
Ccl6 --
Ccl15 6359

Ccl9 --
Ccr2 729230
Cdh11 1009
Cldn3 1365
Col3a1 1281
Col8a1 1295
Cpn1 1369
Edn1 1906
Emr1 2015
Fn1 2335
Gabrp 2568
H2-Dmb1 --
HLA-DMB 3109
Itgam 3684
Lbp 3929
Lyz2 --
LYZ 4069
Mgp 4256
Mmp7 4316
Mrc1 4360
Nfam1 150372
Npy6r 4888
Pdpn 10630
Pld4 122618
Pltp 5360
Scn7a 6332
Sema3d 223117
Serpine2 5270
Smoc2 64094
Stra6 64220
Sytl2 54843
Tnc 3371
Tyrobp 7305

In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the assays, methods, and systems described herein are directed to determination of the expression level of a gene product of at least two genes in a biological sample of a subject, e.g. at least two genes, or at least three genes, or at least four genes, or at least five genes, or at least six genes, or at least seven genes, or at least eight genes, or at least nine genes, or at least ten genes, or at least eleven genes or, e.g. all of the following genes: Cdh11; Gabrp; Mgp; Pld4; Smoc2; Mrc1; Sytl2; Stra6; Scn7a; Sema3d; Pdpn; and Pltp.

In some embodiments, the at least one gene is selected from the group consisting of: Cdh11; Gabrp; Mgp; Pld4; Smoc2; Mrc1; Sytl2; Stra6; Scn7a; and Pltp. In some embodiments, the assays, methods, and systems described herein are directed to determination of the expression level of a gene product of at least two genes in a biological sample of a subject, e.g. at least two genes, or at least three genes, or at least four genes, or at least five genes, or at least six genes, or at least seven genes, or at least eight genes, or at least nine genes, or, e.g. all of the following genes: Cdh11; Gabrp; Mgp; Pld4; Smoc2; Mrc1; Sytl2; Strat6; Scn7a; and Pltp.

In some embodiments, the at least one gene is selected from the group consisting of: Cdh11; Mrc1; Pltp; Smoc2 and MGP. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: Cdh11; Mrc1; Pltp; Smoc2 and MGP. In some embodiments, the test sample is a urine sample and the at least one gene is selected from the group consisting of: Cdh11; Mrc1; Pltp; Smoc2 and MGP. In some embodiments, the assays, methods, and systems described herein are directed to determination of the expression level of a gene product of at least two genes in a biological sample of a subject, e.g. at least two genes, or at least three genes, or at least four genes, or, e.g. all of the following genes: Cdh11; Mrc1; Pltp; Smoc2 and MGP wherein the test sample is a urine sample.

In some embodiments, the at least one gene is selected from the group consisting of: Cdh11; Mrc1; and Pltp. In some embodiments, the assays, methods, and systems described herein are directed to determination of the expression level of a gene product of at least two genes in a biological sample of a subject, e.g. at least two genes, or, e.g. all of the following genes: Cdh11; Mrc1; and Pltp. In some embodiments, the test sample is a urine sample and the at least one gene is selected from the group consisting of: Cdh11; Mrc1; and Pltp. In some embodiments, the assays, methods, and systems described herein are directed to determination of the expression level of a gene product of at least two genes in a biological sample of a subject, e.g. at least two genes, or, e.g. all of the following genes: Cdh11; Mrc1; and Pltp wherein the test sample is a urine sample.

In some embodiments, the at least one gene is selected from the group consisting of: Cdh11; and Mrc1. In some embodiments, the assays, methods, and systems described herein are directed to determination of the expression level of a gene product of at least two genes in a biological sample of a subject, e.g. both of the following genes: Cdh11; and Mrc1. In some embodiments, the test sample is a urine sample and the at least one gene is selected from the group consisting of: Cdh11; and Mrc1. In some embodiments, the assays, methods, and systems described herein are directed to determination of the expression level of a gene product of at least two genes in a biological sample of a subject, e.g. both of the following genes: Cdh11; Mrc1; and Pltp wherein the test sample is a urine sample.

In some embodiments, the expression level of two or more genes selected from Table 5 can be determined, e.g., two genes, three genes, or more genes. Exemplary, non-limiting examples of suitable combinations of two genes are shown in Table 10.

TABLE 10

Exemplary pair-wise combinations of marker genes marked with an "X".
Cdh11; Gabrp; Mgp; Pld4; Smoc2; Mrc1; Sytl2; Stra6; Scn7a; Sema3d; Pdpn; and Pltp

|       | Cdh11 | Gabrp | Mgp | Pld4 | Smoc2 | Mrc1 | Sytl2 | Stra6 | Scn7a | Sema3d | Pdpn | Pltp |
|-------|-------|-------|-----|------|-------|------|-------|-------|-------|--------|------|------|
| Cdh11 |       | X     | X   | X    | X     | X    | X     | X     | X     | X      | X    | X    |
| Gabrp | X     |       | X   | X    | X     | X    | X     | X     | X     | X      | X    | X    |
| Mgp   | X     | X     |     | X    | X     | X    | X     | X     | X     | X      | X    | X    |
| Pld4  | X     | X     | X   |      | X     | X    | X     | X     | X     | X      | X    | X    |
| Smoc2 | X     | X     | X   | X    |       | X    | X     | X     | X     | X      | X    | X    |

TABLE 10-continued

Exemplary pair-wise combinations of marker genes marked with an "X".
Cdh11; Gabrp; Mgp; Pld4; Smoc2; Mrc1; Sytl2; Stra6; Scn7a; Sema3d; Pdpn; and Pltp

|        | Cdh11 | Gabrp | Mgp | Pld4 | Smoc2 | Mrc1 | Sytl2 | Stra6 | Scn7a | Sema3d | Pdpn | Pltp |
|--------|-------|-------|-----|------|-------|------|-------|-------|-------|--------|------|------|
| Mrc1   | X     | X     | X   | X    | X     |      | X     | X     | X     | X      | X    | X    |
| Sytl2  | X     | X     | X   | X    | X     | X    |       | X     | X     | X      | X    | X    |
| Stra6  | X     | X     | X   | X    | X     | X    | X     |       | X     | X      | X    | X    |
| Scn7a  | X     | X     | X   | X    | X     | X    | X     | X     |       | X      | X    | X    |
| Sema3d | X     | X     | X   | X    | X     | X    | X     | X     | X     |        | X    | X    |
| Pdpn   | X     | X     | X   | X    | X     | X    | X     | X     | X     | X      |      | X    |
| Pltp   | X     | X     | X   | X    | X     | X    | X     | X     | X     | X      | X    |      |

In some embodiments, measurement of the level of an expression product can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

Transformation, measurement, and/or detection of a target molecule, e.g. a mRNA or polypeptide can comprise contacting a sample obtained from a subject with a reagent (e.g. a detection reagent) which is specific for the target, e.g., a target molecule-specific reagent. In some embodiments, the target-specific reagent is detectably labeled. In some embodiments, the target-specific reagent is capable of generating a detectable signal. In some embodiments, the target-specific reagent generates a detectable signal when the target molecule is present.

Methods to measure gene expression products are well known to a skilled artisan. Such methods to measure gene expression products, e.g., protein level, include ELISA (enzyme linked immunosorbent assay), western blot, immunoprecipitation, and immunofluorescence using detection reagents such as an antibody or protein binding agents. Alternatively, a peptide can be detected in a subject by introducing into a subject a labeled anti-peptide antibody and other types of detection agent. For example, the antibody can be labeled with a detectable marker whose presence and location in the subject is detected by standard imaging techniques.

For example, antibodies for Cdh11 are commercially available and can be used for the purposes of the invention to measure protein expression levels, e.g. anti-Cdh11 (Cat. No. SAB4500033; Sigma Aldrich, St. Louis, Mo.). Alternatively, since the amino acid sequences for Cdh11 are known and publically available at NCBI website, one of skill in the art can raise their own antibodies against these polypeptides of interest for the purpose of the invention.

The amino acid sequences of the polypeptides described herein, e.g. Cdh11 have been assigned NCBI accession numbers for different species such as human, mouse and rat.

In some embodiments, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change of color, upon encountering the targeted molecules. In some instances, signal amplification can be integrated into the particular protocol, wherein a secondary antibody, that includes the marker stain or marker signal, follows the application of a primary specific antibody.

In some embodiments, the assay can be a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay (RIA), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays (CLIA), electrochemiluminescence immunoassay (ECLIA, counting immunoassay (CIA), lateral flow tests or immunoassay (LFIA), magnetic immunoassay (MIA), and protein A immunoassays. Methods for performing such assays are known in the art, provided an appropriate antibody reagent is available. In some embodiment, the immunoassay can be a quantitative or a semi-quantitative immunoassay.

An immunoassay is a biochemical test that measures the concentration of a substance in a biological sample, typically a fluid sample such as urine, using the interaction of an antibody or antibodies to its antigen. The assay takes advantage of the highly specific binding of an antibody with its antigen. For the methods and assays described herein, specific binding of the target polypeptides with respective proteins or protein fragments, or an isolated peptide, or a fusion protein described herein occurs in the immunoassay to form a target protein/peptide complex. The complex is then detected by a variety of methods known in the art. An immunoassay also often involves the use of a detection antibody.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries.

In one embodiment, an ELISA involving at least one antibody with specificity for the particular desired antigen (e.g., Cdh11 as described herein) can also be performed. A known amount of sample and/or antigen is immobilized on a solid support (usually a polystyrene micro titer plate). Immobilization can be either non-specific (e.g., by adsorption to the surface) or specific (e.g. where another antibody immobilized on the surface is used to capture antigen or a primary antibody). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified antibodies that are directed against a target polypeptide or fragment thereof are coated on the solid phase of multi-well plate, i.e., conjugated to a solid surface. A second batch of purified antibodies that are not conjugated on any solid support is also needed. These non-conjugated purified antibodies are labeled for detection purposes, for example, labeled with horseradish peroxidase to produce a detectable signal. A sample (e.g., a blood sample) from a subject is mixed with a known amount of desired antigen (e.g., a known volume or concentration of a sample comprising a target polypeptide) together with the horseradish peroxidase labeled antibodies and the mixture is then are added to coated wells to form competitive combination. After incubation, if the polypeptide level is high in the sample, a complex of labeled antibody reagent-antigen will form. This complex is free in solution and can be washed away. Washing the wells will remove the complex. Then the wells are incubated with TMB (3, 3', 5, 5'-tetramethylbenzidene) color development substrate for localization of horseradish peroxidase-conjugated antibodies in the wells. There will be no color change or little color change if the target polypeptide level is high in the sample. If there is little or no target polypeptide present in the sample, a different complex in formed, the complex of solid support bound antibody reagents-target polypeptide. This complex is immobilized on the plate and is not washed away in the wash step. Subsequent incubation with TMB will produce much color change. Such a competitive ELSA test is specific, sensitive, reproducible and easy to operate.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; and Oellerich, M. 1984, J. Clin. Chem. Clin. Biochem. 22:895-904. These references are hereby incorporated by reference in their entirety.

In one embodiment, the levels of a polypeptide in a sample can be detected by a lateral flow immunoassay test (LFIA), also known as the immunochromatographic assay, or strip test. LFIAs are a simple device intended to detect the presence (or absence) of antigen, e.g. a polypeptide, in a fluid sample. There are currently many LFIA tests are used for medical diagnostics either for home testing, point of care testing, or laboratory use. LFIA tests are a form of immunoassay in which the test sample flows along a solid substrate via capillary action. After the sample is applied to the test strip it encounters a colored reagent (generally comprising antibody specific for the test target antigen) bound to microparticles which mixes with the sample and transits the substrate encountering lines or zones which have been pretreated with another antibody or antigen. Depending upon the level of target polypeptides present in the sample the colored reagent can be captured and become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water, and/or homogenized tissue samples etc. Strip tests are also known as dip stick test, the name bearing from the literal action of "dipping" the test strip into a fluid sample to be tested. LFIA strip tests are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibodies raised to the target antigen. The test line will also contain antibodies to the same target, although it may bind to a different epitope on the antigen. The test line will show as a colored band in positive samples. In some embodiments, the lateral flow immunoassay can be a double antibody sandwich assay, a competitive assay, a quantitative assay or variations thereof. Competitive LFIAs are similar to competitive ELISA. The sample first encounters colored particles which are labeled with the target antigen or an analogue. The test line contains antibodies to the target/its analogue. Unlabelled antigen in the sample will block the binding sites on the antibodies preventing uptake of the colored particles. The test line will show as a colored band in negative samples. There are a number of variations on lateral flow technology. It is also possible to apply multiple capture zones to create a multiplex test.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Examples of patents that describe the use of "dip stick" technology to detect soluble antigens via immunochemical assays include, but are not limited to U.S. Pat. Nos. 4,444,880; 4,305,924; and 4,135,884; which are incorporated by reference herein in their entireties. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teachings of this "dip stick" technology for the detection of polypeptides using antibody reagents as described herein.

Other techniques can be used to detect the level of a polypeptide in a sample. One such technique is the dot blot, and adaptation of Western blotting (Towbin et at., Proc. Nat. Acad. Sci. 76:4350 (1979)). In a Western blot, the polypeptide or fragment thereof can be dissociated with detergents and heat, and separated on an SDS-PAGE gel before being transferred to a solid support, such as a nitrocellulose or PVDF membrane. The membrane is incubated with an antibody reagent specific for the target polypeptide or a fragment thereof. The membrane is then washed to remove unbound proteins and proteins with non-specific binding. Detectably labeled enzyme-linked secondary or detection antibodies can then be used to detect and assess the amount of polypeptide in the sample tested. The intensity of the signal from the detectable label corresponds to the amount of enzyme present, and therefore the amount of polypeptide. Levels can be quantified, for example by densitometry.

In some embodiments, the level of, e.g., Cdh11, can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy and/or immunoelectrophoresis assay.

In some embodiments, the level of an expression product can be determined by mass spectrometry based Multiple Reaction Monitoring (MRM) assay or selected reaction monitoring (SRM) assay.

In certain embodiments, the gene expression products as described herein can be instead determined by determining the level of messenger RNA (mRNA) expression of the genes described herein, e.g. Cdh11. Such molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNA protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the genes described herein, e.g., Cdh11, have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylene diaminetetraacetic acid (EDTA).

A level which is more than a reference level can be a level which is more by at least about 10%, at least about 20%, at least about 50%, at least about 600%, at least about 80%, at least about 90%, at least about 100%, at least about 200%, at least about 300%, at least about 500% or more than the reference level. In some embodiments, a level which is more than a reference level can be a level which is statistically significantly more than the reference level. In some embodiments, the reference can be a level of the expression product in a population of subjects who do not have or are not diagnosed as having, and/or do not exhibit signs or symptoms of kidney fibrosis and/or CKD. In some embodiments, the reference can also be a level of expression of the expression product in a control sample, a pooled sample of control individuals or a numeric value or range of values based on the same. In some embodiments, the reference can be the level of the expression product in a sample obtained from the same subject at an earlier point in time, e.g., the methods described herein can be used to determine if a subject's risk or likelihood of developing kidney fibrosis and/or CKD is increasing.

In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined In some embodiments of the foregoing aspects, the expression level of a given gene, can be normalized relative to the expression level of one or more reference genes or reference proteins.

The term "sample" or "test sample" as used herein denotes a sample taken or isolated from a biological organism, e.g., a blood, plasma, or urine sample from a subject. Exemplary biological samples include, but are not limited to, a biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, the test sample can be a urine sample.

The test sample can be obtained by removing a sample from a subject, but can also be accomplished by using previously sample (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the method and/or assay described herein can further comprising depleting the sample of abundant proteins prior to the measuring step. In some embodiments, the depletion step comprises affinity chromatography. Thus, for example, immunodepletion can be conducted, e.g., the sample is depleted or fractionated to remove abundant proteins known to be present in the particular sample, e.g. proteins not listed in Table 5, e.g. such as by use of immunodepletion with appropriate antibodies. In some embodiments series of subtractions and/or depletions can performed.

In some embodiments, the methods, assays, and systems described herein can further comprise a step of obtaining a test sample from a subject. In some embodiments, the subject can be a human subject. In some embodiments, the subject can be a subject in need of treatment for (e.g. having or diagnosed as having) Diabetes; hypertension; acute kidney injury; chronic kidney disease; an autoimmune disease (e.g. systemic lupus erythematosus); renal transplant rejection; renal or systemic infections (e.g. streptococcal infections, bacterial endocarditis, human immunodeficiency virus, hepatitis B, C); and inflammatory or infiltrative disease (e.g. membranoproliferative glomerulonephritis, IgA nephropathy); chemical toxicity poisoning (e.g. drugs, toxins, metals); mechanical damage affecting the kidneys; renal ischemia (e.g. microangiopathies, renal artery occlusion, renal atheroembolism, renal vein thrombosis); obstruction of the urinary tract (e.g. nephrolithiasis); primary genetic alterations (e.g. polycystic kidney disease); and idiopathic chronic kidney disease.

In one aspect, described herein is an assay comprising: measuring the expression level of at least one gene selected from Table 4 in a test sample obtained from a subject; wherein an increase in the expression level of at least one gene selected from Table 4 relative to a reference level indicates the subject has a higher risk of having or developing kidney fibrosis and/or chronic kidney disease. In one aspect, described herein is a method of identifying a subject in need of treatment for kidney fibrosis and/or chronic kidney disease, the method comprising: measuring the level of expression of at least one gene selected from Table 4 in a test sample obtained from a subject; and identifying the subject as being in need of treatment for kidney fibrosis and/or chronic kidney disease when the expression level in the sample is increased relative to a reference level. In one aspect, described herein is a method of determining if a subject is at risk for kidney fibrosis and/or chronic kidney disease, the method comprising: providing a sample obtained from the subject; measuring the level of expression of at least one gene selected from Table 4 in a test sample obtained from a subject; comparing the expression level in the sample to a reference expression level; determining that the subject is at risk for kidney fibrosis and/or chronic kidney disease when the expression level in the sample is increased relative to a reference level; and determining that the subject is not at risk for kidney fibrosis and/or chronic kidney disease when the expression level in the sample is not increased relative to a reference level.

In one aspect, described herein is a method of determining the efficacy of a treatment for kidney fibrosis and/or chronic kidney disease, the method comprising: (a) measuring a level of expression of at least one gene selected from Table 4 in a test sample obtained from a subject before administration of a candidate treatment; (b) measuring the level of expression of the at least one gene in a test sample obtained from a subject after administration of the candidate treatment; and (c) determining that the candidate treatment is efficacious when the expression level determined in step (b) is decreased relative to the expression level determined in step (a). The subject administered the candidate treatment can have been previously treated with the same or different treatments, e.g. established and/or candidate treatments (e.g., the subject need not be naïve to treatment for kidney fibrosis and/or chronic kidney disease prior to performing step (a)).

In some embodiments of any of the aspects described herein, the method and/or assay can further comprise administering a treatment for kidney fibrosis and/or chronic kidney disease. Treatments for kidney fibrosis and/or chronic kidney disease are known in the art and include, by way of non-limiting example, dialysis; transplant; low protein diet; an ACE inhibitor (e.g. perindopril, captopril, enalapril, lisinopril, or ramipril); an angiotensin II receptor blocker (ARB) (e.g., Losartan, irbesartan, olmesartan, candesartan, valsartan, fimasartan, or telmisartan); lipid control (e.g., statins); D-vitamin supplementation; phosphate control; anemia control (e.g., erythroid stimulating agents); acidosis prevention (e.g., sodium bicarbonate); and uric acid control (e.g., allopurinol).

In some embodiments, a treatment for kidney fibrosis and/or chronic kidney disease can comprise administering a therapeutically effective amount of an antagonist or agonist of at least one gene selected from Table 4. In one aspect, provided herein is a method of treating kidney fibrosis and/or chronic kidney disease, the method comprising administering an antagonist or agonist of at least one gene selected from Table 4. In one aspect, provided herein is the use of an antagonist or agonist of at least one gene selected from Table 4, the use comprising administering the antagonist or agonist to a subject in need of treatment for kidney fibrosis and/or chronic kidney disease. In some embodiments, the at least one gene is selected from the group consisting of: Cdh11; Gabrp; Mgp; Pld4; Smoc2; Mrc1; Sytl2; Stra6; Scn7a; Sema3d; Pdpn; and Pltp. In some embodiments, the at least one gene is selected from the group consisting of Cdh11; Gabrp; Mgp; Pld4; Smoc2; Mrc1; Sytl2; Stra6; Scn7a; and Pltp. In some embodiments, the at least one gene is selected from the group consisting of: Cdh11; Mrc1; Pltp; Smoc2 and MGP. In some embodiments, the at least one gene is selected from the group consisting of: Cdh11; Mrc1; and Pltp. In some embodiments, the at least one gene is selected from the group consisting of Cdh11 and Mrc1. In some embodiments, the kidney fibrosis is chronic progressive fibrosis.

In some embodiments, the subject is administered an antagonist of a gene selected from Table 4. As used herein, "antagonist" or "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of a given target, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RTPCR with primers can be used to determine the level of RNA and Western blotting with an antibody can be used to determine the level of a polypeptide. In some embodiments, the inhibitor can be an inhibitory nucleic acid; an aptamer; an antibody reagent; an antibody; or a small molecule.

In some embodiments, the subject is administered an agonist of a gene selected from Table 4.

As used herein, the term "agonist" refers to any agent that increases the level and/or activity of the target, e.g, of Cdh11. As used herein, the term "agonist" refers to an agent which increases the expression and/or activity of the target by at least 10% or more, e.g. by 10% or more, 50% or more, 100% or more, 200% or more, 500% or more, or 1000% or more. Non-limiting examples of agonists of a given target gene can include polypeptides encoded by the gene or fragments thereof and nucleic acids encoding a such polypeptides, e.g. a polypeptide comprising the sequence of a Cdh11 expression product or a nucleic acid encoding such a polypeptide or variants thereof.

The compositions and methods described herein can be administered to a subject having or diagnosed as having kidney fibrosis and/or CDK. In some embodiments, the methods described herein comprise administering an effective amount of compositions described herein, e.g. an inhibitor of a gene of Table 5 to a subject in order to alleviate a symptom of kidney fibrosis and/or CDK. As used herein, "alleviating a symptom" of kidney fibrosis and/or CDK is ameliorating any condition or symptom associated with the kidney fibrosis and/or CDK. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of an agent needed to alleviate at least one or more symptom of the disease or disorder, and relates to a sufficient amount of pharmacological composition to provide the desired effect. The term "therapeutically effective amount" therefore refers to an amount of the agent that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for kidney function among others. The dosage can be determined by a physician and adjusted, as necessary, to suit observed effects of the treatment.

In some embodiments, the technology described herein relates to a pharmaceutical composition comprising an inhibitor of a gene selected from Table 5 as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition comprising an inhibitor of a gene selected from Table 5 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of agents as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent as disclosed herein can also be incorporated into the parenteral dosage forms of the disclosure, including conventional and controlled-release parenteral dosage forms.

Pharmaceutical compositions comprising an inhibitor of a gene selected from Table 5 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the agent can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment are described elsewhere herein.

In certain embodiments, an effective dose of a composition comprising an agent as described herein can be administered to a patient once. In certain embodiments, an effective dose of a composition comprising an agent can be administered to a patient repeatedly. For systemic administration, subjects can be administered a therapeutic amount of a composition such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. of kidney fibrosis by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of an inhibitor of a gene selected from Table 5 according to the methods described herein depend upon, for example, the form of the inhibitor, its potency, and the extent to which symptoms, markers, or indicators of a condition described herein are desired to be reduced, for example the percentage reduction desired for a symptom. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agent in, e.g. the treatment of a condition described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. kidney function. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of kidney fibrosis. When using an experimental animal model, efficacy of treatment is evidenced when a statistically significant change in a marker is observed.

In vitro and animal model assays are provided herein which allow the assessment of a given dose of an inhibitor of a gene selected from Table 5. By way of non-limiting example, the effects of a dose of an inhibitor can be assessed by measuring the level of an expression product of the targeted gene.

The efficacy of a given dosage combination can also be assessed in an animal model, e.g. a mouse model of kidney fibrosis as described in the examples herein.

In some embodiments, described herein is a kit for the detection of an expression product of at least one gene selected from Table 5 in a sample, the kit comprising at least a first target-specific reagent as described herein which specifically binds the selected expression product, on a solid support and comprising a detectable label. The kits described herein include reagents and/or components that permit assaying the level of an expression product in a sample obtained from a subject (e.g., a biological sample obtained from a subject). The kits described herein can optionally comprise additional components useful for performing the methods and assays described herein.

A kit can further comprise devices and/or reagents for concentrating an expression product (e.g, a polypeptide) in a sample, e.g. a urine sample. Thus, ultrafiltration devices permitting, e.g., protein concentration from plasma can also be included as a kit component.

Preferably, a diagnostic or prognostic kit for use with the methods and assays disclosed herein contains detection reagents for expression products. Such detection reagents comprise in addition to target-specific reagents, for example, buffer solutions, labels or washing liquids etc. Furthermore, the kit can comprise an amount of a known nucleic acid and/or polypeptide, which can be used for a calibration of the kit or as an internal control. A diagnostic kit for the detection of an expression product can also comprise accessory ingredients like secondary affinity ligands, e.g., secondary antibodies, detection dyes and any other suitable compound or liquid necessary for the performance of a expression product detection method known to the person skilled in the art. Such ingredients are known to the person skilled in the art and may vary depending on the detection method carried out. Additionally, the kit may comprise an instruction leaflet and/or may provide information as to the relevance of the obtained results.

In some aspects, the invention described herein is directed to systems (and computer readable media for causing computer systems) for obtaining data from at least one sample obtained from at least one subject, the system comprising 1) a measuring module configured to receive the at least one sample and perform at least one analysis on the at least one sample to determine the level and/or activity of at least one expression product selected from Table 5 in the sample; 2) a storage device configured to store data output from the determination module; and 3) a display module for displaying a content based in part on the data output from the determination module, wherein the content comprises a signal indicative of the level of the at least one expression product.

Figure 10:
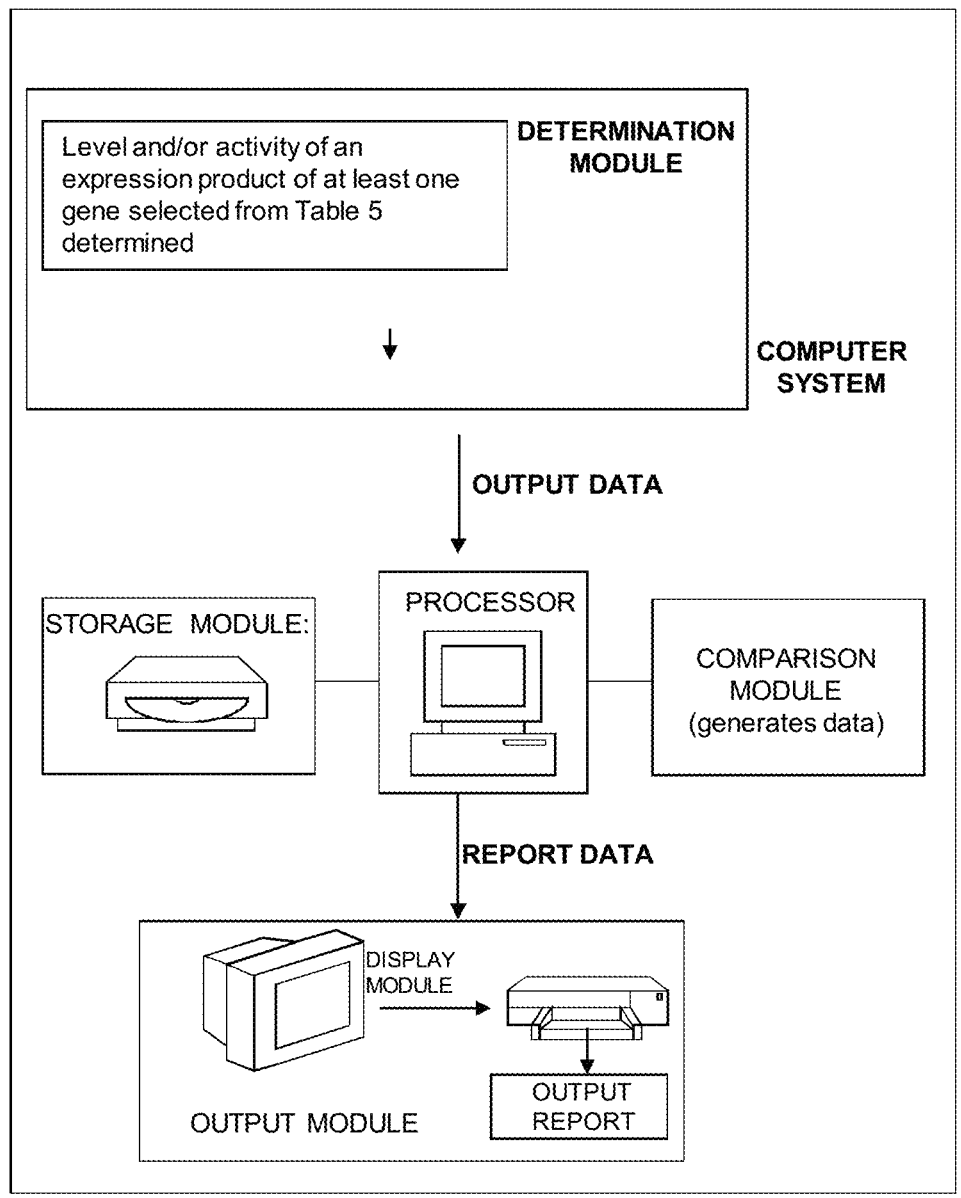
FIG. 10 is a diagram of an exemplary embodiment of a system for performing an assay for determining the level an expression product of at least one gene selected from Table 5 in a sample obtained from a subject.

In one embodiment, provided herein is a system comprising: (a) at least one memory containing at least one computer program adapted to control the operation of the computer system to implement a method that includes a measuring module configured to measure the level of at least one expression product in a test sample obtained from a subject; a storage module configured to store output data from the determination module; a comparison module adapted to compare the data stored on the storage module with a reference level, and to provide a retrieved content, and a display module for displaying whether the sample comprises a level of an expression product which is significantly increased relative to the reference expression level and/or displaying the relative level of the expression product and (b) at least one processor for executing the computer program (see FIG. 10).

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; a tablet; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J #, Visual Basic, C, C #, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of expression products etc in computer readable form.

The measuring module can comprise any system for detecting a signal elicited from an assay to determine the level of an expression product described above herein. In some embodiments, such systems can include an instrument, e.g., AU2700 (Beckman Coulter Brea, Calif.) as described herein for quantitative measurement of polypeptides or e.g., a real time PCR machine, e.g. a LIGHTCYCLER™ (Roche). In some embodiments, the measuring module can measure the intensity of a detectable signal from an assay indicating the level of polypeptide in the test sample. In some embodiments, the assay can be an immunoassay. In some embodiments, the measuring module can measure the intensity of a detectable signal from a RT-PCR assay indicating the level of RNA transcript in the test sample.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the determination module. In additional embodiments, the storage module stores reference information such as levels of at least one expression product in healthy subjects and/or a population of healthy subjects.

Figure 11:
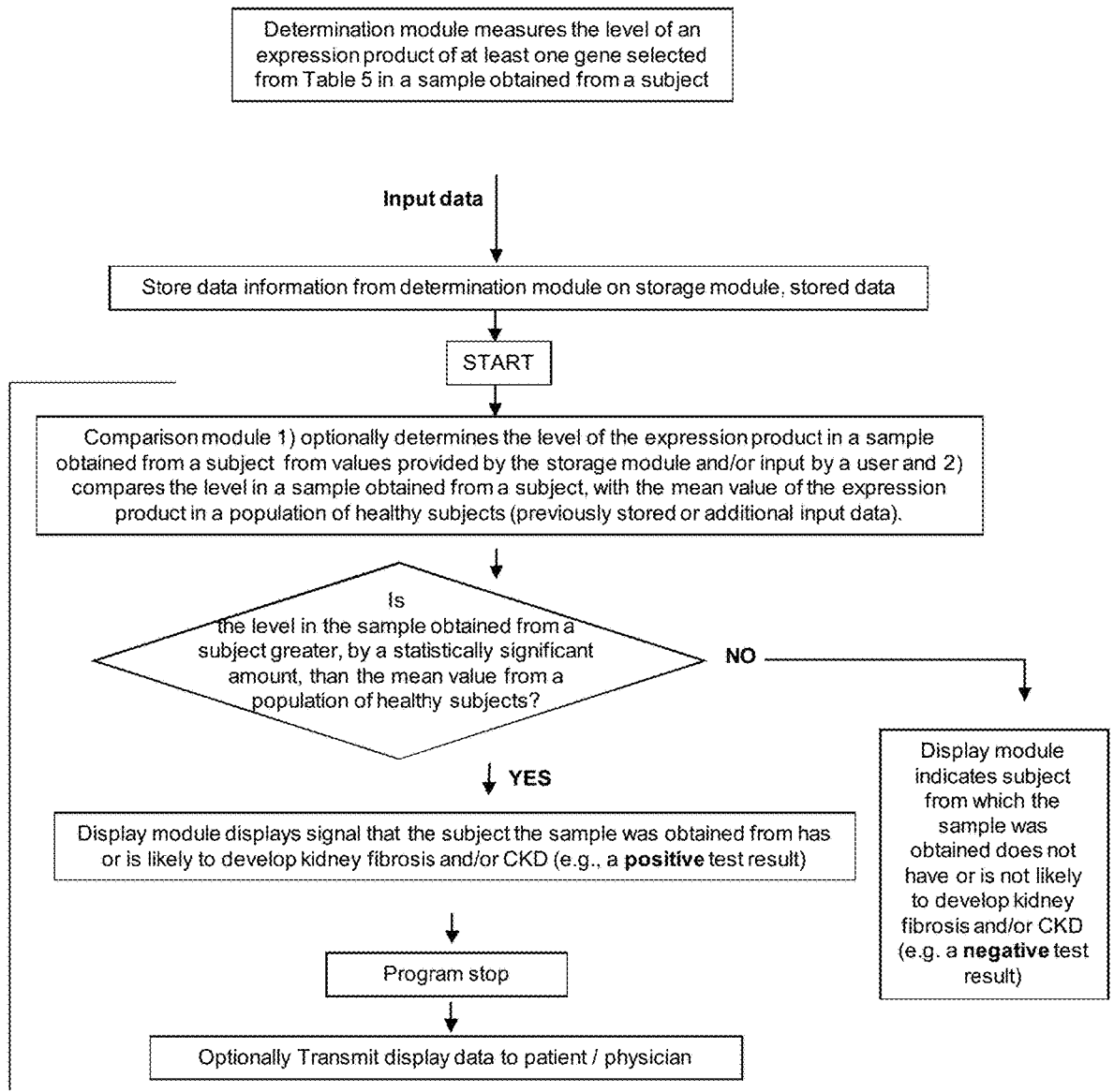
FIG. 11 is a diagram of an exemplary embodiment of a comparison module as described herein.

The "computing module" can use a variety of available software programs and formats for computing the level of an expression product. Such algorithms are well established in the art. A skilled artisan is readily able to determine the appropriate algorithms based on the size and quality of the sample and type of data. The data analysis tools and equations described herein can be implemented in the computing module of the invention. In one embodiment, the computing module further comprises a comparison module, which compares the level of an expression product in a sample obtained from a subject as described herein with the mean value of the expression product in a population of healthy subjects (FIG. 11). By way of an example, when the value of the expression product in a sample obtained from a subject is measured, a comparison module can compare or match the output data with the mean value of the expression product in a population of healthy subjects. In certain embodiments, the mean value of the expression product in a population of healthy subjects can be pre-stored in the storage module. In various embodiments, the comparison module can be configured using existing commercially-available or freely-available software for comparison purpose, and may be optimized for particular data comparisons that are conducted.

Figure 12:
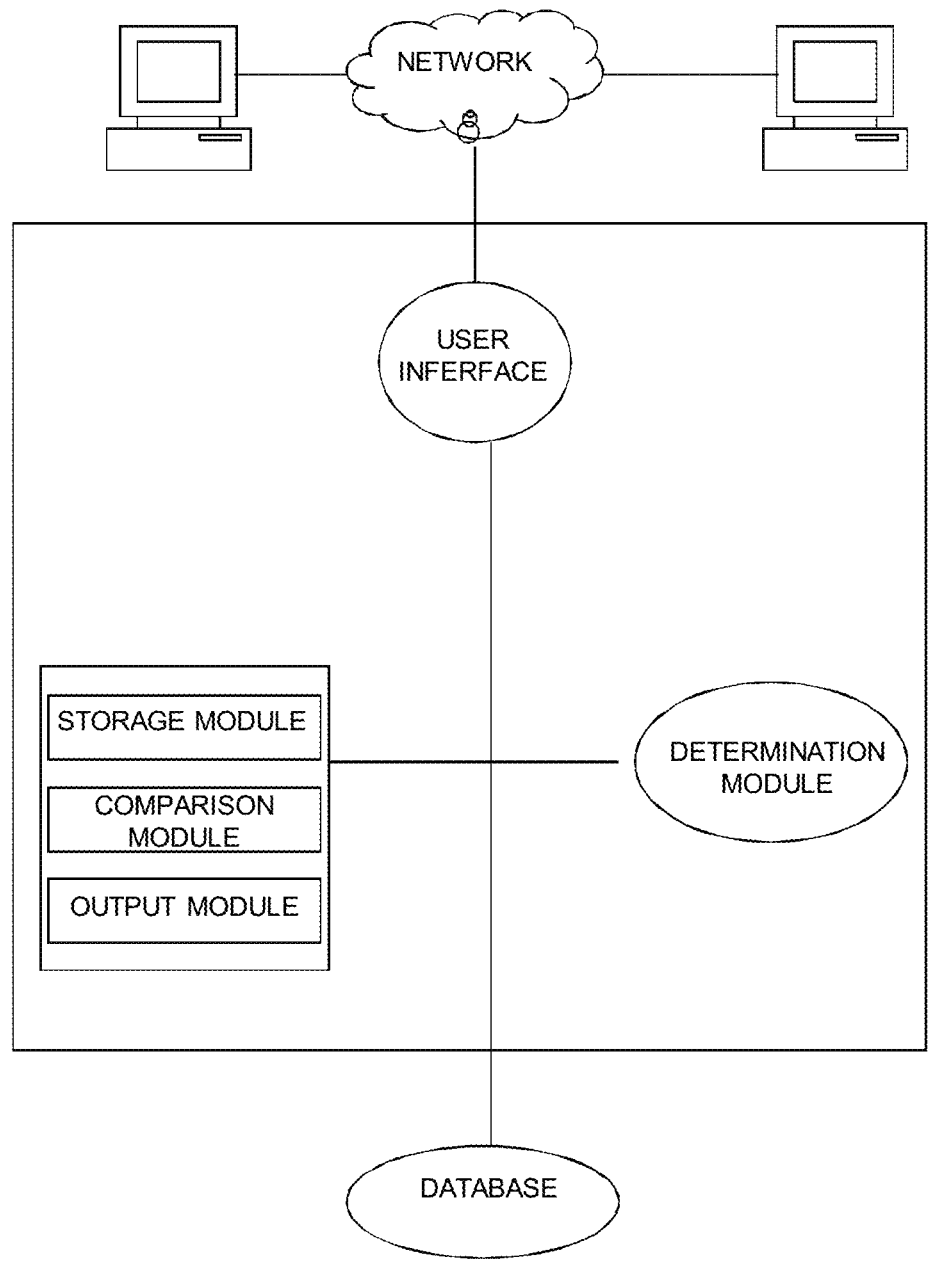
FIG. 12 is a diagram of an exemplary embodiment of an operating system and applications for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 12).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be the level of an expression product in the sample obtained from a subject. In some embodiments, the content displayed on the display module can be the relative level of the expression product in the sample obtained from a subject as compared to the mean level of the expression product in a population of healthy subjects. In some embodiments, if the computing module determines that the level of the expression product in the test sample obtained from a subject is more by a statistically significant amount than the reference level, the display module displays a signal indicating that the levels in the sample obtained from a subject are more than those of the reference level. In some embodiments, the signal indicates the subject is in need of treatment for kidney fibrosis and/or CKD. In some embodiments, the signal indicates the degree to which the level of the expression product in the sample obtained from a subject varies from the reference level. In some embodiments, the content displayed on the display module can indicate whether the subject has an increased likelihood of having or developing kidney fibrosis and/or CKD. In some embodiments, the content displayed on the display module can be a numerical value indicating one of these risks or probabilities. In such embodiments, the probability can be expressed in percentages or a fraction. For example, higher percentage or a fraction closer to 1 indicates a higher likelihood of a subject having or developing kidney fibrosis and/or CKD. In some embodiments, the content displayed on the display module can be single word or phrases to qualitatively indicate a risk or probability. For example, a word "unlikely" can be used to indicate a lower risk for having or developing kidney fibrosis and/or CKD, while "likely" can be used to indicate a high risk for having or developing kidney fibrosis and/or CKD.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level and/or activity of a gene in a sample obtained from a subject, and therefore are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of kidney fibrosis and/or CKD. A subject can be male or female.

A subject can be one who has been previously diagnosed with or identified as suffering from or having a condition in need of treatment (e.g. kidney fibrosis and/or CKD) or one or more complications related to such a condition, and optionally, have already undergone treatment for kidney fibrosis and/or CKD or the one or more complications related to kidney fibrosis and/or CKD. Alternatively, a subject can also be one who has not been previously diagnosed as having kidney fibrosis and/or CKD or one or more complications related to kidney fibrosis and/or CKD. For example, a subject can be one who exhibits one or more risk factors for kidney fibrosis and/or CKD or one or more complications related to kidney fibrosis and/or CKD or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, a particular "polypeptide", e.g. a Cdh11 polypeptide can include the human polypeptide; as well as homologs from other species, including but not limited to bovine, dog, cat chicken, murine, rat, porcine, ovine, turkey, horse, fish, baboon and other primates. The terms also refer to fragments or variants of the native polypeptide that maintain at least 50% of the activity or effect of the native full length polypeptide, e.g. as measured in an appropriate animal model. Conservative substitution variants that maintain the activity of wildtype polypeptides will include a conservative substitution as defined herein. The identification of amino acids most likely to be tolerant of conservative substitution while maintaining at least 50% of the activity of the wildtype is guided by, for example, sequence alignment with homologs or paralogs from other species. Amino acids that are identical between homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model of allograft rejection as described herein.

In some embodiments, a polypeptide can be a variant of a sequence described herein. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., at least 50% of the wildtype reference protein. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or note, has more than 100% of the activity of wildtype, e.g. 110%, 125%, 150%, 175%, 200%, 500%, 1000% or more.

One method of identifying amino acid residues which can be substituted is to align, for example, the human polypeptide to a homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide as described herein, e.g., an inhibitory antibody reagent administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an NLRX1 polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. a an antibody reagent, can be modified, e.g. by addition of a moiety to one or more of the amino acids comprising the peptide. In some embodiments, a polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG or albumin.

In some embodiments, a polypeptide or nucleic acid administered to the subject can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (*Gene* 42:133, 1986); Bauer et al. (*Gene* 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a polypeptide as described herein can be chemically synthesized and mutations can be incorporated as part of the chemical synthesis process.

In some embodiments, a polypeptide, e.g., a antibody reagent, as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in Transport Processes in Pharmaceutical Systems, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), which are incorporated by reference herein in their entireties.

In some embodiments, a polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid, e.g. an inhibitory nucleic acid as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, an inhibitor of a gene expression product of a gene described herein (e.g. Cdh11) can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of the targeted mRNA transcript. The use of these iRNAs permits the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of, e.g., Cdh11. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.), 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216, 141; 5,235,033; 5,64,562; 5,264,564; 5,405,938; 5,434,257;

5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments include RNAs with phosphorothioate backbones and oligonucleosides with heteroatom backbones, and in particular —CH$_2$—NH—CH$_2$—, —CH$_2$—N(CH$_3$)—O—CH$_2$—[known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$—[wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Exemplary suitable modifications include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, dsRNAs include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e 2'-O—CH$_2$—O—CH$_2$—N(CH$_3$)$_2$, also described in examples herein below.

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA as described herein involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In some embodiments, a nucleic acid encoding an inhibitory nucleic acid as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and $CH_1$ domains; (ii) a F(ab')2 fragment, a bivalent fragment including two Fab fragments linked by a disulfide bridge at the hinge region; (iii) an Fd fragment consisting of the VH and $CH_1$ domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to e.g., Cdh11.

As used herein, "expression level" refers to the number of mRNA molecules and/or polypeptide molecules encoded by a given gene that are present in a cell or sample. Expression levels can be increased or decreased relative to a reference level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. kidney fibrosis and/or CKD. The term "treating" includes reducing or alleviating at least one adverse effect or symptom of a condition, disease or disorder associated with kidney fibrosis and/or CKD. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., (ISBN 0-632-02182-9); Benjamin Lewin, Genes X, published by Jones & Bartlett Publishing, 2009 (ISBN-10: 0763766321); Kendrew et al. (eds.), and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating kidney fibrosis and/or chronic kidney disease, the method comprising;
   administering a therapeutically effective amount of a kidney fibrosis treatment to a subject determined have a level of expression of at least one gene selected from Table 5 that is increased relative to a reference level.

2. A method of treatment for kidney fibrosis and/or chronic kidney disease comprising;
   measuring a level of expression of at least one gene selected from Table 5 in a test sample obtained from a subject;
   treating the subject with a kidney fibrosis treatment when the expression level is increased relative to a reference level.

3. The method of any of paragraphs 1-2, wherein the kidney fibrosis treatment is selected from the group consisting of:
   dialysis; transplant; low protein diet; an ACE inhibitor; an angiotensin II receptor blocker (ARB); lipid control (e.g., statins); D-vitamin supplementation; phosphate control; anemia control (e.g., erythroid stimulating agents); acidosis prevention (e.g., sodium bicarbonate); and uric acid control (e.g., allopurinol).

4. An assay comprising:
   measuring the expression level of at least one gene selected from Table 5 in a test sample obtained from a subject;
   wherein an increase in the expression level of at least one gene selected from Table 5 relative to a reference level indicates the subject has a higher risk of having or developing kidney fibrosis and/or chronic kidney disease.

5. A method of identifying a subject in need of treatment for kidney fibrosis and/or chronic kidney disease, the method comprising:

measuring the level of expression of at least one gene selected from Table 5 in a test sample obtained from a subject; and identifying the subject as being in need of treatment for kidney fibrosis and/or chronic kidney disease when the expression level in the sample is increased relative to a reference level.

6. A method of determining if a subject is at risk for kidney fibrosis and/or chronic kidney disease, the method comprising:

providing a sample obtained from the subject;

measuring the level of expression of at least one gene selected from Table 5 in a test sample obtained from a subject;

comparing the expression level in the sample to a reference expression level;

determining that the subject is at risk for kidney fibrosis and/or chronic kidney disease when the expression level in the sample is increased relative to a reference level; and determining that the subject is not at risk for kidney fibrosis and/or chronic kidney disease when the expression level in the sample is not increased relative to a reference level.

7. A method of determining the efficacy of a treatment for kidney fibrosis and/or chronic kidney disease, the method comprising:

(a) measuring a level of expression of at least one gene selected from Table 5 in a test sample obtained from a subject before administration of the treatment;

(b) measuring the level of expression of the at least one gene in a test sample obtained from a subject after administration of the treatment; and (c) determining that the treatment is efficacious when the expression level determined in step (b) is decreased relative to the expression level determined in step (a).

8. The assay and/or method of any of paragraphs 1-7, wherein the test sample is a urine sample.

9. The assay and/or method of any of paragraphs 1-8, wherein the at least one gene is selected from the group consisting of:

Cdh11; Gabrp; Mgp; Pld4; Smoc2; Mrc1; Sytl2; Strat6; Scn7a; Sema3d; Pdpn; and Pltp.

10. The assay and/or method of any of paragraphs 1-9, wherein the at least one gene is selected from the group consisting of:

Cdh11; Gabrp; Mgp; Pld4; Smoc2; Mrc1; Sytl2; Strat6; Scn7a; and Pltp.

11. The assay and/or method of any of paragraphs 1-10, wherein the at least one gene is selected from the group consisting of:

Cdh11; Mrc1; Pltp; Smoc2 and MGP.

12. The assay and/or method of paragraph 11, wherein the at least one gene is selected from the group consisting of:

Cdh11; Mrc1; and Pltp.

13. The assay and/or method of any of paragraphs 1-10, wherein the test sample is a urine sample and the at least one protein is selected from the group consisting of:

Cdh11; Mrc1; Pltp; Smoc2 and MGP.

14. The assay and/or method of paragraph 13, wherein the test sample is a urine sample and the at least one gene is selected from the group consisting of:

Cdh11; Mrc1; and Pltp.

15. The assay and/or method of any of paragraphs 1-14, wherein the at least one gene is selected from the group consisting of:

Cdh11 and Mrc1.

16. The assay and/or method of any of paragraphs 1-15, wherein the kidney fibrosis is chronic progressive fibrosis.

17. The assay/method of any of paragraphs 1-16, wherein the expression level of the at least one gene selected from Table 5 is determined by measuring the level of a nucleic acid.

18. The assay/method of paragraph 17, wherein the expression level is measured by measuring the level of the gene's RNA transcript.

19. The assay/method of any of paragraphs 17-18, wherein the level of the nucleic acid is measured using a method selected from the group consisting of:

RT-PCR; quantitative RT-PCR; Northern blot; microarray based expression analysis; next-generation sequencing; and RNA in situ hybridization.

20. The assay/method of any of paragraphs 1-18, wherein the expression level of the at least one gene selected from Table 5 is measured by measuring the level of the gene's polypeptide expression product.

21. The assay/method of paragraph 19, wherein the level of the polypeptide is measured using a method selected from the group consisting of:

Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay.

22. The assay/method of any of paragraphs 20-21, wherein the polypeptide level is measured using immunochemistry.

23. The assay and/or method of any of paragraphs 1-22, wherein the measuring step comprises an ELISA assay; mass spectrometry based Multiple Reaction Monitoring (MRM) assay; or selected reaction monitoring (SRM) assay.

24. The assay and/or method of any of paragraphs 1-23, further comprising depleting the sample of abundant proteins prior to the measuring step.

25. The assay and/or method of paragraph 24, wherein the depletion step comprises affinity chromatography.

26. The assay/method of any of paragraphs 22-25, wherein the antibody reagent is detectably labeled or generates a detectable signal.

27. The assay/method of any of paragraphs 1-26, wherein the expression level of the at least one gene selected from Table 5 is normalized relative to the expression level of one or more reference genes or reference proteins.

28. The assay/method of any of paragraphs 1-27, wherein the reference level is the expression level of in a prior sample obtained from the subject.

29. The assay or method of any of paragraphs 1-28, wherein the expression level of at least two genes selected from Table 5 are measured.

30. The assay or method of any of paragraphs 1-28, wherein the expression level of at least three genes selected from Table 5 are measured.

31. The assay or method of any of paragraphs 1-28, wherein the expression level of at least four genes selected from Table 5 are measured.

32. The assay/method of any of paragraphs 1-31, wherein the subject is a subject with a condition selected from the group consisting of:
diabetes; hypertension; acute kidney injury; chronic kidney disease; an autoimmune disease (e.g. systemic lupus erythematosus); renal transplant rejection; renal or systemic infections (e.g. streptococcal infections, bacterial endocarditis, human immunodeficiency virus, hepatitis B, C); and inflammatory or infiltrative disease (e.g. membranoproliferative glomerulonephritis, IgA nephropathy); chemical toxicity poisoning (e.g. drugs, toxins, metals); mechanical damage affecting the kidneys; renal ischemia (e.g. microangiopathies, renal artery occlusion, renal atheroembolism, renal vein thrombosis); obstruction of the urinary tract (e.g. nephrolithiasis); primary genetic alterations (e.g. polycystic kidney disease); and idiopathic chronic kidney disease.

33. The assay/method of any of paragraphs 1-32, further comprising the step of administering a treatment for kidney fibrosis.

34. The assay or method of paragraph 33, wherein the treatment comprises administering an antagonist or agonist of at least one gene selected from Table 5.

35. The assay or method of paragraph 34, wherein the at least one gene is selected from the group consisting of:
Cdh11; Gabrp; Mgp; Pld4; Smoc2; Mrc1; Sytl2; Stra6; Scn7a; Sema3d; Pdpn; and Pltp.

36. The assay or method of any of paragraphs 34-35, wherein the at least one gene is selected from the group consisting of:
Cdh11; Gabrp; Mgp; Pld4; Smoc2; Mrc1; Sytl2; Stra6; Scn7a; and Pltp.

37. The assay or method of any of paragraphs 34-36, wherein the at least one gene is selected from the group consisting of:
Cdh11; Mrc1; Pltp; Smoc2 and MGP.

38. The assay or method of any of paragraphs 34-37, wherein the at least one gene is selected from the group consisting of:
Cdh11; Mrc1; and Pltp.

39. The assay or method of any of paragraphs 34-38, wherein the at least one gene is selected from the group consisting of:
Cdh11 and Mrc1.

40. A kit for performing the method/assay of any of paragraphs 1-39.

41. A method of treating kidney fibrosis and/or chronic kidney disease, the method comprising administering an antagonist or agonist of at least one gene selected from Table 5.

42. The method of paragraph 41, wherein the at least one gene is selected from the group consisting of:
Cdh11; Gabrp; Mgp; Pld4; Smoc2; Mrc1; Sytl2; Stra6; Scn7a; Sema3d; Pdpn; and Pltp.

43. The method of any of paragraphs 41-42, wherein the at least one gene is selected from the group consisting of:
Cdh11; Gabrp; Mgp; Pld4; Smoc2; Mrc1; Sytl2; Stra6; Scn7a; and Pltp.

44. The method of any of paragraphs 41-43, wherein the at least one gene is selected from the group consisting of:
Cdh11; Mrc1; Pltp; Smoc2 and MGP.

45. The method of any of paragraphs 41-44, wherein the at least one gene is selected from the group consisting of:
Cdh11; Mrc1; and Pltp.

46. The method of any of paragraphs 41-45, wherein the at least one gene is selected from the group consisting of:
Cdh11 and Mrc1.

47. The method of any of paragraphs 41-46, wherein the kidney fibrosis is chronic progressive fibrosis.

48. The method of any of paragraphs 41-47, wherein the antagonist is selected from the group consisting of:
an inhibitory nucleic acid; an aptamer; an antibody reagent; an antibody; and a small molecule.

49. The use of an antagonist or agonist of at least one gene selected from Table 5, the use comprising administering the antagonist or agonist to a subject in need of treatment for kidney fibrosis and/or chronic kidney disease.

50. The use of paragraph 49, wherein the at least one gene is selected from the group consisting of:
Cdh11; Gabrp; Mgp; Pld4; Smoc2; Mrc1; Sytl2; Stra6; Scn7a; Sema3d; Pdpn; and Pltp.

51. The use of any of paragraphs 49-50, wherein the at least one gene is selected from the group consisting of:
Cdh11; Gabrp; Mgp; Pld4; Smoc2; Mrc1; Sytl2; Stra6; Scn7a; and Pltp.

52. The use of any of paragraphs 49-51, wherein the at least one gene is selected from the group consisting of:
Cdh11; Mrc1; Pltp; Smoc2 and MGP.

53. The use of any of paragraphs 49-52, wherein the at least one gene is selected from the group consisting of:
Cdh11; Mrc1; and Pltp.

54. The use of any of paragraphs 49-53, wherein the at least one gene is selected from the group consisting of:
Cdh11 and Mrc1.

55. The use of any of paragraphs 49-54, wherein the kidney fibrosis is chronic progressive fibrosis.

56. The use of any of paragraphs 49-55, wherein the antagonist is selected from the group consisting of:
an inhibitory nucleic acid; an aptamer; an antibody reagent; an antibody; and a small molecule.

EXAMPLES

Example 1

Chronic kidney disease (CKD) has reached global epidemic levels and more than 20 millions U.S. adults currently live with it, many of them not diagnosed. The current biomarkers for detecting and monitoring the progression of CKD, estimation of glomerular filtration rate (eGFR) and measurement of protein/albumin in the urine lack sensitivity and specificity and show alterations only when a significant amount of structural damage has already happened. Earlier and better biomarkers will allow improved detection of CKD development but also the preservation of kidney function for a longer duration even while using the current limited treatment arsenal. Additionally they could improve patient stratification in clinical trials and provide more precise surrogate end-points.

Described herein is the identification of biomarkers and therapeutics for CKD that detect the condition early and accurately as well as predict its progression and response to therapy. Using the mouse model of folic acid (FA) induced nephropathy that progresses within 14 days to kidney fibrosis, the hallmark pathological finding of CKD, and the RNA-seq technique we identified herein are 12 genes (Cdh11, Gabrp, Mgp, Pld4, Smoc2, Mrc1, Sytl2, Strat6, Scn7a, Sema3d, Pdpn, Pltp) with increasing expression in the kidney that tracks chronic progressive fibrosis.

Many of these genes are also hypothesized to be in the causal pathway of fibrosis and can therefore serve as therapeutic targets. The upregulated expression of these 12 candidate genes was confirmed in 2 additional mouse models (unilateral ureteral obstruction and unilateral ischemia/reperfusion –1/R), while low expression was registered in 2 models of acute kidney injury (cisplatin nephrotoxicity and bilateral I/R) attesting to their specificity towards kidney fibrosis. Increased protein expression in fibrotic kidneys was confirmed by immunofluorescence for a first group of 10 of these genes in FA treated mice and CKD patients. Using western blot, Cdh11, Gabrp, Mgp, Pld4, and Smoc2 were also shown to be present in the urine of a CKD patient while virtually absent in that of a healthy volunteer. Similar steps are taken to test the kidney protein expression and urinary presence of the remaining candidates.

These proteins can be measured in biological samples to specifically identify patients with CKD earlier than currently used measurements, predict the response to therapy, measure the risk to progress to a more advanced stage. In some embodiments, the measurements can utilize commercially available ELISA kits and mass spectrometry based Multiple Reaction Monitoring (MRM) assays.

It is contemplated herein that the expression of these genes can vary in response to therapy or worsening of the fibrotic condition.

By employing a comprehensive analysis of kidney gene expression (both in terms of time-points in the process of progressing from a normal kidney to tubulointerstitial fibrosis as well as complete coverage of transcriptome conferred by RNA-seq) identified herein are 12 genes that were for the most part not known to be associated with kidney fibrosis/chronic kidney disease. Their gene expression was comprehensively tested in animal models of kidney injury and protein detection confirmation performed in human kidney and the kidneys of human CKD patients. An important selection criterion was the location of the proteins, either trans-membrane or in the extracellular compartment, to increase the probability of the whole molecule or of fragments being released into urine by the damaged kidney. The 5 proteins tested so far are present in the urine of a CKD patient, a novel finding and an important characteristic for clinical measurements.

Cell based approaches and using molecular biology reagents to over express as well as knockdown 2 of the 12 proteins have yielded phenotypic changes in the fibroblasts indicating their critical role in fibrosis development.

Contemplated herein is ELISA based testing for single proteins or multiplexed assays for a panel of proteins, e.g., an MRM assay, to detect CKD at an early stage, particularly in at-risk groups like diabetic, hypertensive patients or patients that have survived an episode of acute kidney injury. These or different proteins/panels can then be used to closely monitor the progression of the disease in these patients and their response to therapy. The measurements of these proteins can additionally guide the selection, stratification of patients enrolled in clinical trials and the selection of endpoints in these situations. Finally, modulation of the gene expression can permit therapeutic approaches to CKD.

Example 2

Next Generation Sequencing Identifies CDH11 and MRC1 as Novel Translational Biomarkers of Kidney Fibrosis Chronic kidney disease (CKD) is the gradual, asymptomatic loss of kidney function and current tests only identify it when significant loss has already happened. Using RNA sequencing in a mouse model of folic acid (FA) induced nephropathy, identified herein are 10 genes that track kidney fibrosis development, the common pathological finding in CKD patients. The gene and protein expression of all 10 candidates was confirmed to be significantly high (~10-150 fold) in three well-established, mechanistically distinct mouse models of kidney fibrosis. Protein expression was also high in the FA model and in patients with biopsy-proven kidney fibrosis. The mRNA expression of the 10 genes increased with severity of kidney fibrosis, decreased in response to therapeutic intervention and demonstrated specificity by showing a very modest (~2-5 fold) increase following liver fibrosis in mice and humans. Using targeted selected reaction monitoring mass spectrometry (SRM-MS) it was found that 3 out of 10, cadherin 11 (CDH11), mannose receptor C1 (MRC1), phospholipid transfer protein (PLTP), were detectable in human urine. Furthermore, the levels of CDH11 and MRC1 were able to distinguish patients with CKD from healthy individuals ($p<0.05$). Described herein is the identification of CDH11 and MRC1 as novel non-invasive biomarkers of CKD.

Chronic kidney disease, the gradual degradation of renal excretory function, is increasingly recognized as a major public health problem, affecting 10 to 16% of the adult population globally (1), with approximately 26 million cases in the United States (2). The socio-economic impact of CKD is high, with 27.6% of total Medicare costs being used to treat it, third only to diabetes and heart failure (3). It is estimated that only approximately 11% of the patients with at least moderate decrease in kidney function eventually progress to kidney failure and become dependent on dialysis or transplantation treatments (4). But even the patients that do not progress are at increased risk of cardiovascular disease and death (5). The disease is usually asymptomatic until at least two thirds of the functional capacity of the kidneys is already lost (6) and most people are unaware they have it and are diagnosed only in late stages of CKD (2).

Current guidelines from the Kidney Disease Improving Global Outcome (KDIGO) CKD Work Group recommend the definition, classification and prognosis of CKD based on estimation of glomerular filtration rate (eGFR, using formulas that rely on serum creatinine measurements and cystatin C), and albuminuria (7). Due to renal compensatory mechanisms serum creatinine only shows alterations when more than half of the kidney function is already lost, and is also affected by many other factors like muscle mass, hydration, medications, age, gender. Similarly, significant renal damage is needed for measurable proteinuria or even microalbuminuria and protein in the urine is not detected when the cause of CKD is hypertension or tubulointerstitial disease (8). While new biomarkers are being proposed, many are still in early stages of testing and none are currently approved for clinical use (9). There still is a great need for new biomarkers in CKD to help diagnosis, prognosis and facilitate preclinical studies and clinical trials for the development of new, curative therapies. Ideally these biomarkers should reflect kidney pathology rather than generalized processes. Since fibrosis is the common histological finding in CKD patients (6) the objective of this study was to identify translational biomarkers of CKD using a mouse model of progression to kidney fibrosis induced by folic acid administration (10). Using RNA sequencing in the fibrotic kidneys identified and confirmed herein is the increased expression for a panel of 10 genes. Increased protein expression for these candidates was also confirmed in animal models and humans with kidney fibrosis. Also described herein are SRM assays for these 10 proteins and the report that 2 of them, CDH11 and MRC1, are significantly increased in the urines of CKD patients as compared to patients without kidney disease.

Results

Identification of Candidate Genes for Biomarkers of Kidney Fibrosis Through RNA-Seq.

Figure 7:
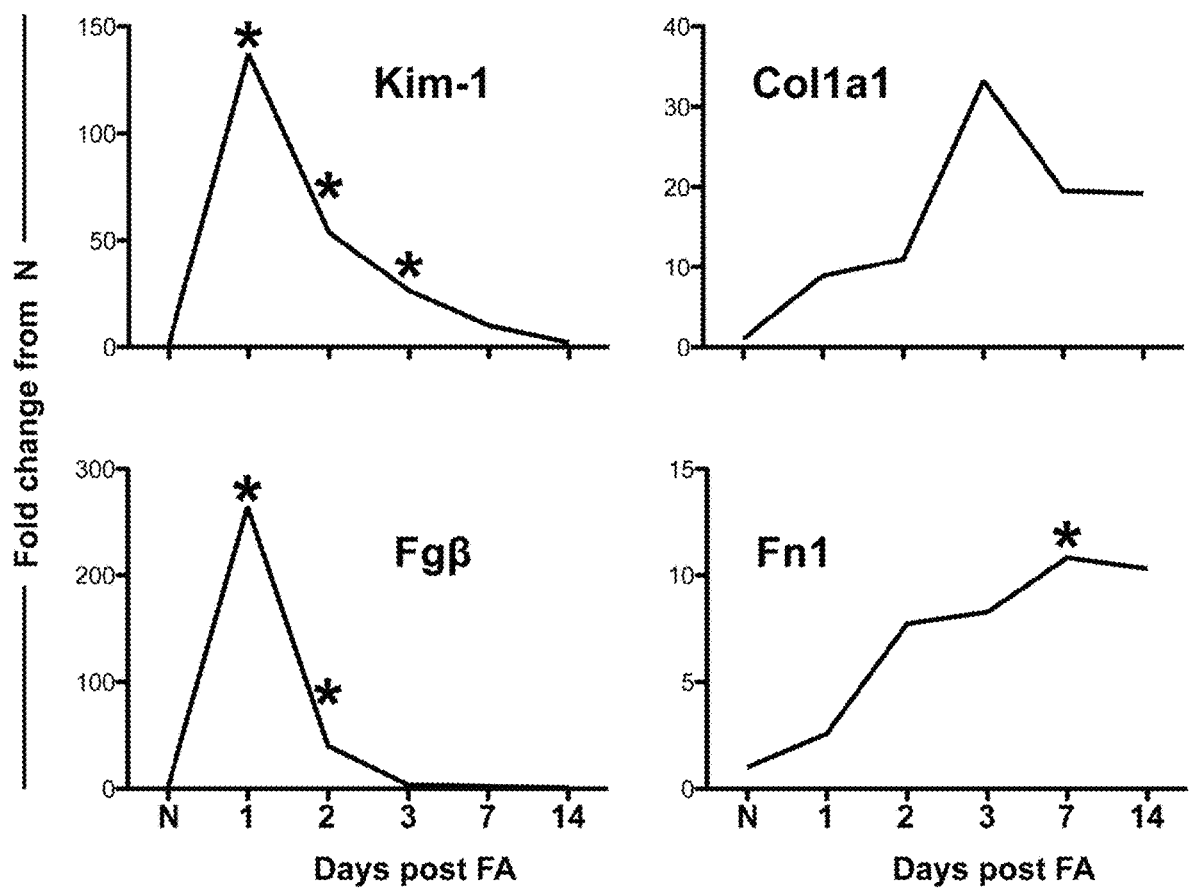
FIG. 7 demonstrates RNA-seq measurement of kidney gene expression for known markers of acute kidney injury (Kim-1, Fgβ) and kidney fibrosis (Col1a1, Fn1). Data is shown as the mean fold change from normal for the 3 samples included in RNA-seq at each time-point. * indicates time-points when p<0.2 for the fold change from normal.
Figure 8A:
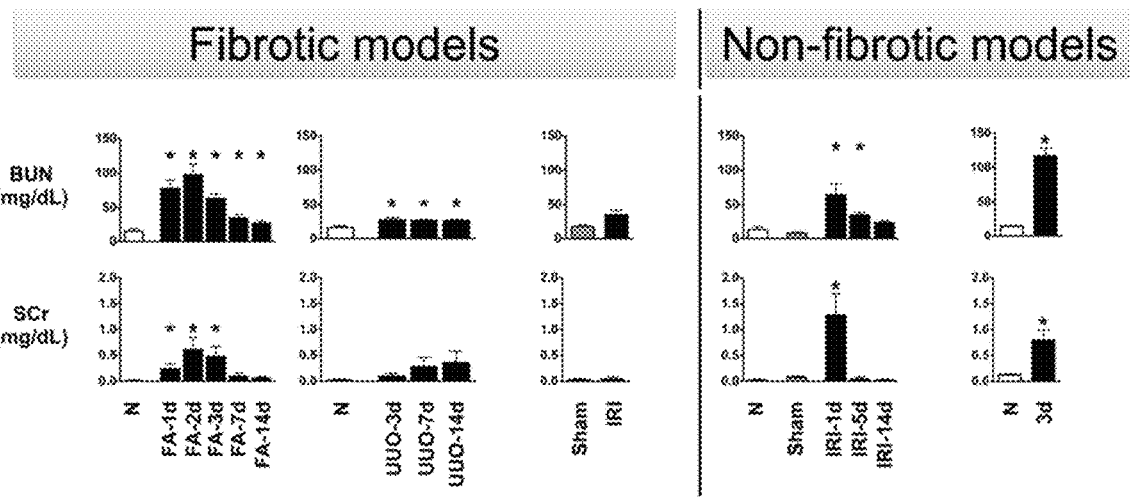
FIGS. 8A-8B demonstrate biochemical and molecular characteristics of mouse models of kidney fibrosis and acute kidney injury.
Figure 8B:
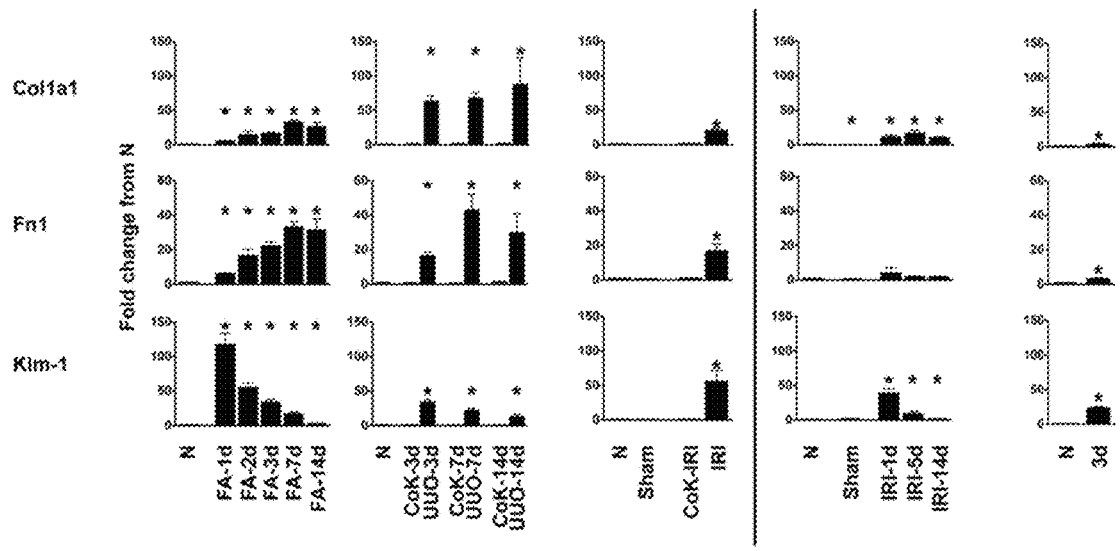

In order to identify differentially expressed genes in progressive kidney fibrosis, RNA sequencing (50 base pair, paired end) was performed in mouse kidneys obtained at days 0, 1, 2, 3, 7, and 14 after single intraperitoneal injection of 250 mg/kg folic acid (n=3/time point, FIG. 7). The validity of the RNA-seq experiment was verified through expression changes in predicted genes (10) at the appropriate time-points for acute injury (Kim-1, Fgβ) and fibrosis (Col1a1, Fn1) (FIGS. 8A-8B). Three hundred sixty seven genes showed significant changes from normal at least at one time-point when the expression in the injured/fibrotic kidneys was compared to normal for all time-points using DESeq analysis with a cut-of of $p<0.2$ (FIGS. 1A-1C, Table 1). Hierarchical clustering of data demonstrated a dynamic and temporal pattern of gene expression changes with a subset of genes showing differential expression during injury phase (days 1-3), with a return to normal for most by day 14; and another subset of genes showing up-regulation only as the kidneys progressed to fibrosis, particularly at days 7 and 14 (FIG. 1C). To select genes that are indicative of fibrosis candidates were considered from this later group that had robust upregulation (>5-fold with >100 read counts at peak) over time as fibrosis progresses. Another important criteria was the location of the protein product of the gene, either in extracellular matrix or transmembrane, to increase the chance of detecting it in the urine and use it as a biomarker (11). Ten candidates that fit the selection criteria were selected for further validation, with the individual temporal expression profiles from RNA-seq shown in FIG. 1D.

Confirmation of the 10 Candidate Genes in Mouse Models of Kidney Fibrosis.

Figure 9:
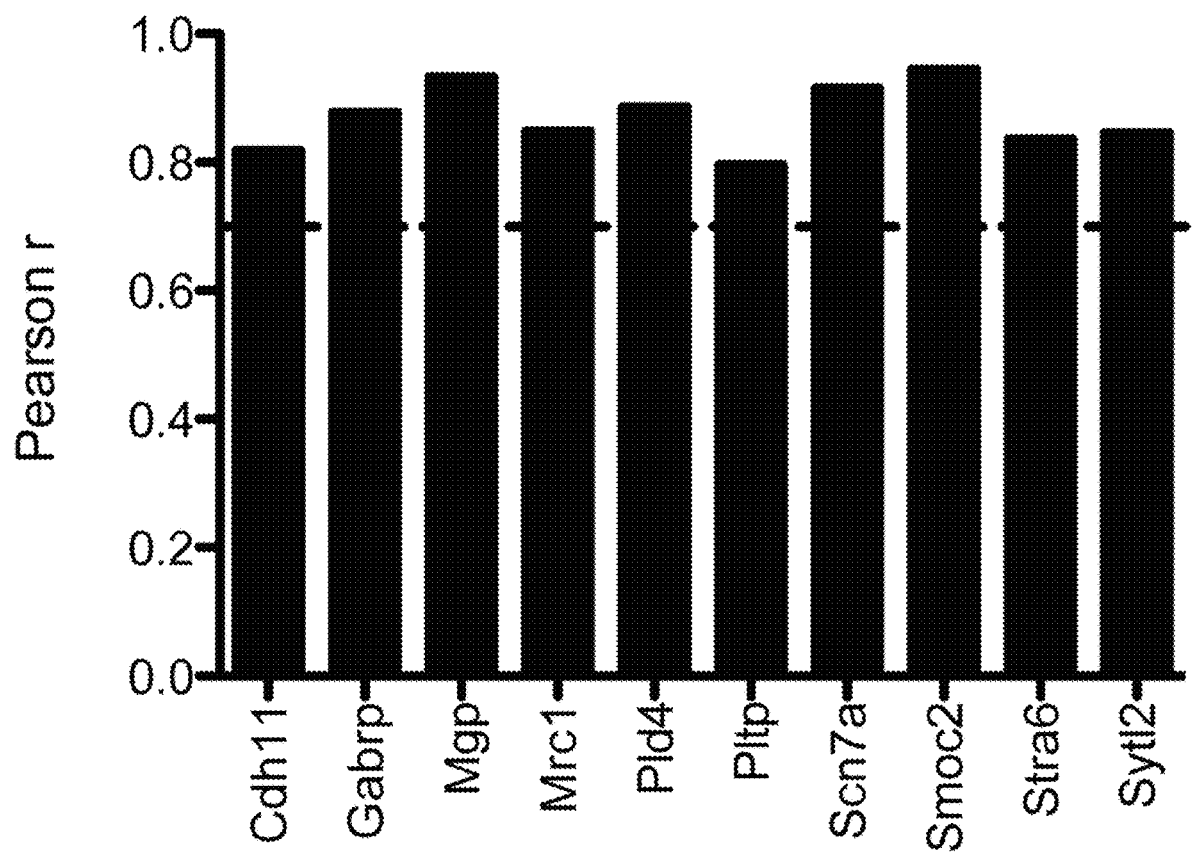
FIG. 9 demonstrates RNA-seq vs. qRT-PCR correlation of gene expression measurement for the 11 selected candidates. Pearson r correlation coefficients were calculated for all 18 measurements by the individual technique (3 samples×6 groups). Horizontal line at 0.7 indicates a good level of correlation.

To generalize the utility of the candidate genes as biomarkers of fibrosis irrespective of the animal model used and to further test if their expression associates more with fibrosis rather then acute kidney injury, qRT-PCR was performed for all the candidate genes in 3 well established and mechanistically distinct mouse models that result in kidney fibrosis as well as 2 that cause acute kidney injury (FIG. 7). The Pearson correlation coefficient between quantitative expression of the 10 candidate genes measured by RNA-seq and qRT-PCR was found to be above 0.7 for all, indicating a good correlation between techniques (FIG. 9). The mRNA expression of all 10 genes was significantly high (~10-150 fold compared to normal) in the kidneys of mice with developing fibrosis irrespective of whether it was initiated by folic acid administration (FA) or Unilateral Ureteral Obstruction (UUO) or Unilateral Ischemia Reperfusion Injury (Unil-IRI) (FIG. 2). Generally, expression was highest in UUO mice, which develop a more robust fibrotic phenotype encompassing the whole kidney rather then patchy fibrosis of the FA model (10), with Gabrp and Smoc2 reaching the highest levels following unilateral IRI. Very modest (less than 5-fold) increases in many of the genes were seen in acute kidney injury models. These results indicate that the kidney expression of these 10 genes is more robust for fibrosis development than for acute kidney injury.

Protein Expression of the Candidates after Kidney Fibrosis in Mice and Humans.

Figure 3:
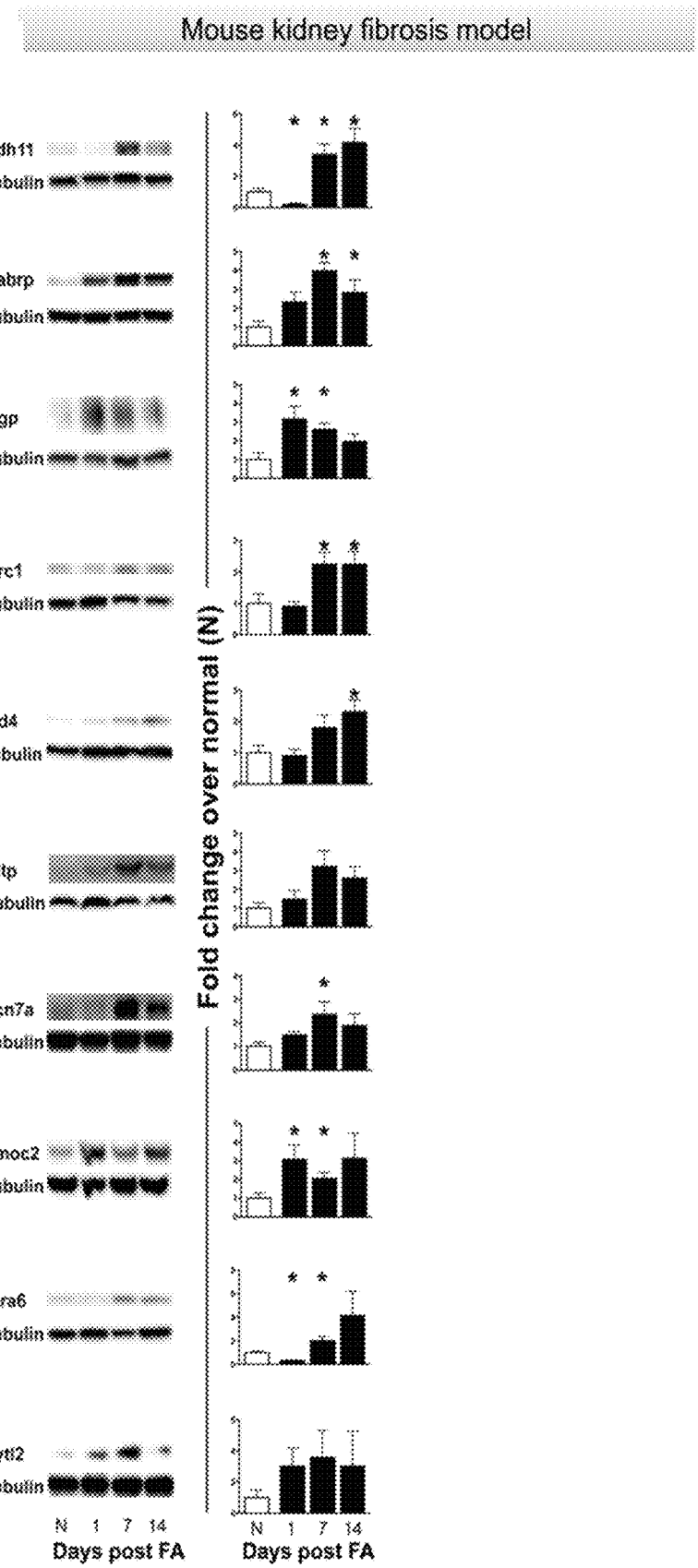
FIG. 3 demonstreates significantly increased protein expression for the 10 candidates in fibrotic kidney samples from mice. Protein levels were detected by immunoblot following folic acid (FA) injection in mice. Data was normalized to tubulin and is presented as mean±SEM of the fold change from Normal (N), n=5/group. *p<0.05 when compared to N.

To verify if increased gene expression translates into protein expression in fibrotic kidneys, which would leave open the possibility for these proteins or degradation fragments to reach urine where their permits their use as fibrosis biomarkers, they were tested by immunoblot in the mouse kidneys at various time-points in the fibrosis development in the FA model (FIG. 3). Representative immunofluorescence images demonstrated increased protein expression and localization in mouse fibrotic kidney samples at 14 days after FA injection when compared to normal. Increased protein expression was also detected in fibrotic human kidney tissue when compared to normal tissue (data not shown). Most of the proteins reached statistically significant ($p<0.05$) increased kidney expression at least at one time-point. The temporal profiles for protein expression generally matched those for gene expression for the FA model. Notable exceptions were MGP and SMOC2, with an earlier increase in protein expression than that for the gene expression (FIGS. 2 and 3). The peak fold change over normal for the protein expression was also generally lower than for the gene expression but this is expected considering that gene expression does not always translate stoichiometrically to protein expression. For a better picture of their increased expression and localization, immunofluorescence was performed in normal and fibrotic mouse kidneys (day 14 in the FA model). Increased presence for all proteins in the kidney, particularly in relation to the tubular structures was found (data not shown). To evaluate the expression pattern of these 10 genes in human kidneys, immunofluorescence staining was performed in human kidney tissues (n=5) that were severely fibrotic (80% fibrotic) and compared to normal human kidneys (less than 5% fibrosis) (data not shown). Representative pictures from a normal kidney and a fibrotic kidney show increased protein presence for the 10 candidates similar to what was found in the FA model, with a similar location pattern (data not shown and Table 6).

Response of Candidate Genes to Increased Severity or Therapeutic Reversibility of Fibrosis.

Figures 4A, 4B, 4C, 4D:
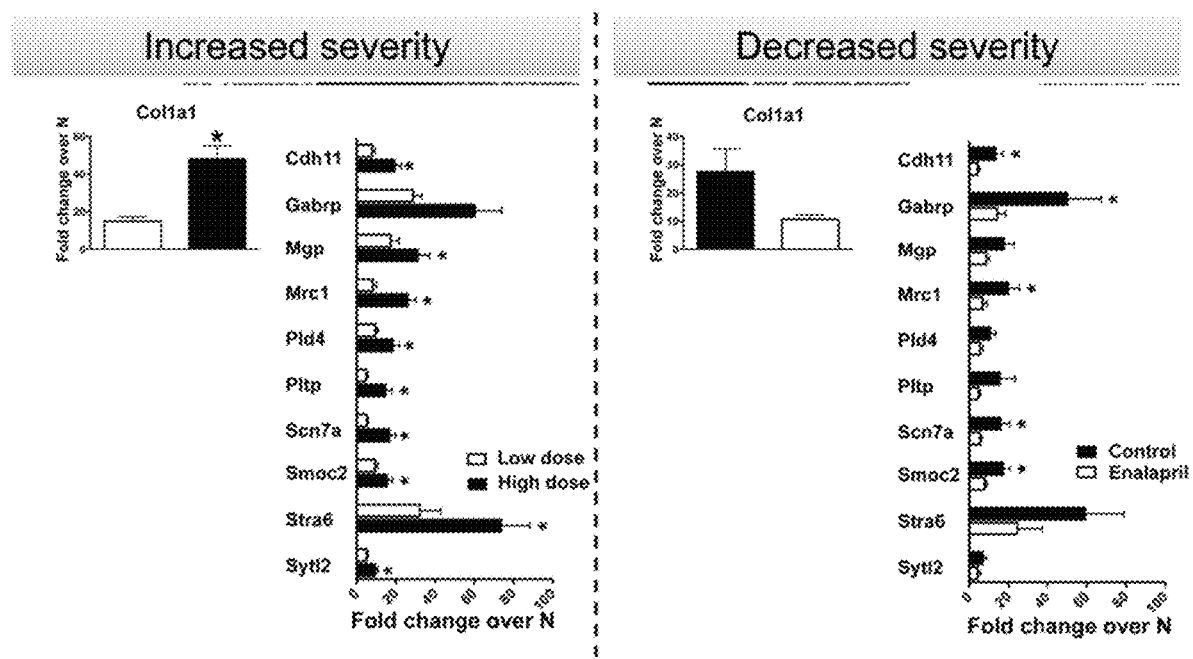
FIGS. 4A-4D demonstrate that expression of 10 candidate genes in the kidney increases with increased severity and responds to treatment.

A biomarker is particularly advantageous if it will not only detect the disease but also give information on prognosis, indicating if a patient responds to treatment as evidenced by declining fibrosis or whether the patient is progressing towards end stage renal disease as evidenced by increasing fibrosis. To test this, mice were injected with a higher dose of FA (375 mg/dl) that resulted in increased kidney fibrosis at day 14 compared to the previously used 250 mg/kg dose (Low dose) indicated by histology and ~3 fold ($p<0.05$) greater increase in collagen 1a1 expression (FIG. 4B). Nine out of ten candidate fibrosis markers showed significantly ($p<0.05$) higher mRNA levels in the High dose group compared to the Low dose group (FIG. 4B). Masson's trichome staining indicated increased tubule-interstitial fibrosis 14 days after FA injection with high dose (375 mg/kg) when compared to those from the previously used 250 mg/kg dose (data not shown).

Conversely, to test if the markers reflect recovery from fibrosis interventions on the renin-angiotensin system were used. Such treatments can prevent the progression of renal damage, reducing proteinuria and even resulting in regression of glomerulosclerosis, tubulointerstitial fibrosis and vascular lesions in humans and animal models (12). Mice were treated with 200 mg/l of the angiotensin converting enzyme (ACE) inhibitor enalapril (13) continuously in the drinking water after FA injection, and this resulted in reduced kidney fibrosis development by day 14, as indicated by histological assessment and ~3 fold reduction of collagen 1a1 mRNA expression (FIG. 4C). Kidney tissue Masson's trichrome staining indicated decreased kidney fibrosis 14 days after FA injection in mice receiving enalapril 200 mg/L of drinking water compared to control (plain water) throughout the experiment (data not shown). Most candidate markers also showed gene expression levels matching this reduced fibrosis development with enalapril treatment, with significant (p<0.05) decreases for Cdh11, Gabrp, Mrc1, Scn7a and Smoc2. Together these results indicate good correlation with fibrosis severity and response to treatment for the selected candidate biomarkers.

Testing the Specificity of Candidate Markers in a Mouse Model and Patients with Liver Fibrosis.

Figures 5A, 5B, 5C, 5D:
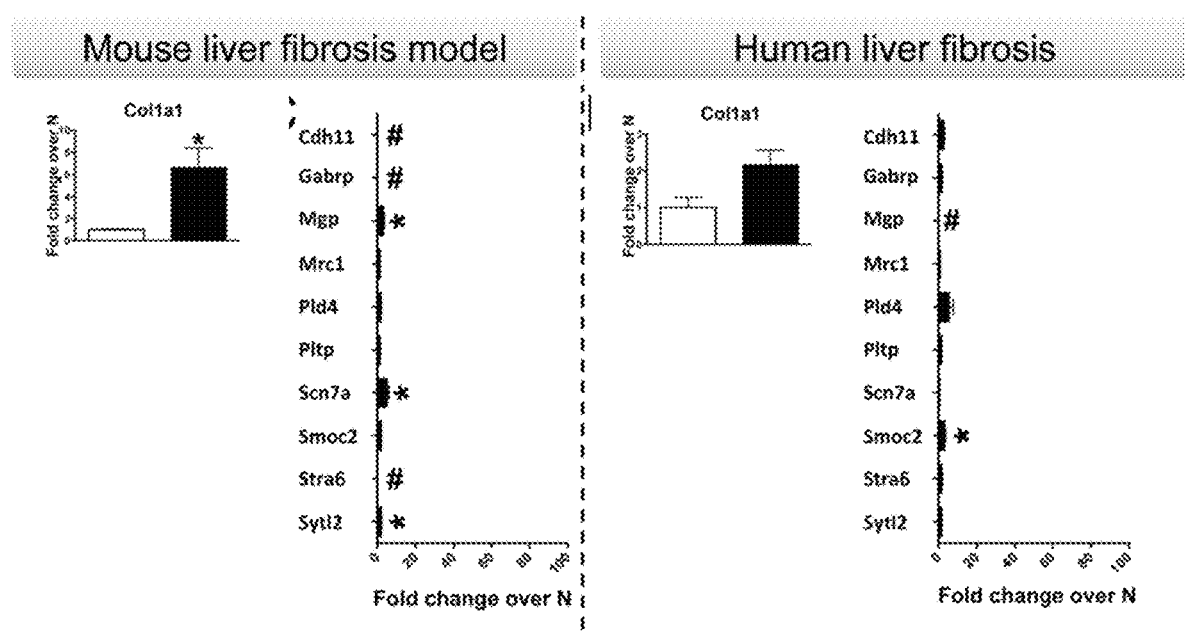
FIGS. 5A-5D demonstrate that modest increases in some of the candidate 10 genes in mice and human following liver fibrosis.

Fibrosis is a universal pathological finding for chronic diseases in any organ (14) and it would be useful to identify biomarkers of fibrosis that are specific for an organ or be able to indicate their origin. As indicated by Picrosirius red staining (data not shown), compared to mice fed control diet, ANIT exposure (an established method to induce liver fibrosis in mice (18)) significantly increased peribiliary fibrosis, as indicated by a robust deposition of collagen around intrahepatic bile ducts. This was reflected in significantly increased collagen 1a1 gene expression for the ANIT diet group (FIG. 5A). Although some candidate markers showed significantly higher (p<0.05) gene levels in the ANIT diet group (Mgp, Scn7a, Sytl2), fold changes were generally much lower than those in the kidney fibrotic models (FIG. 5B). Like the experimental setting, robust peribiliary and bridging fibrosis was observed in livers from patients with primary sclerosing cholangitis (PSC) as shown by Picrosirius red staining (data not shown) and an increase in collagen 1a1 mRNA expression (FIG. 5C). Except for Smoc2, there were no significant gene expression increases for the members of the candidate biomarkers panel (FIG. 5D). This indicates that at least in liver fibrosis the selected biomarkers will not exhibit increases to confound results for coexisting kidney fibrosis.

Development of SRM Assays and Evaluation of Biomarker Potential in Human Urine.

Figure 6A:
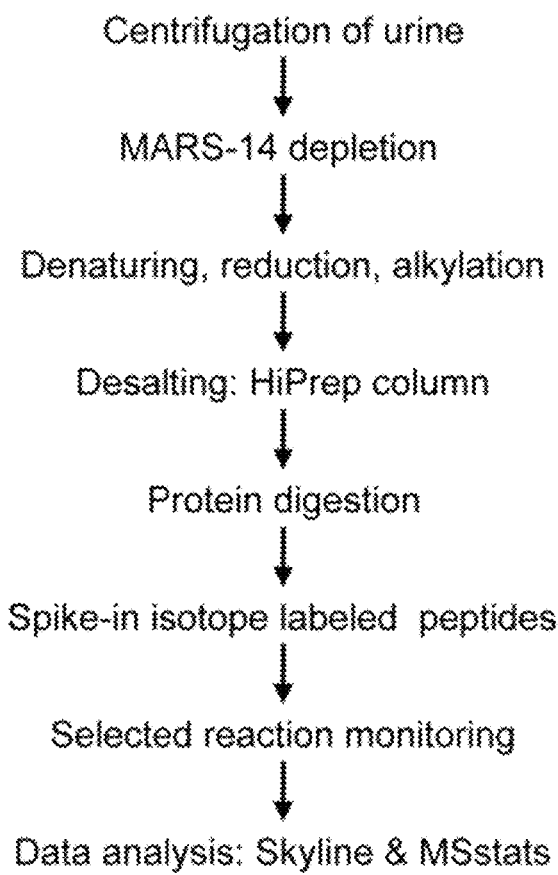
FIGS. 6A-6C demonstrate that SRM assay indicates increased protein levels of Cdh11 and Mrc 1 in urine samples from CKD patients when compared to those from healthy individuals.
Figure 6C:
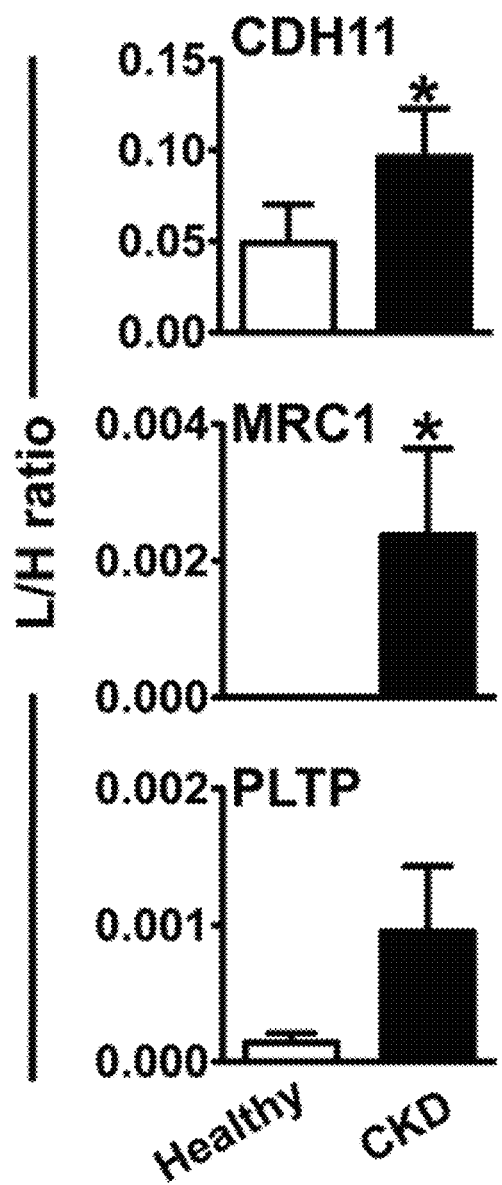
Figure 6B:
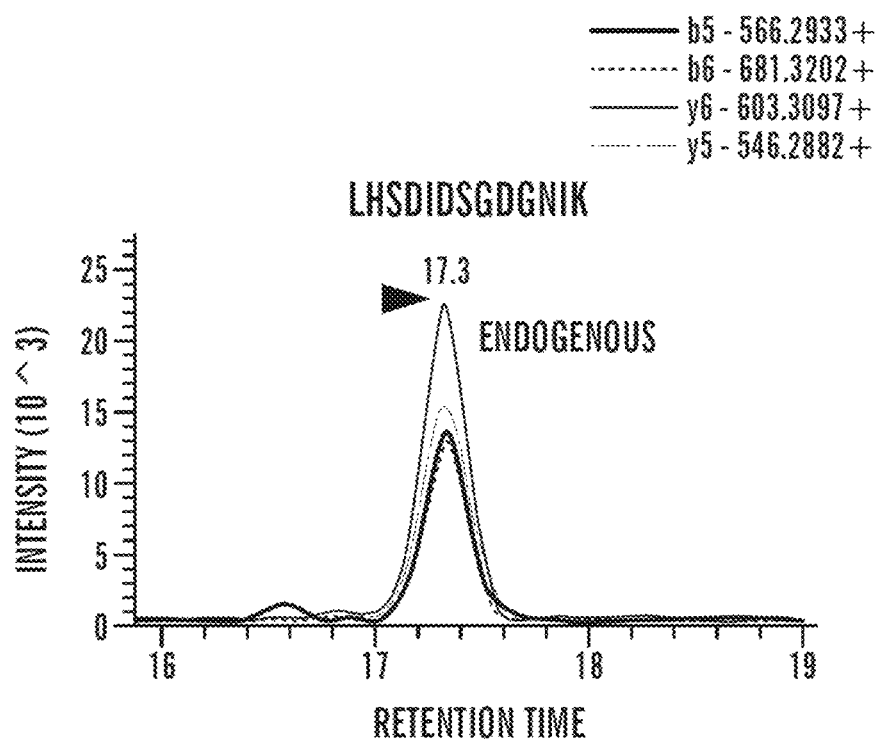
Figure 6B:
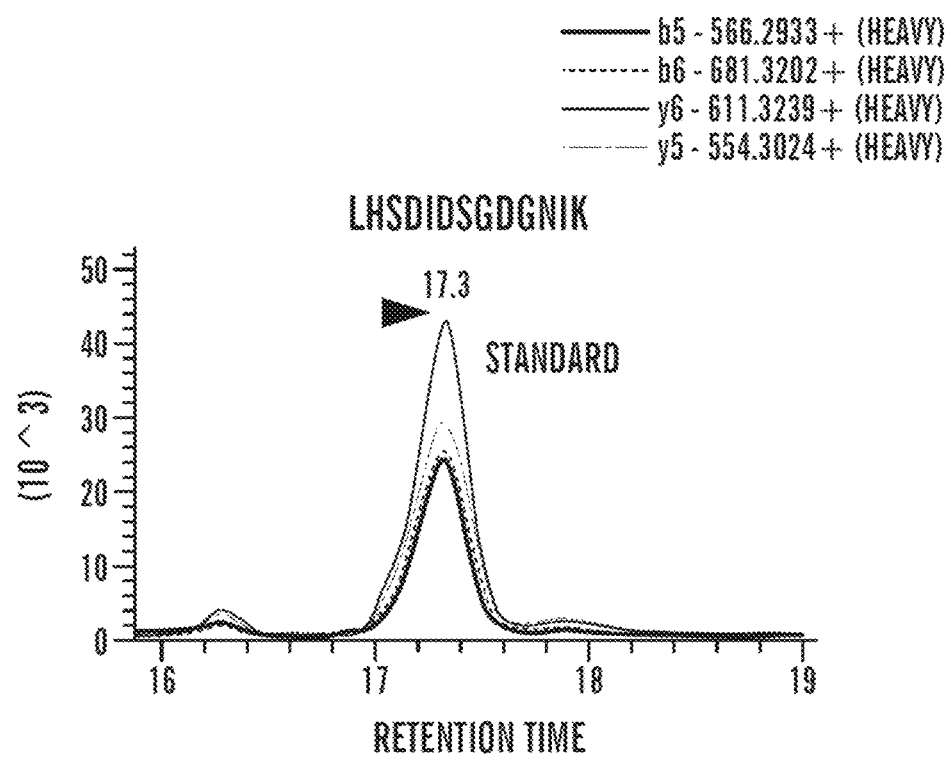
Figure 6B:
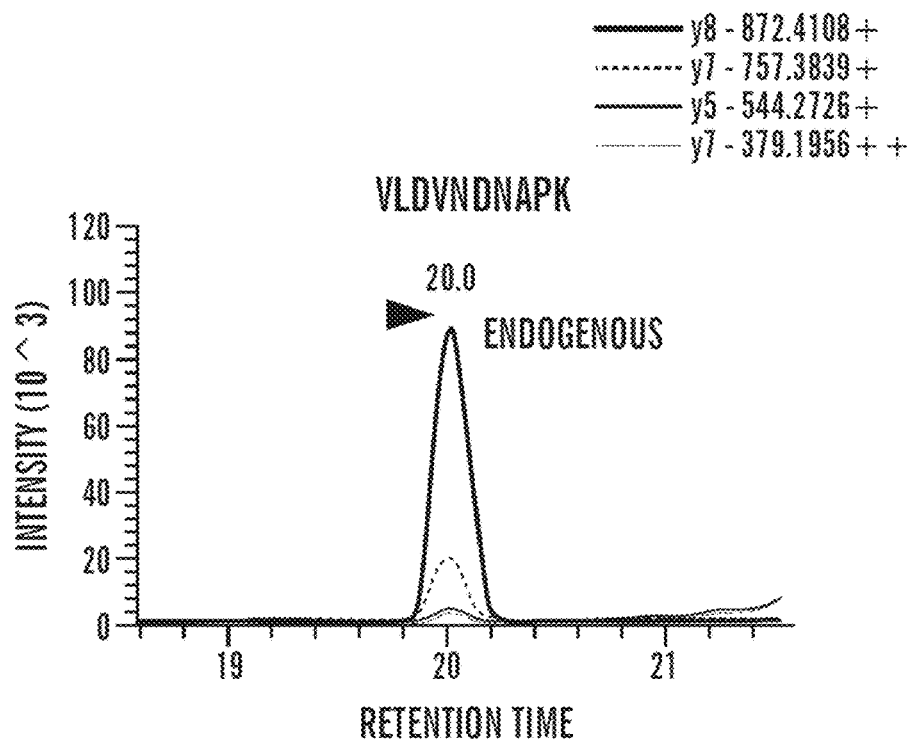
Figure 6B:
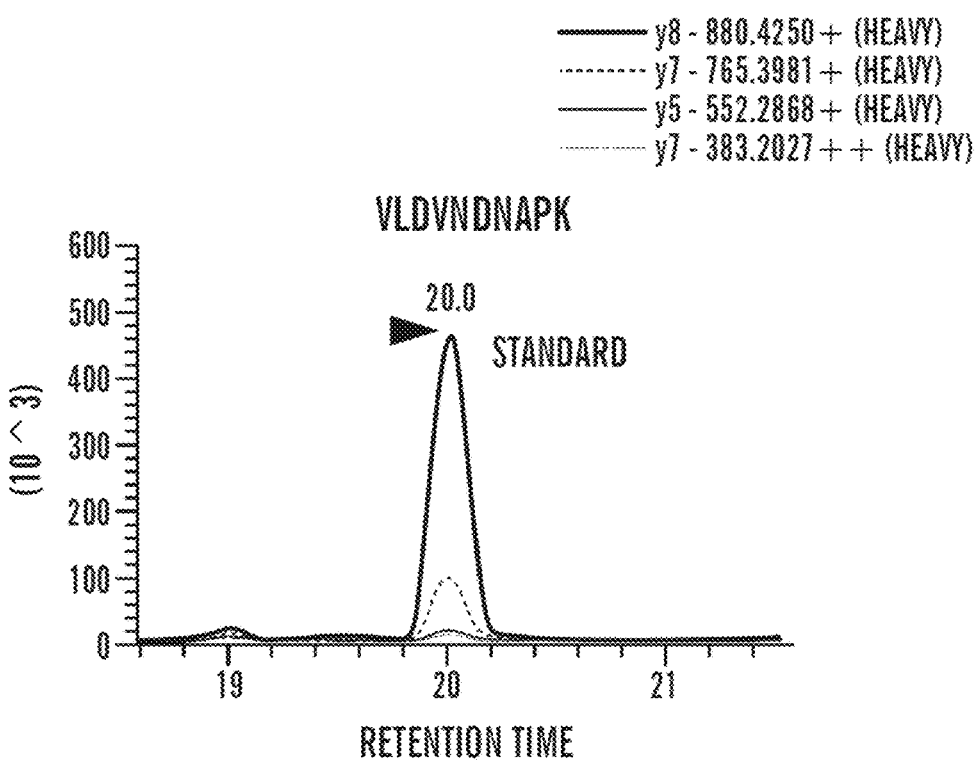

To test if the 10 candidate proteins are expressed at a level that can be detected in urine and begin assessing their biomarker potential in CKD, selected reaction monitoring (SRM), a sensitive and quantitative targeted mass spectrometry approach was carried out to analyze urine from 22 CKD patients and 24 healthy individuals. After affinity chromatography depletion of the 14 most abundant plasma proteins that are likewise present in urine at lower concentration, the urine samples were reduced, alkylated, desalted and trypsin digested (FIG. 6A). Proteotypic peptides that uniquely represent each protein were measured by SRM. To allow for relative quantification, each sample was spiked with isotope labeled peptides, heavy analogues of the light sequences, that function as an internal standard. Three out often targeted proteins were detected in urine by SRM at low fmol to attomol range. FIG. 6B shows an example of peptide LHSDIDSGDGNIK (SEQ ID NO: 1) and VLDVNDNAPK (SEQ ID NO: 2) from CDH11 detected in urine from CKD patients, the transitions of the endogenous light and labeled spiked-in peptide elute at the same retention time and in the same rank order confirming their identification. CDH11 and PLTP were detected in the urine from CKD patients as well as in the control samples while MRC1 was only detected in the urine from CKD patient sample cohort. The relative abundance of these proteins is presented as ratios of endogenous peptide to internal standard across individual samples (FIG. 6C). CDH11 showed the highest expression levels of the three proteins. PLTP and MRC1 were observed at similar levels to each other but considerably lower abundance compared to CDH11. MRC1 might be expressed at very low level in healthy samples but below the limit of detection of this approach. Of the 3 detectable proteins, group comparison indicates significant up-regulation for CDH11 and MRC1 in CKD patients, a 1.5 fold change over healthy within the 46 analyzed samples. Without wishing to be bound by theory, the low amount of starting material and possibly low expression levels may be reasons why the remaining proteins were not detected by SRM in this study.

Discussion.

Recent estimates place the lifetime risk of developing CKD with at least a moderate decrease in kidney function to more than 50%, second only to the risk for hypertension for chronic diseases, which stands at 83-90%(19). Yet, while the diagnosis and treatment of hypertension has become routine in clinical practice, for CKD there is an almost complete lack of diagnostic, prognostic and predictive biomarkers as well as specific therapies. Regardless of etiology, CKD is characterized structurally by excessive accumulation of extracellular matrix in glomeruli and tubular interstitium leading to a progressive loss in renal function (6). Related to the structural alterations, histological assessment of tissue biopsy is considered the gold standard for diagnosis, but it is rarely performed due to risks of hemorrhage, pain and death (20). For functional biomarkers, the formation of ultrafiltrate by glomeruli is the process that received the most attention. While the gold standard for the estimation of glomerular filtration rate is the timed urinary inulin clearance, it is difficult to perform and formulas based on serum creatinine or cystatin C concentration are the standard in clinical practice despite shortcomings. Together with measurements of proteinuria/albuminuria that are also used for the diagnosis and prognosis of CKD, they form the basis for the current definition of the disease (7). However, all these functional biomarkers have reduced sensitivity and specificity and they generally reflect late stages, when significant damage has already happened (8).

The current study was designed to discover novel biomarkers that can predict the development of kidney fibrosis, the common structural alteration in CKD. Described herein is the first report of gene expression profiling over time in the development of kidney fibrosis through the use of RNA-seq. Through this technology identified herein are several candidates with a temporal expression profile matching the development of fibrosis in the folic acid nephropathy model. This was confirmed in additional models for ten of these candidates for whom increased kidney protein expression was also detected in the folic acid model and CKD patients. The presence in urine for three candidates was demonstrated through the use of SRM technology. For two proteins, CDH11 and MRC1, the urinary levels were found to be significantly higher in CKD patients compared to healthy individuals. This is the first report of urinary measurement for these two proteins as biomarkers of CKD. As urine is an easily accessible, stable biological sample whose proteome reflects in large part on the kidney structure and function (11), these results demonstrate urinary measurement for these proteins as non-invasive, translational biomarkers of CKD.

The fold change for urinary levels in CKD patients vs. healthy controls, were significant for CDH11 and MRC1. Without wishing to be bound by theory, the detection of MRC1 only in CKD patients could suggest a better discriminatory potential even in the absence of a high fold change. To our knowledge, this is the first report of MRC1 measurement in the urine. An increase in Cdh11 or Mrc1 gene expression was not detected in liver fibrosis.

There is great interest in developing new biomarkers for chronic kidney disease. While many markers are currently being evaluated none are clinically approved yet (9). The present study identifies, e.g., CDH11 and MRC1 as novel urinary biomarkers for kidney fibrosis that characterizes CKD.

Methods

Animal studies.

All animal studies were performed in compliance with the Guide for Care and Use of Laboratory Animals as adopted and promulgated by the National Institutes of Health and were approved by the Harvard Medical School Animal Care and Use Committees (IACUC). Mouse models of acute kidney injury (25), kidney fibrosis (26) and liver fibrosis (18) were used as previously described by our group.

Human Studies.

All participants were patients or healthy volunteers recruited at Brigham and Women's Hospital, Boston. The Institutional Review Board approved the protocols for recruitment and sample collection, which was performed with written informed consent of the participants. Urine samples from patients with Chronic Kidney Disease (CKD) were obtained from the BWH ambulatory nephrology clinic. Inclusion criteria included a diagnosis of CKD under the care of a nephrologist at BWH; eGFR 15 to 60 ml/min/1.73 $m^2$ with any degree of proteinuria or eGFR>60 with >=1 gm proteinuria. Patients were excluded if they had a recent hospitalization or episode of AKI (>50% rise in serum creatinine over a 1 week period) within 3 months; active glomerulonephritis; reported or suspected urinary tract infection within the past 3 weeks; or planned change in the dose of a diuretic and/or antihypertensive medication during the study period. Urine samples from healthy volunteers were obtained from the PhenoGenetics Project, a study of the impact of genetic variation in healthy individuals. Participants 18 to 65 years of age were recruited from the Boston area through advertisements in local media and flyers. Inclusion criterion was willingness to provide 120 mL of blood four times per year for five years. Exclusion criteria were the presence of self-reported inflammatory diseases (e.g., asthma or psoriasis), autoimmune diseases (e.g, lupus of multiple sclerosis), chronic metabolic diseases (e.g., thyroid disease or diabetes), or chronic infections (e.g., Hepatitis B or C; HIV).

Deidentified human kidney tissue samples from patients with severe kidney fibrosis were obtained from the Department of Pathology at Brigham and Women's Hospital. Deidentified liver tissue samples from patients with primary sclerosing cholangitis (PSC) undergoing liver transplant were obtained through the University of Kansas Medical Center Liver Center Tissue Bank.

Immunofluorescence, Immunoblottting and Quantitative Real-Time PCR.

All the techniques were performed using standard protocols established in the laboratory (25, 26). Primary antibodies used were Abcam (rabbit polyclonal: anti-CDH11, GABRP, MRC1, PLD4, PLTP, SCN7A, STRA6) and Santa Cruz Biotechnology (rabbit polyclonal: anti-MGP, SMOC2; goat polyclonal: SYTL2). Primer pairs used are listed in Tables 2 and 3.

RNA-Seq.

RNA samples (n=3 mice/time point) were sequenced at the Bioplymers Facility at the Harvard Medical School. Libraries were prepared from 10 ng total RNA per sample using the IntegenX Apollo 324 system and NuGEN SPIA reagents. Libraries were multiplexed in groups of three per lane of a flowcell and 50 cycle, paired-end sequencing was performed on an Illumina HiSeq2000 instrument. Illumina sequence quality was surveyed with FastQC (available on the world wide web at bioinformatics.babraham.ac.uk/projects/fastqc/) to ensure suitability of library generation and sequencing for further analysis. Adapters and lower quality bases were trimmed with Cutadapt (available on the world wide web at code.google.com/p/cutadapt/), using a Phred quality cutoff of 20, and reassessed with FastQC. Trimmed reads were aligned to the Ensembl NCBIM37 *Mus musculus* genome build with TopHat2. Aligned reads were summarized at the gene level against the Illumina iGenomes (available on the world wide web at tophat.cbcb.umd.edu/igenomes.html) NCBIM37 *Mus musculus* gene annotations using HTSeq (available on the world wide web at huber.embl.de/users/anders/HTSeq/doc/overview.html). Normalized read counts at all time points after FA injection were tested with DESeq for differential gene expression against Normal samples using an adjusted p-value cutoff of 0.2. The full dataset is available in the NCBI GEO database with the accession number GSE65267. Raw data is accessible on the world wide web at ncbi.nlm.nih.gov/geo/query/acc.cgi?acc=GSE65267.

SRM Assays.

Urine from control and CKD patient samples were randomized prior to sample preparation and mass spectrometry analysis. Urine was centrifuged at 10,000×g for 10 min at room temperature; the pellet was discarded. 1 mL supernatant was depleted from the 14 most abundant plasma proteins using the multiple affinity removal system (MARS Hu-14, 4.6×100 mm, Agilent Technologies, Santa Clara, Calif.) according to the manufacturer's protocol. Thirty-nine proteotypic peptides that are unique to the 10 proteins studied and their respective SRM assays were obtained from SRMAtlas (srmatlas.org)(27). For each peptide sequence the heavy isotope labeled analogue with the C-terminal arginine as R[13C6; 15N4] or lysine as K[13C6; 15N2] and cysteine residues carbamidomethylated was synthesized as crude product (Thermo-Fisher, Rockford, Ill.) to allow for relative quantification. Samples were analyzed on a QTRAP 5500 LC-MS system equipped with a Nano Spray Source III and an Eksigent Nano LC 2D (AB Sciex, Foster City, Calif.). Two µg urine digest spiked with an aliquot of the mixed standard peptides at a concentration between 45 fmol and 600 fmol for each individual peptide. Peptides were analyzed in scheduled SRM mode with Q1 and Q3 set to unit resolution, a 2 s cycle time, a declustering potential of 70 and a retention time window of 360 s. SRM data and the transition list are available in the PASSEL data repository peptideatlas.org/PASS/PASS00647. SRM data were analyzed with Skyline (version 2.5.06157). The relative protein expression level is reported as ratio of endogenous light to the heavy standard. The level of protein up- or down-regulation is determined with the MSstats software package.

Statistical Analysis.

Statistical analyses (student's t-tests and Pearson correlations) were performed using GraphPad Prism 5 (GraphPad Software Inc.). Hierarchical clustering was performed using the MeV software (28).

Animal Studies.

Mice were purchased from Charles River Laboratories and were acclimated to our animal facility for at least one week prior to experimentation.

Folic acid nephropathy model: Male Balb/c mice (25-29 g) received a single intraperitoneal (ip) injection of 250 mg/kg folic acid (FA) dissolved in a 0.3 M sodium bicarbonate solution. Mice were sacrificed at 1, 2, 3, 7 and 14 days following administration. For the experiments testing increased kidney fibrosis, mice received a single ip injection of 375 mg/kg FA and they were sacrificed at 14 days. For the experiments testing decreased kidney fibrosis following FA injection, all mice received a 250 mg/kg FA ip and cages were randomized to receive either a 200 mg/L solution of enalapril in the water bottle for the treatment group or regular water for the control group throughout the duration of the experiment. All mice were sacrificed at 14 days.

Cisplatin-induced acute kidney injury model: Male Balb/c mice (25-29 g) received a single ip injection of 20 mg/kg cisplatin dissolved in normal saline or vehicle alone. These mice were sacrificed and samples were collected 72 hours after the injection.

Surgical models of acute kidney injury and kidney fibrosis: All surgical procedures were performed under general anesthesia (50 mg/kg pentobarbital sodium, ip) and mice received fluid lost replacement (1 mL normal saline, heated at 37° C., subcutaneously, immediately after surgery) as well as pain medication (buprenorphine, 0.05 mg/kg, subcutaneously, every 12 hours for the first 2 days, first dose in the 1 mL normal saline dose immediately after surgery and 3 additional doses in 50 normal saline). Unilateral ureteral obstruction (UUO) was performed in male Balb/c mice as previously described (10) and mice were sacrificed for sample collection at 3, 7 and 14 days after the intervention. Bilateral renal ischemia reperfusion injury was performed in male Balb/c mice by applying Roboz micro clips (70 grams pressure) on both renal arteries for 30 minutes and animals were sacrificed at 1, 7 and 14 days. Sham surgery, with animals that received the laparotomy and renal pedicle manipulation but not the hemostasis, was performed in additional mice and these were sacrificed 1 day after the intervention. Unilateral ischemia reperfusion as well as sham surgery was performed similarly in $C_{57}BL/6$ female mice and these mice were sacrificed 41 days after the intervention.

Liver fibrosis model: Male $C_{57}BL/6$ mice (25-29 g) were fed chow (AIN-93M) containing 0.025% α-naphthylisothiocyanate (ANIT diet) for 4 weeks prior to sacrifice. Animals were housed in an Association for Assessment and Accreditation of Laboratory Animal Care International-accredited facility at Michigan State University and all procedures were approved by the Michigan State University Institutional Animal Care and Use Committee.

Biospecimen collection: At the moment of sacrifice, blood was collected from the inferior vena cava under isoflurane anesthesia, and, following opening of the thoracic cavity to ensure that the animal is deceased, the kidneys were retrieved and sectioned in samples dedicated for histology and immunfluorescence (fixed in 10% neutral buffered formalin), protein and RNA analysis (flash-frozen in liquid nitrogen). Similarly, liver tissue sections from the left lateral lobe of the ANIT fed mice were fixed in neutral buffered formalin for histopathological processing, while other liver sections were flash-frozen in liquid nitrogen. Blood was collected from mice in heparinized tubes and plasma was separated following centrifugation at 7500 g for 5 minutes. Blood urea nitrogen (BUN) was measured using an InfinityUrea kit (Thermo Fisher Scientific, Wilmington, Del.) and serum creatinine (SCr) was measured using a Creatinine Analyzer II (Beckman Coulter).

Human Studies.

Urine was collected from spontaneous voids or from indwelling Foley catheters. Urines dipstick analysis was performed (Multistix 8 SG, Bayer Corporation), followed by centrifugation at 3000 g for 10 minutes and microscopic examination of the urine sediment (Olympus microscope). The urine supernatant was aliquoted into 1.8 mL eppendorf tubes and frozen within 4 hours of collection at −80° C. No additives or protease inhibitors were added. Urinary creatinine concentrations were measure using commercially available kit from Cayman Chemical.

Histology.

Formalin fixed, paraffin embedded kidney sections were Masson Trichrome's stained and evaluated by a renal pathologist under a light microscope in blinded fashion relative to sample group. Percent area of fibrosis relative to the total section area was evaluated. Sirius red staining of the liver sections was performed at the Michigan State University Investigative Histopathology Laboratory.

Immunoflurescence.

Paraffin embedded kidney tissue sections (6 μm) were dewaxed and rehydrated by successive immersion for 5 min in 100% xylene, 1:1 xylene-ethanol, 100%, 90% and 70% ethanol solutions. Following heat-induced antigen retrieval, immunostaining was performed using antibodies from Abcam (rabbit polyclonal: anti-CDH11, GABRP, MRC1, PLD4, PLTP, SCN7A, STRA6) and Santa Cruz Biotechnology (rabbit polyclonal: anti-MGP, SMOC2; goat polyclonal: SYTL2). Primary antibodies were detected using species-specific Cy3 or FITC labeled secondary antibodies (Jackson ImmunoResearch Laboratories) and 4',6-Diamidino-2-phenylindole-containing mounting medium (Sigma-Aldrich) was used for nuclear staining. Images were captured at 630× magnification on a Carl Zeiss Axiolmager.M2 using the AxioVision SE64 software.

Western Blot.

Immunoblot analysis was performed as previously described (29). The sources of primary antibodies were: Abcam (rabbit polyclonal: anti-GABRP, MRC1, PLD4, PLTP, SCN7A, STRA6), Santa Cruz Biotechnology (rabbit polyclonal: anti-SMOC2; goat polyclonal: SYTL2), Life Technologies (mouse monoclonal: anti-CDH11), Enzo Life Sciences (mouse monoclonal: anti-MGP), Sigma (mouse monoclonal α-tubulin; assessed for loading control). Horseradish peroxidase-conjugated secondary antibodies against mouse, rabbit, or goat were from Jackson ImmunoResearch Laboratories. Images of the blots were taken using a Chemi-Doc instrument and the analysis was performed using the ImageLab software provided by the manufacturer (BioRad).

RNA Isolation and qRT-PCR.

Total RNA was extracted from frozen kidney tissue using TRIzol reagent (Invitrogen). Following RNA concentration measurement by NanoDrop spectrophotometer (Thermo Fischer Scientific), 1 μg RNA was used for cDNA preparation using QuantiTect Reverse Transcription Kit from Qiagen (Valencia, Calif.). qRT-PCR using QuantiFast SYBR Green PCR Kit (Qiagen) was performed in 384-well plates on an Applied Biosystems 7900HT Fast Real-Time PCR System instrument with the following temperature profile: 3 min enzyme activation at 95° C. followed by 40 cycles of 95° C. for 10 s, and 55° C. for 30 s. Primer pairs used are listed in Supplementary Table 1. Gapdh was used as reference gene for normalization. The SDS 2.4 software (Applied Biosystems) was used to compute the threshold cycle (Cq) and the relative expression for an mRNA was assessed using the $2^{-\Delta cq}$ method.

RNA-Seq.

Three RNA samples at each time-point in the FA nephropathy progression were sequenced at the Bioplymers Facility at the Harvard Medical School. The quantity and quality of mRNA were assayed on an Agilent 2200 TapeStation instrument and by SYBR qPCR assay. Libraries were prepared from 10 ng total RNA per sample using the IntegenX Apollo 324 system and NuGEN SPIA reagents. Libraries were multiplexed in groups of three per lane of a flowcell and 50 cycle, paired-end sequencing was performed on an Illumina HiSeq2000 instrument. Illumina sequence quality was surveyed with FastQC (available on the world wide web at bioinformatics.babraham.ac.uk/projects/fastqc/) to ensure suitability of library generation and sequencing for further analysis. Adapters and lower quality bases were trimmed with Cutadapt (https://code.google.com/p/cutadapt/), using a Phred quality cutoff of 20, and reassessed with FastQC. Trimmed reads were aligned to the Ensembl NCBIM37 *Mus musculus* genome build with TopHat2. Aligned reads were summarized at the gene level against the Illumina iGenomes (available on the world wide web at tophat.cbcb.umd.edu/igenomes.html) NCBIM37 *Mus musculus* gene annotations using HTSeq (available on the world wide web at huber.embl.de/users/anders/HTSeq/doc/overview.html). Normalized read counts at all time points after FA injection were tested with DESeq for differential gene expression against Normal samples using an adjusted p-value cutoff of 0.2. The full dataset is available in the NCBI GEO database with the accession number GSE65267. Raw data is accessible on the world wide web at ncbi.nlm.nih.gov/geo/query/acc.cgi?acc=GSE65267.

SRM Assays.

Urine from control and CKD patient samples were randomized prior to sample preparation and mass spectrometry analysis. Urine was centrifuged at 10,000×g for 10 min at room temperature; the pellet was discarded. 1 mL supernatant was depleted from the 14 most abundant plasma proteins using the multiple affinity removal system (MARS Hu-14, 4.6×100 mm, Agilent Technologies, Santa Clara, Calif.) according to the manufacturer's protocol. The depleted fraction was collected in 1.25 mL of MARS14 Buffer A and denatured by adding 600 mg urea to 8 M final concentration. Samples were reduced with 5 mM dithiothreitol (30 min, 55° C.), alkylated with 14 mM iodoacetamide (30 min, room temperature and in the dark) and desalted using a GE HiPrep 26/10 column (GE HealthCare Life Sciences, Pittsburgh, Pa.) and a 1200 HPLC system (Agilent Technologies, Santa Clara, Calif.). The protein concentration of the desalted samples was determined by bicinchoninic acid (BCA) protein assay (Thermo-Fisher, Waltham, Mass.). Samples were digested with sequencing grade modified trypsin (Promega Corporation, Madison, Wis.) at 1:50 enzyme:substrate ratio at 37° C. for 16 h. The digest was dried under centrifugal evaporation (Savant, Thermo-Fisher Waltham, Mass.) and resolubilized in 1% formic acid to a concentration of 1.1 µg/µL.

41 proteotypic peptides that are unique to the 10 proteins studied and their respective SRM assays were obtained from SRMAtlas (srmatlas.org). The SRMAtlas is a publically accessible resource of complete proteome SRM assays for selected organisms. The human SRMAtlas build constructed from quadrupole fragmentation generated human peptides were used to select the best proteotypic peptides for each protein to perform SRM (Kusebauch et al., in preparation). For each peptide sequence the heavy isotope labeled analogue with the C-terminal arginine as R[13C6; 15N4] or lysine as K[13C6; 15N2] and cysteine residues carbamidomethylated was synthesized as crude product (Thermo-Fisher, Rockford, Ill.) to allow for relative quantification. Samples were analyzed on a QTRAP 5500 LC-MS system equipped with a Nano Spray Source III and an Eksigent Nano LC 2D (AB Sciex, Foster City, Calif.). 2 µg urine digest spiked with an aliquot of the mixed standard peptides at a concentration between 45 fmol and 600 fmol for each individual peptide were loaded on a C18 ProteoCol trap column (0.3×10 mm, 300 µm, 3 µm dp (SGE, Victoria, Australia) in 0.1% formic acid in water (v/v) for 5 min at a flow rate of 5 µl/min. Chromatographic separations were performed with a C18 Acclaim PepMap 100 analytical column (15 cm, 75 µm, 3 µm, 100 Å, Thermo Scientific, Rockford, Ill.) using 0.1% formic acid in water (v/v) (A) and 0.1% formic acid in acetonitrile (v/v) (B) and a 60 min gradient from 3% to 33% B and 33% to 63% B at 60-67.5 min at a flow rate of 300 nL/min. The analytical column was connected to a PicoTip fused-silica emitter (360 µm×20 µm with a 10 µm tip, New Objective, Woburn, Mass.). Peptides were analyzed in scheduled SRM mode with Q1 and Q3 set to unit resolution, a 2 s cycle time, a declustering potential of 70 and a retention time window of 360 s. SRM data and the transition list are available in the PASSEL data repository available on the world wide web at peptideatlas.org/PASS/PASS00647. SRM data were analyzed with Skyline (version 2.5.06157). SRM traces were integrated with default settings and manual inspected to verify correct peak assignment and co-elution of endogenous and isotope labeled standard peptides. Transition peak areas of identified peptides were exported to MSstats (version 2.3.5) for model-based quantification using the quantile normalized results. The relative protein expression level is reported as ratio of endogenous light to the heavy standard. The level of protein up- or down-regulation is determined with the MSstats software package.

REFERENCES

1. K. Matsushita, S. H. Ballew, B. C. Astor, P. E. Jong, R. T. Gansevoort, B. R. Hemmelgarn, A. S. Levey, A. Levin, C. P. Wen, M. Woodward, J. Coresh, Cohort Profile: The Chronic Kidney Disease Prognosis Consortium. *International journal of epidemiology*, (2012).
2. J. Coresh, D. Byrd-Holt, B. C. Astor, J. P. Briggs, P. W. Eggers, D. A. Lacher, T. H. Hostetter, Chronic kidney disease awareness, prevalence, and trends among U.S. adults, 1999 to 2000. *Journal of the American Society of Nephrology: JASN* 16, 180-188 (2005).
3. P. Stenvinkel, Chronic kidney disease: a public health priority and harbinger of premature cardiovascular disease. *J Intern Med* 268, 456-467 (2010).
4. T. J. Hoerger, J. S. Wittenborn, J. E. Segel, N. R. Burrows, K. Imai, P. Eggers, M. E. Pavkov, R. Jordan, S. M. Hailpern, A. C. Schoolwerth, D. E. Williams, A health policy model of CKD: 1. Model construction, assumptions, and validation of health consequences. *American journal of kidney diseases: the official journal of the National Kidney Foundation* 55, 452-462 (2010).
5. A. S. Levey, J. Coresh, Chronic kidney disease. *Lancet* 379, 165-180 (2012).
6. J. M. Lopez-Novoa, A. B. Rodriguez-Pena, A. Ortiz, C. Martinez-Salgado, F. J. Lopez Hernandez, Etiopathology of chronic tubular, glomerular and renovascular nephropathies: clinical implications. *J Transl Med* 9, 13 (2011).
7. P. E. Stevens, A. Levin, Evaluation and management of chronic kidney disease: synopsis of the kidney disease: improving global outcomes 2012 clinical practice guideline. *Annals of internal medicine* 158, 825-830 (2013).
8. P. Devarajan, The use of targeted biomarkers for chronic kidney disease. *Advances in chronic kidney disease* 17, 469-479 (2010).

9. R. G. Fassett, S. K. Venuthurupalli, G. C. Gobe, J. S. Coombes, M. A. Cooper, W. E. Hoy, Biomarkers in chronic kidney disease: a review. *Kidney international* 80, 806-821 (2011).
10. F. L. Craciun, A. K. Ajay, D. Hoffmann, J. Saikumar, S. L. Fabian, V. Bijol, B. D. Humphreys, V. S. Vaidya, Pharmacological and genetic depletion of fibrinogen protects from kidney fibrosis. *American journal of physiology. Renal physiology* 307, F471-484 (2014).
11. A. Konvalinka, J. W. Scholey, E. P. Diamandis, Searching for new biomarkers of renal diseases through proteomics. *Clinical chemistry* 58, 353-365 (2012).
12. P. Ruggenenti, P. Cravedi, G. Remuzzi, Mechanisms and treatment of CKD. *Journal of the American Society of Nephrology: JASN* 23, 1917-1928 (2012).
13. M. El Chaar, J. Chen, S. V. Seshan, S. Jha, I. Richardson, S. R. Ledbetter, E. D. Vaughan, Jr., D. P. Poppas, D. Felsen, Effect of combination therapy with enalapril and the TGF-beta antagonist 1D11 in unilateral ureteral obstruction. *American journal of physiology. Renal physiology* 292, F1291-1301 (2007).
14. S. L. Friedman, D. Sheppard, J. S. Duffield, S. Violette, Therapy for fibrotic diseases: nearing the starting line. *Science translational medicine* 5, 167sr161 (2013).
15. D. J. Schneider, M. Wu, T. T. Le, S. H. Cho, M. B. Brenner, M. R. Blackburn, S. K. Agarwal, Cadherin-11 contributes to pulmonary fibrosis: potential role in TGF-beta production and epithelial to mesenchymal transition. *FASEB journal: official publication of the Federation of American Societies for Experimental Biology* 26, 503-512 (2012).
16. E. H. Noss, S. K. Chang, G. F. Watts, M. B. Brenner, Modulation of matrix metalloproteinase production by rheumatoid arthritis synovial fibroblasts after cadherin 11 engagement. *Arthritis Rheum* 63, 3768-3778 (2011).
17. E. C. Cranenburg, R. Koos, L. J. Schurgers, E. J. Magdeleyns, T. H. Schoonbrood, R. B. Landewe, V. M. Brandenburg, O. Bekers, C. Vermeer, Characterisation and potential diagnostic value of circulating matrix Gla protein (MGP) species. *Thrombosis and haemostasis* 104, 811-822 (2010).
18. N. Joshi, A. K. Kopec, K. Towery, K. J. Williams, J. P. Luyendyk, The antifibrinolytic drug tranexamic acid reduces liver injury and fibrosis in a mouse model of chronic bile duct injury. *The Journal of pharmacology and experimental therapeutics* 349, 383-392 (2014).
19. M. E. Grams, E. K. Chow, D. L. Segev, J. Coresh, Lifetime Incidence of CKD Stages 3-5 in the United States. *American journal of kidney diseases: the official journal of the National Kidney Foundation* 62, 245-252 (2013).
20. C. Manno, G. F. Strippoli, L. Arnesano, C. Bonifati, N. Campobasso, L. Gesualdo, F. P. Schena, Predictors of bleeding complications in percutaneous ultrasound-guided renal biopsy. *Kidney international* 66, 1570-1577 (2004).
21. M. V. Pahl, Z. Ni, L. Sepassi, H. Moradi, N. D. Vaziri, Plasma phospholipid transfer protein, cholesteryl ester transfer protein and lecithin:cholesterol acyltransferase in end-stage renal disease (ESRD). *Nephrology, dialysis, transplantation: official publication of the European Dialysis and Transplant Association—European Renal Association* 24, 2541-2546 (2009).
22. T. Kushiyama, T. Oda, M. Yamada, K. Higashi, K. Yamamoto, Y. Sakurai, S. Miura, H. Kumagai, Alteration in the phenotype of macrophages in the repair of renal interstitial fibrosis in mice. *Nephrology (Carlton)* 16, 522-535 (2011).
23. H. G. Mesrobian, M. E. Mitchell, W. A. See, B. D. Halligan, B. E. Carlson, A. S. Greene, B. T. Wakim, Candidate urinary biomarker discovery in ureteropelvic junction obstruction: a proteomic approach. *J Urol* 184, 709-714 (2010).
24. H. Keshishian, T. Addona, M. Burgess, D. R. Mani, X. Shi, E. Kuhn, M. S. Sabatine, R. E. Gerszten, S. A. Carr, Quantification of cardiovascular biomarkers in patient plasma by targeted mass spectrometry and stable isotope dilution. *Molecular & cellular proteomics: MCP* 8, 2339-2349 (2009).
25. K. L. Pellegrini, T. Han, V. Bijol, J. Saikumar, F. L. Craciun, W. W. Chen, J. C. Fuscoe, V. S. Vaidya, MicroRNA-155 deficient mice experience heightened kidney toxicity when dosed with cisplatin. *Toxicol Sci* 141, 484-492 (2014).
26. F. L. Craciun, A. K. Ajay, D. Hoffmann, J. Saikumar, S. L. Fabian, V. Bijol, B. D. Humphreys, V. S. Vaidya, Pharmacological and genetic depletion of fibrinogen protects from kidney fibrosis. *Am J Physiol Renal Physiol* 307, F471-484 (2014).
27. U. Kusebauch, E. W. Deutsch, D. S. Campbell, Z. Sun, T. Farrah, R. L. Moritz, Using PeptideAtlas, SRMAtlas, and PASSEL: Comprehensive Resources for Discovery and Targeted Proteomics. *Curr Protoc Bioinformatics* 46, 13 25 11-13 25 28 (2014).
28. A. I. Saeed, V. Sharov, J. White, J. Li, W. Liang, N. Bhagabati, J. Braisted, M. Klapa, T. Currier, M. Thiagarajan, A. Sturn, M. Snuffin, A. Rezantsev, D. Popov, A. Ryltsov, E. Kostukovich, I. Borisovsky, Z. Liu, A. Vinsavich, V. Trush, J. Quackenbush, TM4: a free, open-source system for microarray data management and analysis. *Biotechniques* 34, 374-378 (2003).
29. A. K. Ajay, T. M. Kim, V. Ramirez-Gonzalez, P. J. Park, D. A. Frank, V. S. Vaidya, A bioinformatics approach identifies signal transducer and activator of transcription-3 and checkpoint kinase 1 as upstream regulators of kidney injury molecule-1 after kidney injury. *Journal of the American Society of Nephrology: JASN* 25, 105-118 (2014).

TABLE 1

List of genes identified by RNA-seq as significantly different from normal at least at one time-point in the FA nephropathy progression. Data is presented as mean fold change from normal (n = 3/group); gene symbols in bold indicate the 10 candidates selected; gene symbols in italics indicate those that also met the selection criteria but were not chosen; fold changes in bold indicate $p < 0.2$ at DESeq analysis.

| Mgi symbol | Day 1 | Day 2 | Day 3 | Day 7 | Day 14 |
|---|---|---|---|---|---|
| Aacs | 0.23 | 0.08 | 0.20 | 0.51 | 1.01 |
| Aadat | 0.09 | 0.10 | 0.17 | 0.33 | 0.53 |
| Abca13 | 0.07 | 0.10 | 0.25 | 0.70 | 1.01 |
| Abca4 | 0.10 | 0.07 | 0.38 | 0.61 | 0.63 |
| Abca8a | 0.03 | 0.06 | 0.23 | 0.76 | 1.20 |
| Abca9 | 0.09 | 0.09 | 1.25 | 2.83 | 1.85 |
| Abp1 | 4.48 | 6.51 | 13.61 | 11.45 | 4.20 |
| Acmsd | 0.04 | 0.13 | 0.14 | 0.19 | 0.34 |
| Acy1 | 0.07 | 0.10 | 0.24 | 0.24 | 0.62 |
| Acy3 | 0.10 | 0.11 | 0.30 | 0.22 | 0.52 |
| Adamts1 | 9.06 | 6.54 | 7.41 | 4.24 | 2.63 |
| *Adamts16* | 1.50 | 3.67 | 8.09 | 13.70 | 3.24 |
| Adhfe1 | 0.13 | 0.21 | 0.36 | 0.39 | 0.67 |
| Afap1l1 | 0.09 | 0.11 | 0.25 | 0.26 | 0.40 |
| Agt | 20.58 | 25.98 | 18.23 | 17.89 | 4.88 |

TABLE 1-continued

List of genes identified by RNA-seq as significantly different from normal at least at one time-point in the FA nephropathy progression. Data is presented as mean fold change from normal (n = 3/group); gene symbols in bold indicate the 10 candidates selected; gene symbols in italics indicate those that also met the selection criteria but were not chosen; fold changes in bold indicate p < 0.2 at DESeq analysis.

| Mgi symbol | Day 1 | Day 2 | Day 3 | Day 7 | Day 14 |
|---|---|---|---|---|---|
| Agxt2l1 | 0.06 | 0.02 | 0.59 | 0.33 | 0.87 |
| AI607873 | 1.76 | 3.41 | 7.73 | 20.17 | 6.63 |
| Akap12 | 15.06 | 21.04 | 9.75 | 5.86 | 3.43 |
| Akr1b8 | 79.97 | 65.26 | 30.92 | 44.39 | 15.01 |
| Akr1c14 | 0.04 | 0.06 | 0.26 | 0.13 | 0.46 |
| Akr1c21 | 0.04 | 0.12 | 0.35 | 0.33 | 0.62 |
| Akr1d1 | 0.07 | 0.10 | 0.20 | 0.31 | 1.00 |
| Aldh1a2 | 24.56 | 10.24 | 6.58 | 19.53 | 14.25 |
| Alox5ap | 2.51 | 1.74 | 11.36 | 14.55 | 11.26 |
| Amacr | 0.11 | 0.14 | 0.70 | 0.28 | 0.61 |
| Amica1 | 4.53 | 1.49 | 9.87 | 41.56 | 44.49 |
| Ankrd1 | 30.01 | 14.30 | 29.13 | 10.98 | 6.12 |
| Anln | 5.84 | 16.30 | 7.69 | 3.82 | 1.98 |
| Anpep | 0.13 | 0.21 | 0.48 | 0.48 | 0.57 |
| Anxa2 | 9.19 | 8.99 | 6.51 | 6.11 | 3.65 |
| Apoc2 | 11.76 | 242.03 | 26.60 | 20.69 | 1.02 |
| Arhgap11a | 2.33 | 11.80 | 9.97 | 4.20 | 2.21 |
| Arhgap36 | 1.24 | 2.75 | 33.05 | 149.84 | 36.77 |
| Asns | 16.36 | 6.46 | 11.45 | 7.44 | 3.09 |
| Aspa | 0.13 | 0.21 | 0.29 | 0.28 | 0.68 |
| Aspdh | 0.08 | 0.04 | 0.23 | 0.14 | 0.34 |
| Ass1 | 0.10 | 0.10 | 0.19 | 0.31 | 0.59 |
| Atp2a3 | 0.04 | 0.11 | 0.87 | 1.75 | 1.03 |
| B3galnt1 | 0.09 | 0.17 | 0.38 | 0.76 | 0.99 |
| Bag2 | 6.95 | 5.10 | 4.94 | 3.18 | 1.79 |
| BC013712 | 0.06 | 0.06 | 0.76 | 1.14 | 0.83 |
| BC089597 | 0.19 | 0.05 | 0.49 | 0.89 | 0.59 |
| Bdh1 | 0.13 | 0.10 | 0.30 | 0.31 | 0.58 |
| Birc3 | 6.13 | 5.71 | 6.88 | 11.37 | 3.18 |
| C1qtnf3 | 0.03 | 0.07 | 0.37 | 0.14 | 0.45 |
| C3 | 82.12 | 185.03 | 275.58 | 173.67 | 43.48 |
| C4b | 7.86 | 9.71 | 10.37 | 5.93 | 3.91 |
| C8a | 0.08 | 0.01 | 0.19 | 0.22 | 0.38 |
| Calb1 | 0.07 | 0.12 | 0.19 | 0.82 | 1.28 |
| Capg | 12.02 | 11.19 | 12.07 | 8.48 | 6.13 |
| Cckar | 0.10 | 0.51 | 0.45 | 0.32 | 0.56 |
| Ccl2 | 18.46 | 41.17 | 134.97 | 198.61 | 73.50 |
| Ccl5 | 1.12 | 9.92 | 26.96 | 21.36 | 7.61 |
| Ccl6 | 0.93 | 0.82 | 5.02 | 14.89 | 5.47 |
| Ccl9 | 2.11 | 3.65 | 7.69 | 11.22 | 5.02 |
| Ccna2 | 4.06 | 10.99 | 11.07 | 3.17 | 1.43 |
| Ccnb2 | 3.98 | 43.81 | 39.55 | 8.92 | 4.76 |
| Ccr2 | 1.68 | 2.50 | 8.17 | 15.26 | 11.23 |
| Cd14 | 49.17 | 22.10 | 48.26 | 25.68 | 9.02 |
| Cd44 | 33.34 | 37.82 | 112.07 | 74.57 | 39.47 |
| Cdh11 | 0.67 | 0.98 | 2.68 | 6.46 | 11.31 |
| Ces1d | 0.06 | 0.14 | 0.76 | 0.61 | 1.21 |
| Ces1e | 0.13 | 0.01 | 0.29 | 0.25 | 0.59 |
| Ces1f | 0.10 | 0.05 | 0.25 | 0.19 | 0.59 |
| Cfi | 16.17 | 17.72 | 17.40 | 17.28 | 11.52 |
| Chrnb1 | 13.20 | 11.66 | 7.89 | 11.55 | 4.12 |
| Ckap21 | 8.29 | 47.27 | 67.64 | 12.41 | 6.79 |
| Clcf1 | 27.11 | 36.77 | 23.13 | 11.34 | 5.79 |
| Cldn3 | 6.26 | 5.05 | 5.50 | 10.71 | 2.06 |
| Cldn4 | 4.83 | 10.31 | 6.93 | 3.78 | 3.06 |
| Clec4n | 5.93 | 8.59 | 9.94 | 25.40 | 19.94 |
| Clu | 14.95 | 32.03 | 19.89 | 9.73 | 4.98 |
| Cmbl | 0.07 | 0.12 | 0.19 | 0.18 | 0.40 |
| Cml1 | 0.05 | 0.09 | 0.30 | 0.44 | 0.85 |
| Cndp1 | 0.08 | 0.15 | 0.35 | 0.42 | 0.82 |
| Cntnap5a | 0.05 | 0.04 | 0.15 | 0.10 | 0.56 |
| Col19a1 | 0.02 | 0.01 | 0.01 | 0.02 | 0.22 |
| Col3a1 | 3.30 | 2.93 | 6.98 | 11.08 | 13.34 |
| Col6a6 | 0.15 | 0.13 | 0.10 | 0.13 | 0.36 |
| Col8a1 | 5.29 | 5.34 | 5.34 | 14.30 | 7.99 |
| Cp | 13.38 | 24.07 | 17.99 | 13.92 | 5.59 |
| Cpn1 | 5.79 | 14.80 | 13.04 | 18.05 | 9.08 |
| Cpne4 | 0.01 | 0.11 | 0.26 | 0.04 | 0.31 |
| Creb5 | 14.35 | 18.22 | 18.66 | 5.66 | 4.93 |
| Csad | 0.13 | 0.23 | 0.27 | 0.37 | 0.50 |
| Csf1 | 18.25 | 12.77 | 18.53 | 14.82 | 5.53 |
| Cstb | 12.41 | 7.62 | 4.58 | 3.37 | 1.65 |
| Ctnna2 | 0.06 | 0.05 | 0.32 | 0.17 | 0.68 |
| Ctsl | 8.23 | 5.63 | 4.16 | 2.24 | 2.04 |
| Cxcl1 | 127.77 | 73.19 | 188.27 | 100.08 | 20.11 |
| Cxcl10 | 9.35 | 8.90 | 27.50 | 5.51 | 5.61 |
| Cxcl12 | 0.09 | 0.06 | 0.32 | 0.76 | 1.46 |
| Cxcl2 | 26.16 | 30.16 | 123.70 | 59.78 | 16.85 |
| Cyp2d26 | 0.03 | 0.02 | 0.12 | 0.32 | 0.54 |
| Cyp2d9 | 0.12 | 0.01 | 0.21 | 0.24 | 0.81 |
| Cyp2e1 | 0.07 | 0.04 | 0.18 | 0.26 | 0.54 |
| Cyp2j11 | 0.06 | 0.06 | 0.21 | 0.29 | 0.64 |
| Cyp2j7-ps | 0.01 | 0.21 | 0.14 | 0.43 | 0.57 |
| Cyp51 | 0.09 | 0.07 | 0.10 | 0.20 | 0.44 |
| Cyp7b1 | 0.14 | 0.05 | 0.11 | 0.22 | 0.44 |
| D17H6S56E-5 | 6.95 | 9.37 | 16.67 | 9.58 | 4.24 |
| D630024D03Rik | 0.01 | 0.03 | 0.08 | 0.14 | 0.34 |
| D630029K05Rik | 0.05 | 0.07 | 0.31 | 0.22 | 0.72 |
| Dcxr | 0.06 | 0.24 | 0.23 | 0.26 | 0.46 |
| Defb19 | 0.12 | 0.03 | 0.03 | 0.05 | 0.26 |
| Diap3 | 4.48 | 10.56 | 6.29 | 3.13 | 1.97 |
| Dnase1 | 0.20 | 0.02 | 0.04 | 0.09 | 0.58 |
| Dpep1 | 0.04 | 0.05 | 0.13 | 0.34 | 0.67 |
| Dpf3 | 0.04 | 0.04 | 0.21 | 0.24 | 0.23 |
| Dtl | 11.23 | 16.48 | 13.48 | 3.21 | 2.69 |
| Dusp15 | 0.01 | 0.03 | 0.07 | 0.13 | 0.23 |
| E2f8 | 4.99 | 15.63 | 7.41 | 8.49 | 2.09 |
| Ear2 | 2.98 | 1.00 | 1.32 | 36.56 | 102.49 |
| Eci3 | 0.09 | 0.04 | 0.11 | 0.11 | 0.30 |
| Edn1 | 7.66 | 9.86 | 15.00 | 20.66 | 4.24 |
| Egf | 0.01 | 0.01 | 0.08 | 0.20 | 0.61 |
| Egfl6 | 0.10 | 0.24 | 0.20 | 0.72 | 1.39 |
| Egr2 | 20.16 | 17.85 | 17.11 | 53.69 | 44.00 |
| Elf3 | 5.77 | 8.65 | 16.60 | 5.84 | 3.80 |
| Emr1 | 0.35 | 0.26 | 4.39 | 13.66 | 7.73 |
| Esm1 | 0.34 | 0.06 | 0.10 | 0.25 | 0.37 |
| Fam107a | 0.03 | 0.08 | 0.21 | 0.26 | 0.57 |
| Fam151a | 0.02 | 0.13 | 0.14 | 0.18 | 0.28 |
| Fam65c | 0.06 | 0.52 | 0.62 | 1.26 | 1.25 |
| Fbln1 | 0.10 | 0.08 | 0.93 | 1.22 | 1.18 |
| Fbxo40 | 0.08 | 0.19 | 0.28 | 0.31 | 0.37 |
| Fcamr | 0.10 | 0.08 | 0.23 | 0.39 | 0.69 |
| Fcgr1 | 9.39 | 6.00 | 22.31 | 39.89 | 31.91 |
| Fcgr4 | 0.05 | 0.11 | 0.42 | 1.52 | 0.73 |
| Fcrls | 1.05 | 3.75 | 13.83 | 196.20 | 94.44 |
| Fga | 34.86 | 14.86 | 8.60 | 1.86 | 0.95 |
| Fgb | 264.53 | 40.24 | 3.56 | 2.39 | 1.00 |
| Fgg | 40.51 | 21.72 | 4.02 | 1.97 | 2.56 |
| Fibin | 0.09 | 0.10 | 0.09 | 0.10 | 0.31 |
| Figf | 0.11 | 0.39 | 0.61 | 1.71 | 1.25 |
| Fitm1 | 0.07 | 0.10 | 0.40 | 0.83 | 0.71 |
| Fmod | 0.02 | 0.20 | 0.23 | 0.20 | 0.84 |
| Fn1 | 2.58 | 7.73 | 8.28 | 10.82 | 10.31 |
| Fn3k | 0.07 | 0.11 | 0.25 | 0.38 | 0.57 |
| Fndc4 | 13.11 | 13.41 | 2.86 | 3.99 | 2.98 |
| Foxj1 | 49.71 | 22.09 | 34.44 | 32.56 | 16.49 |
| Ftcd | 0.09 | 0.08 | 0.32 | 0.11 | 0.44 |
| G6pc | 0.01 | 0.05 | 0.18 | 0.30 | 0.50 |
| Gabrp | 6.02 | 9.83 | 5.83 | 15.00 | 65.70 |
| Galnt11 | 0.09 | 0.24 | 0.40 | 0.40 | 0.82 |
| Gamt | 0.07 | 0.36 | 0.27 | 0.48 | 0.65 |
| Gatm | 0.03 | 0.04 | 0.09 | 0.14 | 0.34 |
| Gc | 17.61 | 26.20 | 16.91 | 10.00 | 5.25 |
| Gdf15 | 9.59 | 20.28 | 8.04 | 1.35 | 0.71 |
| Ggct | 0.13 | 0.12 | 0.09 | 0.27 | 0.23 |
| Gm10804 | 0.11 | 0.24 | 0.28 | 0.36 | 0.46 |
| Gm11128 | 0.06 | 0.09 | 0.37 | 0.49 | 1.07 |
| Gm11428 | 0.80 | 0.52 | 2.12 | 10.23 | 6.82 |
| Gm11825 | 0.32 | 0.03 | 0.13 | 0.06 | 0.26 |
| Gm11992 | 0.08 | 0.15 | 0.30 | 0.37 | 0.80 |

TABLE 1-continued

List of genes identified by RNA-seq as significantly different from normal at least at one time-point in the FA nephropathy progression. Data is presented as mean fold change from normal (n = 3/group); gene symbols in bold indicate the 10 candidates selected; gene symbols in italics indicate those that also met the selection criteria but were not chosen; fold changes in bold indicate p < 0.2 at DESeq analysis.

| Mgi symbol | Day 1 | Day 2 | Day 3 | Day 7 | Day 14 |
|---|---|---|---|---|---|
| Gm12326 | 0.05 | 0.05 | 0.05 | 0.19 | 0.07 |
| Gm13262 | 0.05 | 0.10 | 0.60 | 0.77 | 1.74 |
| Gm15848 | 0.10 | 0.12 | 0.19 | 0.51 | 0.63 |
| Gm15987 | 3.37 | 4.21 | 28.79 | 65.24 | 30.96 |
| Gm20614 | 0.04 | 0.04 | 0.05 | 0.07 | 0.23 |
| Gm4450 | 0.08 | 0.14 | 0.10 | 0.26 | 0.43 |
| Gm4952 | 0.08 | 0.04 | 0.05 | 0.05 | 0.31 |
| Gm4956 | 0.04 | 0.01 | 0.15 | 0.66 | 0.82 |
| Gm5424 | 0.11 | 0.08 | 0.18 | 0.25 | 0.45 |
| Gm5887 | 0.09 | 0.03 | 0.47 | 0.22 | 0.11 |
| Gm8126 | 31.61 | 13.16 | 14.35 | 7.32 | 5.48 |
| Gm853 | 0.21 | 0.36 | 0.33 | 0.12 | 0.31 |
| Gm9732 | 24.08 | 1.53 | 8.94 | 11.84 | 14.82 |
| Golm1 | 9.24 | 17.30 | 7.96 | 5.28 | 4.33 |
| Gpr114 | 13.56 | 5.89 | 19.53 | 21.52 | 20.80 |
| Gpx6 | 0.05 | 0.18 | 0.14 | 0.28 | 0.68 |
| Gxylt2 | 16.28 | 12.14 | 14.04 | 7.30 | 12.54 |
| Gyk | 0.12 | 0.19 | 0.40 | 0.45 | 0.65 |
| Gys2 | 0.04 | 0.29 | 0.31 | 0.33 | 0.39 |
| H2-DMa | 5.83 | 10.07 | 16.12 | 24.55 | 9.89 |
| *H2-DMb1* | 1.95 | 4.44 | 6.68 | 10.89 | 8.21 |
| Haao | 0.13 | 0.08 | 0.16 | 0.21 | 0.37 |
| Hao2 | 0.10 | 0.32 | 0.33 | 0.38 | 0.52 |
| Hapln1 | 0.01 | 0.01 | 0.24 | 0.08 | 0.52 |
| Havcr1 | 137.33 | 53.77 | 26.32 | 10.03 | 2.00 |
| Hba-a1 | 0.13 | 0.56 | 0.05 | 0.26 | 0.45 |
| Hba-a2 | 0.42 | 0.89 | 0.06 | 0.68 | 0.61 |
| Hbb-b1 | 0.32 | 0.46 | 0.04 | 0.36 | 0.52 |
| Hpcal4 | 4.09 | 9.66 | 2.91 | 4.59 | 1.33 |
| Hpd | 0.01 | 0.01 | 0.08 | 0.37 | 0.39 |
| Icam1 | 16.30 | 24.35 | 20.70 | 9.29 | 5.87 |
| Id1 | 5.53 | 10.02 | 3.26 | 2.47 | 1.55 |
| Ido2 | 0.01 | 0.05 | 0.18 | 0.19 | 0.58 |
| Igfbp1 | 0.01 | 0.04 | 0.13 | 0.18 | 0.40 |
| Igj | 0.27 | 0.02 | 0.33 | 0.81 | 0.42 |
| Il1f6 | 2.45 | 10.46 | 27.71 | 10.99 | 10.49 |
| Il1rn | 42.57 | 51.91 | 88.49 | 62.43 | 29.62 |
| Inmt | 0.03 | 0.03 | 0.13 | 0.13 | 0.63 |
| Inpp4b | 0.23 | 0.06 | 0.29 | 0.92 | 0.71 |
| Irx1 | 0.06 | 0.16 | 0.28 | 0.47 | 0.68 |
| *Itgam* | 10.37 | 10.62 | 31.52 | 65.37 | 35.56 |
| Itih5 | 0.15 | 0.10 | 0.38 | 0.80 | 0.87 |
| Kap | 0.25 | 0.07 | 0.14 | 0.10 | 0.42 |
| Kbtbd11 | 0.11 | 0.20 | 0.57 | 0.43 | 0.69 |
| Kcng1 | 0.02 | 0.05 | 0.34 | 0.08 | 0.40 |
| Kcnh4 | 0.03 | 0.20 | 0.80 | 0.41 | 0.34 |
| Kcnj1 | 0.12 | 0.18 | 0.49 | 0.55 | 0.84 |
| Kcnj8 | 0.11 | 0.03 | 0.02 | 0.36 | 0.45 |
| Kcnt1 | 0.01 | 0.09 | 0.25 | 0.16 | 0.20 |
| Khk | 0.12 | 0.19 | 0.39 | 0.33 | 0.66 |
| Kif11 | 3.95 | 12.89 | 6.53 | 2.81 | 2.66 |
| Kif18b | 23.46 | 43.53 | 32.02 | 13.75 | 6.78 |
| Kif4 | 7.35 | 17.87 | 20.69 | 3.59 | 7.27 |
| Klf6 | 8.02 | 10.33 | 10.92 | 7.08 | 3.68 |
| Kntc1 | 5.77 | 21.92 | 23.49 | 6.04 | 4.88 |
| Krt20 | 99.65 | 40.80 | 65.31 | 49.83 | 23.54 |
| Laptm5 | 1.62 | 2.12 | 8.68 | 10.60 | 8.39 |
| *Lbp* | 4.30 | 10.70 | 14.46 | 14.44 | 5.52 |
| Lcn2 | 172.35 | 573.77 | 145.51 | 116.16 | 47.87 |
| Lgals1 | 11.64 | 9.01 | 9.68 | 3.65 | 2.18 |
| Lrg1 | 27.42 | 16.81 | 7.70 | 2.90 | 1.38 |
| Lrrc66 | 0.04 | 0.07 | 0.29 | 0.20 | 1.07 |
| Lyz1 | 1.01 | 1.02 | 13.19 | 13.96 | 93.62 |
| *Lyz2* | 2.49 | 2.57 | 10.50 | 26.25 | 25.76 |
| Macrod2 | 0.12 | 0.10 | 0.22 | 0.21 | 0.42 |
| Mcm6 | 14.09 | 40.99 | 11.80 | 3.87 | 6.63 |
| Meox1 | 0.60 | 0.04 | 0.50 | 0.27 | 1.19 |
| Mep1b | 0.04 | 0.00 | 0.21 | 0.18 | 0.56 |
| Mgp | 0.85 | 0.55 | 3.30 | 9.97 | 9.57 |
| Miox | 0.04 | 0.05 | 0.21 | 0.25 | 0.49 |
| Mir1943 | 0.04 | 0.04 | 0.37 | 0.34 | 0.20 |
| Mki67 | 2.93 | 19.47 | 10.87 | 3.31 | 2.63 |
| Mmp27 | 55.82 | 13.03 | 15.58 | 2.66 | 3.55 |
| *Mmp7* | 4.72 | 12.29 | 10.09 | 24.03 | 29.14 |
| Mpv17l | 0.20 | 0.08 | 0.31 | 0.30 | 0.42 |
| Mrc1 | 0.61 | 0.51 | 4.86 | 9.29 | 5.48 |
| Mrvi1 | 0.04 | 0.08 | 0.50 | 1.01 | 1.75 |
| Msi1 | 18.45 | 37.45 | 12.49 | 27.16 | 13.73 |
| Mthfd2 | 17.65 | 10.04 | 19.94 | 11.54 | 1.37 |
| Muc4 | 73.06 | 239.90 | 154.46 | 104.49 | 53.83 |
| Mvp | 10.42 | 7.90 | 4.41 | 3.04 | 2.27 |
| Myct1 | 1.76 | 0.05 | 0.55 | 0.77 | 1.14 |
| Nccrp1 | 0.00 | 0.00 | 0.00 | 0.07 | 0.28 |
| Nckap1l | 1.90 | 1.59 | 5.90 | 13.46 | 4.67 |
| Nek6 | 8.68 | 4.74 | 4.62 | 2.17 | 2.61 |
| *Nfam1* | 3.49 | 24.67 | 19.48 | 59.18 | 68.60 |
| Nfkbiz | 11.90 | 10.97 | 12.66 | 9.70 | 5.33 |
| Npas2 | 0.24 | 0.44 | 0.22 | 0.19 | 0.04 |
| Npy | 0.08 | 0.02 | 0.05 | 0.24 | 0.41 |
| *Npy6r* | 20.73 | 46.40 | 36.78 | 58.69 | 20.39 |
| Pah | 0.07 | 0.10 | 0.22 | 0.24 | 0.57 |
| Pck1 | 0.11 | 0.17 | 0.48 | 0.68 | 1.24 |
| Pde6a | 0.04 | 0.02 | 0.08 | 0.10 | 0.60 |
| Pdlim7 | 10.80 | 12.49 | 9.44 | 5.09 | 3.51 |
| Pdpn | 11.67 | 43.96 | 19.72 | 24.06 | 18.54 |
| Pea15a | 8.58 | 9.88 | 5.89 | 3.73 | 2.03 |
| Pecr | 0.12 | 0.13 | 0.23 | 0.30 | 0.49 |
| Pfn3 | 0.02 | 0.13 | 0.44 | 0.47 | 0.41 |
| Pla1a | 0.39 | 0.04 | 0.32 | 1.29 | 1.36 |
| Plac8 | 9.91 | 5.10 | 17.08 | 17.41 | 5.99 |
| Pld4 | 0.93 | 2.37 | 7.79 | 19.53 | 14.74 |
| Plin2 | 50.30 | 21.47 | 11.95 | 4.65 | 2.72 |
| Pltp | 0.07 | 0.13 | 1.31 | 5.15 | 3.25 |
| Ppp1r1a | 0.09 | 0.13 | 0.30 | 0.95 | 1.15 |
| Prox1 | 0.07 | 0.27 | 0.25 | 0.57 | 1.37 |
| Proz | 0.03 | 0.06 | 0.38 | 0.24 | 1.50 |
| Psrc1 | 22.63 | 17.94 | 23.39 | 7.74 | 4.76 |
| Ptgis | 0.05 | 0.66 | 0.22 | 1.98 | 0.84 |
| Pvalb | 0.02 | 0.04 | 0.11 | 0.23 | 0.56 |
| Pxmp2 | 0.05 | 0.15 | 0.42 | 0.37 | 0.65 |
| Pzp | 0.27 | 0.03 | 0.09 | 0.12 | 0.56 |
| Rad51l1 | 37.27 | 7.51 | 23.21 | 20.85 | 17.35 |
| Rcan1 | 7.81 | 6.35 | 3.48 | 2.13 | 1.26 |
| Rras | 8.93 | 8.77 | 7.99 | 4.42 | 4.46 |
| Rrm2 | 9.69 | 26.46 | 26.37 | 3.25 | 3.28 |
| S100g | 0.12 | 0.07 | 0.07 | 0.49 | 1.23 |
| Saa1 | 246.34 | 99.00 | 76.73 | 6.60 | 1.00 |
| Sacs | 10.20 | 5.88 | 4.39 | 3.26 | 2.93 |
| Scn7a | 0.19 | 0.11 | 1.21 | 2.79 | 4.42 |
| Sectm1b | 0.03 | 0.10 | 0.42 | 0.43 | 0.64 |
| *Sema3d* | 0.23 | 0.06 | 0.31 | 6.90 | 6.30 |
| Serpina10 | 315.61 | 302.11 | 309.89 | 182.59 | 72.73 |
| Serpina3n | 101.28 | 251.85 | 99.04 | 111.79 | 98.42 |
| Serpina7 | 99.83 | 49.78 | 20.22 | 18.24 | 3.58 |
| Serpine1 | 212.01 | 74.08 | 63.25 | 108.17 | 65.09 |
| *Serpine2* | 2.10 | 0.30 | 5.33 | 22.57 | 16.36 |
| Sfrp1 | 0.15 | 0.33 | 0.71 | 0.84 | 1.24 |
| Sirpb1c | 1.87 | 1.59 | 2.96 | 15.66 | 8.93 |
| Slc10a6 | 0.09 | 0.28 | 0.18 | 1.08 | 1.83 |
| Slc12a1 | 0.04 | 0.06 | 0.21 | 0.51 | 0.83 |
| Slc16a1 | 0.60 | 0.32 | 0.46 | 0.14 | 0.15 |
| Slc16a7 | 0.11 | 0.09 | 0.17 | 0.58 | 0.86 |
| Slc22a13 | 0.19 | 0.12 | 0.25 | 0.23 | 0.52 |
| Slc22a19 | 0.26 | 0.05 | 0.16 | 0.34 | 0.54 |
| Slc22a22 | 0.02 | 0.01 | 0.18 | 0.19 | 0.66 |
| Slc22a26 | 0.16 | 0.02 | 0.12 | 0.14 | 0.34 |
| Slc22a28 | 0.07 | 0.16 | 0.18 | 0.15 | 0.51 |
| Slc22a30 | 0.08 | 0.08 | 0.20 | 0.15 | 0.44 |
| Slc22a7 | 0.13 | 0.00 | 0.07 | 0.04 | 0.43 |
| Slc22a8 | 0.22 | 0.07 | 0.20 | 0.27 | 0.66 |

TABLE 1-continued

List of genes identified by RNA-seq as significantly different from normal at least at one time-point in the FA nephropathy progression. Data is presented as mean fold change from normal (n = 3/group); gene symbols in bold indicate the 10 candidates selected; gene symbols in italics indicate those that also met the selection criteria but were not chosen; fold changes in bold indicate p < 0.2 at DESeq analysis.

| Mgi symbol | Day 1 | Day 2 | Day 3 | Day 7 | Day 14 |
|---|---|---|---|---|---|
| Slc25a24 | 15.48 | 10.59 | 10.39 | 10.01 | 9.91 |
| Slc28a1 | 0.02 | 0.19 | 0.18 | 0.44 | 0.55 |
| Slc2a5 | 0.07 | 0.09 | 0.21 | 0.25 | 0.99 |
| Slc34a1 | 0.05 | 0.11 | 0.33 | 0.30 | 0.58 |
| Slc34a2 | 11.81 | 16.20 | 7.59 | 7.02 | 4.10 |
| Slc34a3 | 0.05 | 0.05 | 0.09 | 0.20 | 0.33 |
| Slc46a3 | 0.11 | 0.36 | 0.57 | 0.31 | 0.53 |
| Slc4a1 | 0.11 | 0.09 | 0.18 | 0.35 | 0.92 |
| Slc5a12 | 0.06 | 0.34 | 0.38 | 0.35 | 0.58 |
| Slc5a4a | 0.02 | 0.37 | 0.51 | 0.17 | 1.06 |
| Slc6a12 | 0.02 | 0.13 | 0.26 | 0.12 | 0.77 |
| Slc7a13 | 0.02 | 0.02 | 0.11 | 0.10 | 0.48 |
| Slco1a1 | 0.18 | 0.16 | 0.19 | 0.12 | 0.36 |
| Smoc2 | 0.06 | 0.06 | 1.83 | 4.22 | 6.08 |
| Smpdl3b | 222.02 | 124.22 | 111.13 | 38.83 | 19.27 |
| Snx31 | 0.06 | 0.05 | 0.07 | 0.07 | 0.27 |
| Socs3 | 77.54 | 53.23 | 43.48 | 34.95 | 36.18 |
| Sox4 | 12.86 | 13.93 | 11.69 | 11.09 | 7.60 |
| Sox9 | 24.10 | 49.89 | 52.43 | 30.72 | 8.17 |
| Spaca7 | 27.30 | 74.80 | 18.32 | 30.89 | 11.81 |
| Spink6 | 46.74 | 13.93 | 9.16 | 5.47 | 1.77 |
| Spp1 | 113.22 | 174.85 | 63.01 | 37.70 | 10.75 |
| Spred3 | 6.01 | 11.03 | 8.99 | 3.82 | 5.60 |
| Spsb1 | 11.68 | 13.04 | 4.64 | 8.93 | 4.14 |
| Sptlc3 | 0.07 | 0.11 | 1.02 | 1.25 | 0.68 |
| St8sia2 | 3.07 | 2.10 | 10.17 | 26.47 | 2.02 |
| Stil | 13.84 | 32.74 | 10.68 | 3.57 | 0.95 |
| Stk32a | 10.38 | 7.59 | 5.33 | 2.72 | 1.64 |
| Stra6 | 1.19 | 1.95 | 8.56 | 22.31 | 14.59 |
| Susd2 | 0.18 | 0.07 | 0.32 | 0.28 | 0.51 |
| Sycn | 0.07 | 0.07 | 0.07 | 0.07 | 0.22 |
| Synpr | 0.23 | 0.02 | 0.01 | 0.01 | 0.18 |
| Sytl2 | 3.75 | 5.53 | 8.20 | 11.81 | 6.72 |
| Tagln2 | 8.92 | 6.40 | 4.86 | 4.01 | 2.37 |
| Tbx10 | 0.06 | 0.10 | 0.08 | 0.03 | 0.44 |
| Timd2 | 7.27 | 2.97 | 1.47 | 0.68 | 0.67 |
| Timp1 | 175.24 | 194.76 | 60.56 | 67.32 | 61.27 |
| Tlr2 | 6.43 | 12.76 | 34.62 | 15.78 | 7.34 |
| Tmem207 | 0.01 | 0.02 | 0.14 | 0.35 | 1.20 |
| Tmem25 | 0.11 | 0.34 | 0.39 | 0.53 | 0.53 |
| Tmem26 | 0.10 | 0.07 | 0.16 | 0.16 | 0.49 |
| Tmsb10 | 19.04 | 18.72 | 9.84 | 9.28 | 5.31 |
| *Tnc* | 13.27 | 9.63 | 9.00 | 16.74 | 18.78 |
| Tnfaip3 | 1.97 | 3.85 | 6.38 | 8.79 | 3.95 |
| Tnfrsf23 | 18.16 | 7.62 | 5.65 | 2.21 | 1.75 |
| Top2a | 5.38 | 15.75 | 10.49 | 5.58 | 3.30 |
| Tpx2 | 3.87 | 10.97 | 7.65 | 2.93 | 2.69 |
| Tril | 0.07 | 0.43 | 0.69 | 2.07 | 0.97 |
| Tsc22d1 | 8.11 | 6.92 | 4.34 | 2.18 | 2.00 |
| Ttc36 | 0.04 | 0.10 | 0.34 | 0.34 | 0.67 |
| Ttr | 0.05 | 0.04 | 0.15 | 0.56 | 0.78 |
| *Tyrobp* | 1.26 | 1.65 | 4.90 | 16.29 | 10.29 |
| Ugt3a1 | 0.18 | 0.07 | 0.17 | 0.22 | 0.46 |
| Uhrf1 | 16.90 | 31.75 | 12.11 | 3.81 | 3.48 |
| Upp2 | 0.25 | 0.11 | 0.21 | 0.69 | 1.34 |
| Vcam1 | 13.66 | 30.80 | 121.91 | 63.51 | 36.46 |
| Vill | 0.09 | 0.28 | 0.18 | 0.20 | 0.36 |
| Vmn1r-ps11 | 0.02 | 0.03 | 0.73 | 0.11 | 0.51 |
| Vmn1r18 | 0.02 | 0.01 | 0.14 | 0.27 | 0.87 |
| Vmn1r19 | 0.03 | 0.02 | 0.52 | 0.73 | 1.04 |
| Vmn1r20 | 0.02 | 0.34 | 0.31 | 0.27 | 0.79 |
| Vstm2a | 0.04 | 0.05 | 0.04 | 0.20 | 0.60 |
| Vtcn1 | 64.93 | 44.16 | 28.37 | 15.70 | 7.44 |
| Vwce | 0.06 | 0.08 | 0.42 | 1.03 | 0.85 |
| Wfdc15b | 0.02 | 0.05 | 0.06 | 0.27 | 0.90 |
| Ybx2 | 0.08 | 0.12 | 0.18 | 0.72 | 0.44 |
| 2310042D19Rik | 0.09 | 0.08 | 0.47 | 0.46 | 0.95 |
| 4930533I22Rik | 0.11 | 0.09 | 0.22 | 0.25 | 0.74 |
| 4933417A18Rik | 0.04 | 0.07 | 0.49 | 0.41 | 0.67 |
| 7SK RNA | 0.04 | 0.04 | 0.08 | 0.08 | 1.35 |
| 8430408G22Rik | 0.09 | 0.23 | 0.34 | 1.23 | 0.79 |
| 9030619P08Rik | 0.01 | 0.05 | 0.02 | 0.03 | 0.25 |

TABLE 2

List of primers used for mouse qRT-PCR

| Gene | F/R | Sequence | SEQ ID NO |
|---|---|---|---|
| Cdh11 | F | TGC CAA TCT TCT TTT CGT TCT T | 0003 |
| | R | CCT TGA AAG GTC CAT TGC TG | 0004 |
| Gabrp | F | TGT GGA GGT CAG CAG AAG TG | 0005 |
| | R | CAG TGC TAT CCG AAC TGG GT | 0006 |
| Mgp | F | AGG CAG ACT CAC AGG ACA CC | 0007 |
| | R | AGG ACT CCA TGC TTT CGT GA | 0008 |
| Mrc1 | F | CCT CTT AAT TCA GCA TCA CTT GC | 0009 |
| | R | TGC ATT GCC CAG TAA GGA GT | 0010 |
| Pld4 | F | ATT CTG GGT TGT GGA TGG G | 0011 |
| | R | CAA GGT CTT GAG CCA GGT TG | 0012 |
| Pltp | F | TGA GGG GCG TGT CAC TAC TT | 0013 |
| | R | CGA GAT CAT CCA CAG AAC TGC | 0014 |
| Scn7a | F | AAA TGA AAC GCT GCA CAA CA | 0015 |
| | R | CAG CAT CTG TCC TGT TGC C | 0016 |
| Smoc2 | F | ACT GCG ACA TGA ACA ATG ACA | 0017 |
| | R | ACT TTC AGC ATT TCC TCT GGG | 0018 |

TABLE 2-continued

List of primers used for mouse qRT-PCR

| Gene | F/R | Sequence | SEQ ID NO |
|---|---|---|---|
| Stra6 | F | TGC CTT CCT TCT ATC CTG TCC | 0019 |
| | R | AGG ACC ACA AAG ACA GCA GC | 0020 |
| Sytl2 | F | TGA AGG AAT GCC TTG ACC TC | 0021 |
| | R | ACA GCT CTT GTC TTC TGG CG | 0022 |
| Col1a1 | F | TGA CTG GAA GAG CGG AGA GT | 0023 |
| | R | GTT CGG GCT GAT GTA CCA GT | 0024 |
| Fn1 | F | ATG TGG ACC CCT CCT GAT AGT | 0025 |
| | R | GCC CAG TGA TTT CAG CAA AGG | 0026 |
| Kim-1 | F | GGA AGT AAA GGG GGT AGT GGG | 0027 |
| | R | AAG CAG AAG ATG GGC ATT GC | 0028 |
| Gapdh | F | GAA TAC GGC TAC AGC AAC AGG | 0029 |
| | R | GGT CTG GGA TGG AAA TTG TG | 0030 |

TABLE 3

List of primers used for human qRT-PCR

| Gene | F/R | Sequence | SEQ ID NO |
|---|---|---|---|
| Cdh11 | F | AGG GAC AAC CAA AGT GAC GA | 0031 |
| | R | GGC TGC TTC TGA CAC AGA CA | 0032 |
| Gabrp | F | TAG TCA CCA GAT CGC AGC AG | 0033 |
| | R | GAA CAT TCC TCC GAA GCT CA | 0034 |
| Mgp | F | ACG AAA CCA TGA AGA GCC TG | 0035 |
| | R | AAC TGA AAC GAT ATC AAA GCC G | 0036 |
| Mrc1 | F | AGG AAA AGC TGC CAA CAA CA | 0037 |
| | R | TCC TGA GGT CAA GGA ACT GG | 0038 |
| Pld4 | F | CAG GTG CAG CCC AAG GAC | 0039 |
| | R | GGA TGC TTT CCA CAA GGA CA | 0040 |
| Pltp | F | CGG TCC TGC TCA ACT CCC | 0041 |
| | R | GAA GTC CAT GTC CAG GTT GC | 0042 |
| Scn7a | F | AGC CCT TGG AAG ATG TGG AC | 0043 |
| | R | AAG CCG CAT TGA ATC TGA AG | 0044 |
| Smoc2 | F | CCG TAC AAG AAC TGA TGG GC | 0045 |
| | R | CTT TCA GCA TGA CCT CTG GG | 0046 |
| Stra6 | F | CTC CAG ACC CTG ACC TCT CA | 0047 |
| | R | AGC AGG ACA AGA CCA AGG CT | 0048 |
| Sytl2 | F | CCA GTA TGT CCC AGA GCC AG | 0049 |
| | R | TGA CTT CCC CTT AGC AGT GG | 0050 |
| Col1a1 | F | AGG CTG GTG TGA TGG GAT T | 0051 |
| | R | GGA ACA CCT CGC TCT CCA G | 0052 |
| Gapdh | F | ATT GCC CTC AAC GAC CAC TTT G | 0053 |
| | R | TCT CTC TTC CTC TTG TGC TCT TGC | 0054 |

TABLE 6

Localization of candidate proteins in normal and fibrotic kidneys from mice and humans.

| | Normal | Fibrotic |
|---|---|---|
| CDH11 | Very fine granular subtle cytoplasmic staining in PT and DT. | More reactivity along the brush border and in cellular debris within the tubule lumens. |
| GABRP | Very mild/minimal cytoplasmic staining in both PT and DT. | Strong reactivity along the apical surface, brush border and in cellular debris within the tubule lumens. |

TABLE 6-continued

Localization of candidate proteins in normal and fibrotic kidneys from mice and humans.

| | Normal | Fibrotic |
|---|---|---|
| MGP | Very minimal and subtle cytoplasmic staining in both PT and DT. | More reactivity along the brush border and in cellular debris within the tubule lumens in mice. Coarse granular reactivity in cytoplasm of some PT, but also along TBM in some tubules. |
| MRC1 | Very minimal, subtle fine granular cytoplasmic staining in PT and DT. | Mild reactivity along the apical surface of PT. |
| PLD4 | Very minimal fine granular cytoplasmic staining, slightly stronger in DT than PT. | Granular cytoplasmic reactivity, stronger in DT than PT in mice. In humans much stronger granular cytoplasmic reactivity in PT, particularly along apical surface. |
| PLTP | Very mild cytoplasmic staining in both PT and DT. | Very mild cytoplasmic staining along the apical surface of PT and also in the DT. |
| SCN7a | Minimal fine granular cytoplasmic staining. | Minimal fine granular cytoplasmic staining plus strong staining in some tubules with irregular granular staining that is stronger along the apical surface as well in the cellular debris in lumens. |
| SMOC2 | Very fine granular subtle cytoplasmic staining in both PT and DT. | Stronger cytoplasmic reactivity in the DT when compared to PT in mice. More reactivity in both PT and DT, but stronger in DT with irregular granular cytoplasmic pattern in humans. |
| STRA6 | Fine granular cytoplasmic staining, slightly more prominent in PT than DT. | Stronger staining in general with nuclear staining in PT. |
| SYTL2 | Very minimal cytoplasmic staining in both PT and DT. | Slight irregular reactivity in some PT. |

Abbreviations:
DT, distal tubule;
PT, proximal tubule;
TBM, tubular basement membrane

TABLE 7

Demographic and clinical characteristics of patients with chronic kidney disease.

| Study ID | Sex | Race | Age | eGFR (ml/min/ 1.73 m$^2$) | Treatment with ACE- inhibitor or ARB | Treatment with diuretic | DM | Presumed cause |
|---|---|---|---|---|---|---|---|---|
| 1 | Male | White | 46 | 40 | 1 | 1 | 1 | DN |
| 2 | Male | White | 65 | 41 | 1 | 0 | 0 | HTN |
| 3 | Female | White | 55 | 23 | 0 | 1 | 1 | DN |
| 4 | Female | Black | 50 | 45 | 1 | 0 | 0 | MCTD |
| 5 | Male | White | 49 | 14 | 1 | 0 | 0 | ANCA |
| 6 | Male | White | 76 | 44 | 0 | 0 | 0 | HTN |
| 7 | Female | Black | 55 | 39 | 1 | 1 | 0 | MN |
| 8 | Male | Black | 65 | 27 | 1 | 1 | 1 | DM |
| 9 | Male | White | 75 | 39 | 1 | 1 | 1 | DM |
| 10 | Male | Black | 60 | 10 | 1 | 1 | 1 | DM, HTN |
| 11 | Male | White | 71 | 30 | 0 | 0 | 1 | DM, HTN |
| 12 | Male | White | 75 | 39 | 1 | 0 | 1 | DM |
| 13 | Male | White | 64 | 25 | 0 | 0 | 1 | DM |
| 14 | Male | Black | 61 | 45 | 1 | 1 | 1 | DM |
| 15 | Male | White | 62 | 44 | 0 | 0 | 0 | PKD |
| 16 | Male | White | 62 | 36 | 1 | 1 | 0 | UNKNOWN |
| 17 | Female | Black | 82 | 33 | 1 | 1 | 0 | HTN |
| 18 | Male | White | 65 | 45 | 1 | 0 | 1 | NEPHRECTOMY, HTN |
| 19 | Female | Black | 56 | 20 | 1 | 0 | 0 | HTN |

TABLE 7-continued

Demographic and clinical characteristics of patients with chronic kidney disease.

| Study ID | Sex | Race | Age | eGFR (ml/min/ 1.73 m$^2$) | Treatment with ACE-inhibitor or ARB | Treatment with diuretic | DM | Presumed cause |
|---|---|---|---|---|---|---|---|---|
| 20 | Female | White | 23 | 25 | 1 | 0 | 0 | CNI TOXICITY |
| 21 | Male | White | 75 | 36 | 1 | 0 | 0 | UNKNOWN |
| 22 | Female | Black | 70 | 13 | 1 | 0 | 0 | NEPHRECTOMY |

Abbreviations:
ACE, angiotensin converting enzyme;
ANCA, anti-neutrophil cytoplasmic antibody;
ARB, angiotensin receptor blocker;
CKD, chronic kidney disease;
CNI, calcineurin inhibitor;
DM, diabetes mellitus;
DN, diabetic nephropathy;
eGFR, estimated glomerular filtration rate;
HTN, hypertension;
MCTD, mixed connective tissue disease;
PKD, polycystic kidney disease.

TABLE 8

Demographic characteristics of healthy volunteers.

| Study ID | Sex | Age | Race |
|---|---|---|---|
| 23 | F | 30 | Caucasian |
| 24 | M | 27 | Caucasian |
| 25 | F | 20 | East Asian - China |
| 26 | F | 49 | African-American |
| 27 | F | 19 | East Asian - China |
| 28 | F | 25 | African-American |
| 29 | F | 48 | African-American |
| 30 | F | 29 | African-American |
| 31 | F | 28 | East Asian - Korea |
| 32 | F | 32 | East Asian - China |
| 33 | F | 46 | African-American |
| 34 | M | 28 | East Asian - China |
| 35 | F | 18 | East Asian - Korea |
| 36 | M | 19 | East Asian - China |
| 37 | F | 19 | African-American |
| 38 | M | 23 | African-American |
| 39 | F | 24 | East Asian - China |
| 40 | F | 18 | East Asian - China |
| 41 | F | 24 | African-American |
| 42 | M | 59 | Caucasian |
| 43 | M | 65 | Caucasian |
| 44 | M | 55 | Caucasian |
| 45 | F | 58 | Caucasian |
| 46 | F | 37 | African American |

TABLE 9

List of peptides used for selected reaction monitoring (SRM) assays.

|  | Peptide Sequence | Protein Accession | Gene Symbol | SEQ ID NO: |
|---|---|---|---|---|
| 1 | LHSDIDSGDGNIK | P55287 | CDH11 | 0055 |
| 2 | FIFSLPPEIIHNPNFTVR |  |  | 0056 |
| 3 | VLDVNDNAPK |  |  | 0057 |
| 4 | VEAANVHIDPK |  |  | 0058 |
| 5 | LSLPGFENLTAGYNK | O00591 | GABRP | 0059 |
| 6 | SFLHEVTVGNR |  |  | 0060 |
| 7 | IVDYFTIQNPSNVDHYSK |  |  | 0061 |
| 8 | LFSNGTVLYALR |  |  | 0062 |
| 9 | NANTFISPQQR | P08493 | MGP | 0063 |
| 10 | YAMVYGYNAAYNR |  |  | 0064 |
| 11 | SKPVHELNR |  |  | 0065 |
| 12 | IYGTTDNLCSR | P22897 | MRC1 | 0066 |
| 13 | TGIAGGLWDVLK |  |  | 0067 |
| 14 | NDTLLGIK |  |  | 0068 |
| 15 | ALGGDLASINNK |  |  | 0069 |
| 16 | VFIVPVGNHSNIPFSR | Q96BZ4 | PLD4 | 0070 |
| 17 | SLQALSNPAANVSVDVK |  |  | 0071 |
| 18 | TSTDLQVLAAR |  |  | 0072 |
| 19 | FQPFHGLFDGVPTTAYFSASPPALCPQGR |  |  | 0073 |
| 20 | VSNVSCQASVSR | P55058 | PLTP | 0074 |
| 21 | EGHFYYNISEVK |  |  | 0075 |

TABLE 9-continued

List of peptides used for selected reaction monitoring (SRM) assays.

|    | Peptide Sequence      | Protein Accession | Gene Symbol | SEQ ID NO: |
|----|-----------------------|-------------------|-------------|------------|
| 22 | IYSNHSALESLALIPLQAPLK |                   |             | 0076       |
| 23 | AVEPQLQEEER           |                   |             | 0077       |
| 24 | YSPLDFIPTLQTAR        | Q01118            | SCN7A       | 0078       |
| 25 | LGGSNIFITVK           |                   |             | 0079       |
| 26 | AYFSNGWYR             |                   |             | 0080       |
| 27 | WPQENENETLHNR         |                   |             | 0081       |
| 28 | LSEPDPSHTLEER         | Q9H3U7            | SMOC2       | 0082       |
| 29 | NSVSSCDQEHQSALEEAK    |                   |             | 0083       |
| 30 | YPTLWTEQVK            |                   |             | 0084       |
| 31 | SISVQELMGCLGVAK       |                   |             | 0085       |
| 32 | GAALDLSPLHR           | Q9BX79            | STRA6       | 0086       |
| 33 | GLQSSYSEEYLR          |                   |             | 0087       |
| 34 | AATLDPGYYTYR          |                   |             | 0088       |
| 35 | HGFLSWAR              |                   |             | 0089       |
| 36 | GNIQFAIEYVESLK        | Q9HCH5            | SYTL2       | 0090       |
| 37 | IVSPGLTIHER           |                   |             | 0091       |
| 38 | LTNQFLGGLR            |                   |             | 0092       |
| 39 | SVPAFLQDESDDR         |                   |             | 0093       |

What is claimed herein:

1. A method of treatment for kidney fibrosis and/or chronic kidney disease comprising; measuring a level of expression of SPARC related modular calcium binding 2 (Smoc2) in a test sample obtained from a subject; treating the subject with a kidney fibrosis treatment when the expression level is increased relative to a reference level, wherein the kidney fibrosis treatment is selected from the group consisting of: dialysis; transplant; low protein diet; an ACE inhibitor; an angiotensin H receptor blacker (ARB); lipid control; D-vitamin supplementation; phosphate control; anemia control; acidosis prevention; and uric acid control.

2. The method of claim 1, wherein the treatment comprises administering an antagonist or agonist of Smoc2.

3. The method of claim 1, wherein the method further comprises measuring the level of expression of at least one gene selected from the group consisting of:

Cdh11; Gabrp; Mgp; Pld4; Mrc1; Syt12; Stra6; Scn7a; Sema3d; Pdpn; and Pltp.

4. The method of claim 1, wherein the method further comprises measuring the level of expression of at least one gene selected from the group consisting of:

Cdh11; Gabrp; Mgp; Pld4; Mrc1; Syt12; Stra6; Scn7a; and Pltp.

5. The method of claim 1, wherein the method further comprises measuring the level of expression of at least one gene selected from the group consisting of:

Cdh11; Mrc1; Pltp; and MGP.

6. The method of claim 1, wherein the method further comprises measuring the level of expression of at least one gene selected from the group consisting of:

Cdh11; Pltp; and MGP.

7. The method of claim 1, wherein the expression level of Smoc2 is determined by measuring the level of a nucleic acid.

8. The method of claim 1, wherein the expression level of Smoc2 is measured by measuring the level of the polypeptide expression product.

9. The method of claim 1 further comprising depleting the sample of abundant proteins prior to the measuring step.

10. The method of claim 9, wherein the depletion step comprises affinity chromatography.

11. The method of claim 1, wherein the test sample is a urine sample.

12. The method of claim 1, wherein the reference level is the expression level in a prior sample obtained from the subject.

13. The method of claim 1, wherein the kidney fibrosis is chronic progressive fibrosis.

14. The method of claim 1, wherein the subject is a subject with a condition selected from the group consisting of:

diabetes; diabetic nephropathy; hypertension; acute kidney injury; chronic kidney disease; an autoimmune disease; systemic lupus erythematosus; renal transplant rejection; renal or systemic infections, streptococcal infections, bacterial endocarditis, human immunodeficiency virus, hepatitis B, C; and inflammatory or infiltrative disease; membranoproliferative glomerulonephritis; IgA nephropathy; chemical toxicity poisoning; mechanical damage affecting the kidneys; renal ischemia; microangiopathies; renal artery occlusion; renal atheroembolism; renal vein thrombosis; obstruction of the urinary tract; nephrolithiasis; primary genetic alterations; polycystic kidney disease; and idiopathic chronic kidney disease.

15. A kit for performing the method of claim 1.

16. A method of treating kidney fibrosis or chronic kidney disease, the method comprising administering an antagonist or agonist of SPARC related modular calcium binding 2 (Smoc2).

17. A method of treatment for kidney fibrosis and/or chronic kidney disease comprising;
- treating a subject with a kidney fibrosis treatment when the subject has been determined to have an increased expression level of SPARC related modular calcium binding 2 (Smoc2) relative to a reference level.

18. A method of treatment for kidney fibrosis and/or chronic kidney disease comprising;
- measuring a level of expression of SPARC related modular calcium binding 2 (Smoc2) in a test sample obtained from a subject; and
- treating the subject with a Smoc2 antagonist selected from an antibody reagent and an antibody when the expression level is increased relative to a reference level.

* * * * *

UNITED STATES PATENT AND TRADEMARK OFFICE
CERTIFICATE OF CORRECTION

PATENT NO. : 10,557,171 B2
APPLICATION NO. : 16/140914
DATED : February 11, 2020
INVENTOR(S) : Vishal S. Vaidya, Florin Craciun and Amrendra K. Ajay It is certified that error appears in the above-identified patent and that said Letters Patent is hereby corrected as shown below:

In the Specification

Column 1, Line 16, insert -- STATEMENT OF FEDERALLY SPONSORED RESEARCH
This invention was made with government support under Grant No. ES017543 awarded by the
National Institutes of Health. The government has certain rights in the invention. --

Signed and Sealed this
Twenty-third Day of May, 2023

Katherine Kelly Vidal
*Director of the United States Patent and Trademark Office*